(12) United States Patent
Gangavaramu et al.

(10) Patent No.: US 11,168,314 B2
(45) Date of Patent: Nov. 9, 2021

(54) **MODIFIED CHITINASE FROM *BREVIBACILLUS LATEROSPORUS* LAK 1210 AND USES THEREOF**

(71) Applicants: DEPARTMENT OF BIOTECHNOLOGY, New Delhi (IN); COUNCIL OF SCIENTIFIC AND INDUSTRIAL RESEARCH, New Delhi (IN)

(72) Inventors: Lakshmi Prasanna Gangavaramu, Telangana (IN); Madhusudana Rao Nalam, Telangana (IN); Veerabhadrav Rao Arravapalli, Telangana (IN)

(73) Assignees: DEPARTMENT OF BIOTECHNOLOGY, New Delhi (IN); COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 200 days.

(21) Appl. No.: 16/122,612

(22) Filed: Sep. 5, 2018

(65) Prior Publication Data

US 2019/0127715 A1    May 2, 2019

(30) Foreign Application Priority Data

Sep. 5, 2017   (IN) .............................. 201711031399

(51) Int. Cl.
  *C12N 9/42* (2006.01)
  *A01N 63/50* (2020.01)
(52) U.S. Cl.
  CPC ........... *C12N 9/2442* (2013.01); *A01N 63/50* (2020.01); *C12Y 302/01014* (2013.01)
(58) Field of Classification Search
  None
  See application file for complete search history.

(56) References Cited

U.S. PATENT DOCUMENTS 5,045,314 A    9/1991 Bone et al.

FOREIGN PATENT DOCUMENTS

| WO | 2008031887 A2 | 3/2008 |
| WO | 2013050867 A2 | 4/2013 |
| WO | 2014045131 A1 | 3/2014 |

OTHER PUBLICATIONS

Song et al. Microb Pathog. Jun. 2017;107:62-68. Epub Mar. 19, 2017. (Year: 2017).*
Liu et al. Genes (Basel). Dec. 2015; 6(4): 1268-1282 (Year: 2015).*
Prasanna et al. Appl Microbiol Biotechnol. Feb. 2013;97(4):1601-11. Epub Apr. 29, 2012. (Year: 2013).*
Annamalai et al. Ann Microbiol. Dec. 2011; 61(4): 801-807. (Year: 2011).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Sambrook et al. Molecular cloning A Laboratory Manual, 2nd edition, Cold Spring Harbor, N.Y. 1989, p. 8.46-8.52 and p. 11.2-11.19. (Year: 1989).*
Bakhtiari et al. Avicenna J Med Biotechnol. Jan.-Mar. 2017;9(1):19-22. Abstract (Year: 2017).*
Bruce E. Tabashnik et al., "Insect resistance to Bt crops: lessons from the first billion acres", Nature Biotechnology, vol. 31, pp. 510-521 (Jun. 10, 2013).
David Chandler et al., "The development, regulation and use of biopesticides for integrated pest management", Philosophical Transactions of the Royal Society Biological Sciences, vol. 366, No. 1573, pp. 1987-1998 (2011).
Alfredo Herrera-Estrella et al. "Chitinases for biological control", EXS, vol. 87, pp. 171-184 (1999).
Tamo Fukamizo, "Chitinolytic enzymes: catalysis, substrate binding, and their application", Current Protein and Peptide Science, vol. 1, pp. 105-124 (2000).
Yasuyuki Arakane et al.,"Chitin-Related Enzymes in Agro-Biosciences", Current Drug Drug Targets, vol. 13, No. 4, pp. 442-470 (2012).
Qiang Yan et al., "Bacterial chitinase: nature and perspectives for sustainable bioproduction", Bioresources and Bioprocessing, vol. 2, No. 31, pp. 1-9 (2015).
Bae Keun Park et al., "Applications of Chitin and Its Derivatives in Biological Medicine", International Journal of Molecular Sciences, vol. 11, pp. 5152-516 (2010).
Edmar Justo De Oliveira et al., "Molecular Characterization of Brevibacillus laterosporus and its Potential Use in Biological Control", Applied and Environmental Microbiology , vol. 70, No. 11, pp. 6657-6664 (Dec. 2004).
Luca Ruiu, "Brevibacillus laterosporus, a pathogen of Invertebrates and a Broad-Spectrum Antimicrobial Species", Insects, vol. 4, pp. 476-492 (2013).

(Continued)

*Primary Examiner* — Christian L Fronda
(74) *Attorney, Agent, or Firm* — Sheppard. Mullin, Richter & Hampton LLP

(57) ABSTRACT

The present invention discloses a recombinant, modified extracellular chitinase having an amino acid sequence set forth in SEQ ID NO.4 or SEQ ID NO.5. The recombinant, modified chitinase is derived by inserting two-point mutations at positions 661 and 2158 in the native chitinase gene of *Brevibacillus laterosporus* LAK 1210 which results in amino acid substitution of tyrosine (Y) residue with histidine (H) at positions 221 and 720. The modified chitinase exhibits both exochitinase and endochitinase activity. The recombinant, modified enzyme is thermoactive with a temperature optimum of 55-60° C. and high thermostability (Tm of 66.7° C.), functions in a broad pH range (pH 3.0-11.0) having a pH optimum of 9.0 and also exhibits improved solubility and enhanced efficacy for control of insects and phytopathogenic fungi. The invention further provides improved methods for large scale production of recombinant modified chitinase and rapid, cost-effective purification method by chitin-adsorption affinity chromatography using powdered crustacean shells.

Figure 1:
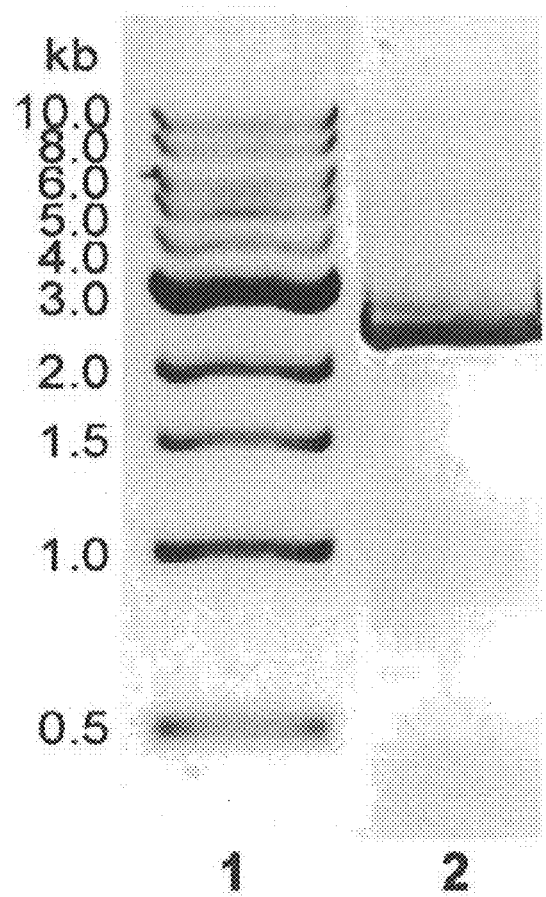

11 Claims, 30 Drawing Sheets
(30 of 30 Drawing Sheet(s) Filed in Color)
Specification includes a Sequence Listing.

(56) References Cited

OTHER PUBLICATIONS

May B. Brurberg et al., "Comparative studies of chitinases A and B from Serratia marcescens", Microbiology, vol. 142, pp. 1581-1589(1996).
Liu et al., "Characterization of Thermotolerant Chitinases Encoded by a Brevibacillus laterosporus Strain Isolated from a Suburban Wetland", Genes, vol. 6, pp. 1268-1282(2015).
V. Shanmugaiah et al., "Optimization of cultural conditions for production of chitinase by Bacillus laterosporus MML2270 isolated from rice rhizosphere soil", African Journal of Biotechnology, vol. 7, No. 15, pp. 2562-2568 (2008).
Xiaowei Huang et al., "An extracellular protease from Brevibacillus laterosporus G4 without parasporal crystals can serve as a pathogenic factor in infection of nematodes", Research in Microbiology, vol. 156, No. 5-6, pp. 719-727 (Jun. 2005).

* cited by examiner

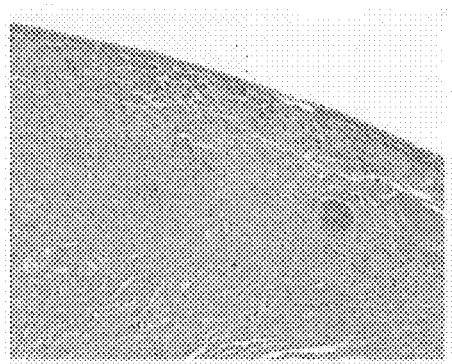 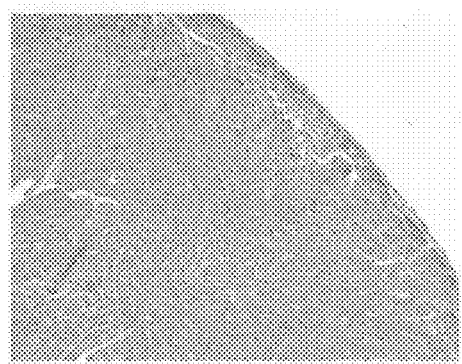
FIGURE 25A                    FIGURE 25B

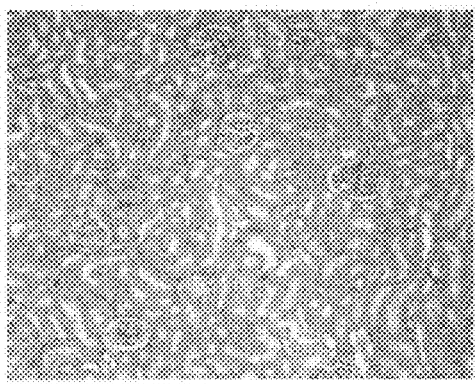
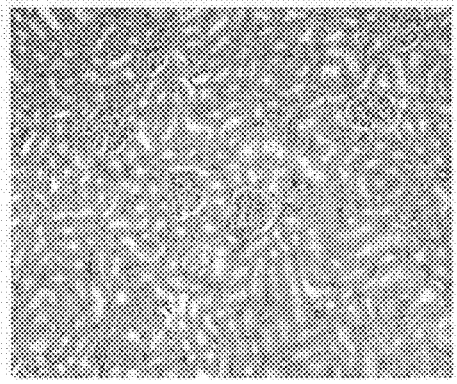
FIGURE 26A                    FIGURE 26B

MODIFIED CHITINASE FROM *BREVIBACILLUS LATEROSPORUS* LAK 1210 AND USES THEREOF

CROSS REFERENCE TO RELATED APPLICATIONS

The present application claims the benefit of, and priority from, Indian Patent Application No. 201711031399 filed on Sep. 5, 2017, which is hereby incorporated by reference in its entirety for all purposes as if fully set forth herein.

FIELD OF INVENTION

The present invention relates to the field of enzyme biotechnology, more specifically a novel chitinase enzyme-based technology for biotechnological applications in agriculture, environment and biomedicine. The present invention pertains to a recombinant extracellular chitinase from *Brevibacillus laterosporus* LAK 1210 for biological control and its other industrial uses.

BACKGROUND OF INVENTION

Typically, plant diseases caused by phytopathogenic organisms including insects and fungi are a major constraint on forest and agricultural productivity. The use of conventional pesticides for plant protection is being undermined by problems related to insect resistance, pest resurgence and environmental concerns. Copping et al (2000) have reported that a variety of insect pests cannot be effectively controlled with available pesticide regimens (Copping, L. G and Menn, J J (2000) *Biopesticides: a review of their action, applications and efficacy. Pest Manag. Sci* 56(8): 651-676). Chandler D, Bailey A S, Tatchell G M Davidson G, Greaves J, Grant W P (2011) *The development, regulation and use of biopesticides for integrated pest management. Phil. Trans. R. Soc. B. Biol. Sciences* 366(1573): 1987-1998). Matyjaszczyk E (2015) *Products containing microorganisms as a tool in integrated pest management and the rules of their market placement in the European Union. Pest Manag. Sci.* 71:1201-1206).

In principle, biopesticides may effectively address most of the challenges related to the use of pesticides and as a result they received ample attention in current research programs on sustainable crop protection. Development and commercial implementation of novel biopesticides has been actively encouraged to realize the utility of effective new pest management solutions. A number of biopesticides currently available for the control of insect pests and phytopathogenic fungi have debatable effectiveness. Though *Bacillus thuringiensis* has been widely used to combat destructive pests, the development of resistance to Bt-insecticides is a clear threat. (Bruce E Tabashnik, Thierry Brévault and Yves Carrière (2013) *Insect resistance to Bt crops: lessons front the first billion acres. Nature Biotechnology* 31: 510-521).

The development of insect resistance to Bt necessitates an in-depth continuing search for new biocontrol agents having activity against a wide variety of insect pests and improved insecticidal activity. There have been few effective microbial insecticides since *Bacillus thuringiensis* (Bt) and there is a quest for novel strains as alternative to Bt control. As an alternative certain naturally-occurring agents have been isolated and developed as pesticides. These include natural strains, novel polypeptides and proteins. Consequently, there is a great interest and utility in finding natural strains and polypeptides with deleterious effect on insect pests and phytopathogenic fungi.

Current and future regimes in integrated pest management would benefit from an intensified focus on enzyme applications for biological pest control. An interesting application of chitinolytic enzymes is in biological control of insect pests and phytopathogenic fungi. (Herrera-Estrella A and Chet I (1999) *Chitinases for biological control. EXS:* 87:171-84). The implication of role of chitinases in biocontrol has been investigated and the approach to chitinolytic enzymes for biocontrol of fungal and insect pathogens is based on the widespread presence of chitin as an integral part of the cell walls of fungi, insect cuticle and crustacean exoskeletons. Chitin present in the cuticle and midgut of insects, cell wall of phytopathogenic fungi will be suitable targets for disruption and perturbation by chitinolytic enzymes. Hence, highly effective chitinases with a rationale of developing chitinase-based biocides that interfere with the chitin biosynthesis in insects and phytopathogenic fungi perfectly fit a modern biopesticide/biocontrol agent with desired efficacy and safety profile. Till date, very few bacterial chitinases with antifungal or insecticidal activity have been identified and biochemically characterized. The research reports are available for the synergistic action of chitinases to potentiate the insecticidal activity of Bt toxins. The low efficiency and high production and purification costs limited the development and commercial use of chitinases as biocides.

Chitin is the main structural component of the fungal cell wall and the exoskeletons of invertebrates, such as insects and crustaceans. Chitin is an insoluble homopolymer of $\beta$-(1,4)-linked N-acetylglucosamine (GlcNAc), is the second most abundant polysaccharide in the biosphere, next to cellulose. Chitinases are glycosyl hydrolases that catalyze the hydrolytic cleavage of the $\beta$-1,4-glycoside bond and are found in including microbes, plants, insects, and mammals (Fukamizo T (2000) *Chitinolytic enzymes: catalysis, substrate binding, and their application. Curr Protein Pept Sci* 1: 105-124). Chitinases mediate the degradation of chitin sources in the nature and also the digestion of chitin present in the exoskeleton and peritrophic membrane (PM) in the midgut of insects to soluble chitooligosaccharides (Gooday G W (1999) *Aggressive and defensive roles for chitinases. EXS:* 87:157-69). Yasuyuki Arakane, Toki Taira, Takayuki Ohnuma and Tamo Fukamizo (2012) *Chitin Related Enzymes in Agro-Biosciences, Current Drug Drug Targets* 13(4): 442-470).

In recent years, significant research has been directed toward the use of chitinolytic enzymes with potential applications in fields as diverse as plant protection, bioremediation, effluent water treatment and drug delivery. (Chavan S B, Deshpande M V (2013) *Chitinolytic enzymes: an appraisal as a product of commercial potential. Biotechnol Prog.* 29(4): 833-46). Microorganisms, in particular bacteria are the major source of most industrially important chitinases (Qiang Yan and Stephen S Fong (2015) *Bacterial chitinase: nature and perspectives for sustainable bioproduction. Bioproc. and Bioeng.* 2 (31) 1-9). Some of the best known chitinolytic bacteria include *Serratia, Bacillus, Aeromonas, Vibrio,* and *Streptomyces.* Chitinases are also reported from other bacterial species like *Enterobacter, Pseudomonas, Alcaligenes* and *Paenibacillus.* With the growing need for green alternatives to industrial processes, chitinases have paved a way for their efficient utilization with new possible applications in biorefinery, single-cell protein production, as a food quality enhancer and for the control of malaria propagation (Bae Keun Park and Moon Moo Kim (2010) *Applications of Chitin and Its Derivatives in Biological Medicine. Int. J. Mol. Sci.* 11 5152-516). Their versatile applications prompted the discovery of new strains that are capable of producing chitinolytic enzymes with novel properties. There is a continuous search for new and novel chitinolytic enzymes with characteristics more suitable for biological control and other industrial applications.

A concerted understanding of structure and function of bacterial chitinases from new strains and organisms will be necessary for advancing chitinase research toward biological control and other novel biotechnological applications. In the current scenario, isolated, thermostable enzymes are preferred over microorganisms for industrial applications, since, unlike many microbes, enzymes remain effective in a wide range of pH and temperature range. Secretion of recombinant enzymes to extracellular milieu is important for the successful use of cheap, efficient and thermostable biomass hydrolyzing enzymes for biorefinery to convert plant biomass to biofuels. There is a search for extracellular chitinolytic enzymes that could enhance bioremediation of recalcitrant compounds and effluent water. Therefore, secretion of expressed recombinant enzyme into the culture medium can be a solution for the large-scale production of recombinant *E. coli* for applications in such industrial bioprocesses Furthermore, thermostable enzymes are resistant to organic solvents, detergents, denaturing agents and better suited for harsh industrial processing conditions in terms of thermal activity and stability. Some extracellular enzymes isolated from mesophiles might be active at considerably higher temperatures than their host's environments.

*Brevibacillus laterosporus* is an emerging entomopathogen and its insecticidal activity has been reported against Lepidoptera, Coleoptera, Diptera and nematodes (Oliveira E J D, L Rabinovitch L, Monnerat R G, Passos L K J and Zahner V (2004) *Molecular Characterization of Brevibacillus laterosporus and its Potential Use in Biological Control. Appl. Environ. Microbiol.* 70 (11): 6657-64).

Though *Brevibacillus laterosporus* is reported to have a wide spectrum of biological activity compared to the most popular entomopathogenic bacteria, *Bacillus thuringiensis* and *Bacillus sphaericus*, its biological control potential has not been fully explored since the attempts to isolate this organism from different ecological niches was not successful since the distribution of strains of *Brevibacillus laterosporus* is limited compared to the strains of *Bacillus thuringiensis* and *Bacillus sphaericus*.

There are very few well documented reports available on the potential use of the entomopathogenic bacterium, *Brevibacillus laterosporus* as an effective biopesticide/biocontrol agent. (Luca Ruiu (2013) *Brevibacillus laterosporus, a pathogen of Invertebrates and a Broad-Spectrum Antimicrobial Species. Insects* 4: 476-492). However, thus far, there are no reports available from the patent and non-patent literature on the uses and commercial exploitation of chitinases from *Brevibacillus laterosporus*. A small number of research articles have been published about the enzymatic profile and effects of toxicity and antagonistic activity from *Brevibacillus laterosporus* strains (Huang X, Tian B, Niu Q, Yang J, Zhang L, Zhang K (2005) *An extracellular protease from Brevibacillus laterosporus G4 without parasporal crystals can serve as a pathogenic factor in infection of nematodes. Res. Microbiol.* 156 (5-6): 719-727).

Shanmugiah et al (2008) have reported the identification and optimized culture conditions for the production of chitinase from *Bacillus laterosporus* MML2270 but chitinolytic activity and insecticidal activity has not been reported for the said strain (Shanmugaiah V, Mathivanan N Balasubramanian N and Manoharan P T (2008) *Optimization of cultural conditions for production of chitinase by Bacillus laterosporus MML2270 isolated from rice rhizosphere soil. African Journal of Biotechnology Vol.* 7 (15): 2562-2568). Sakia et al reported a strain of *Brevibacillus laterosporus* with antibacterial and antifungal compounds and not chitinolytic activity (Saikia R, Gogoi D K, Mazumder S, Yadav A, Sarma R K, Bora T C, Gogoi B K (2011) *Brevibacillus laterosporus strain BPM3, a potential biocontrol agent isolated from a natural hot water spring of Assam, India. Microbiol. Res.*, 166: 216-225).

Liu et al (2005) have reported thermotolerant chitinases (Chi A and Chi C) from *Brevibacillus laterosporus* M64, with a pH optimum of 7.0 and 6.0 and thermal stability up to 55° C. (Pulin Liu, Deyong Cheng and Lihong Miao (2015) *Characterization of Thermotolerant Chitinases Encoded by a Brevibacillus laterosporus Strain Isolated from a Suburban Wetland. Genes* 6: 1268-1282). U.S. Pat. No. 5,045,314A discloses the use of insecticidal strain of *Bacillus laterosporus* against nematode ova/larvae. Ignazio Floris et al (2008) reported an invention which relates to a new bacterial strain used for biological control of insects, especially Dipters (Ignazio Floris, Luca Ruiu, Alberto Satta, Gavino Delrio, Salvatore Rubino, Bianca Paglietti, David John Ellar, Roberto A. Pantaleoni (2008) *Brevibacillus laterosporus strain compositions containing the same and method for the biological control of dipters* (WO2008031887 A2) and published their results on lethal effects of *Brevibacillus laterosporus* on *Musca domestica*. WO200831887 A2 discloses the use of an insecticidal strain of *Brevibacillus lateropsorus* effective against dipterans (mosquitoes and mosquito larvae) and this strain also has been reported to produce only insecticidal proteins, with no chitinase activity. Traves Robert Glare et al reported an invention (WO 2014045131) which discloses the insecticidal activity of the spore toxinsof the three new strains of *Brevibacillus laterosporus* against plant pests, particularly, Lepidoptera and Diptera. (Travis Robert Glare, John Graham Hampton, Murray Paul Cox, Damian Alexander Bienkowski (2014) Novel strains of *brevibacillus laterosporus* as biocontrol agents against plant pests, particularly lepidoptera and diptera (WO 2014045131).

However, usage of chitinases for efficacious pest management and industrial applications have not been successful due to the following factors:
  low expression level of chitinases in native hosts
  additional costs in large-scale production and purification of the recombinant enzyme
  bioconversion activity being restricted to a narrow pH and temperature range
  lack of thermostability
  toxicity to non-target species
  low efficacy and lack of wide spectrum insecticidal and fungicidal activity WO2013050867 A2 provides a biologically pure culture of a new strain of *Brevibacillus laterosporus* designated as Lak 1210 (MTCC 5487) having an accession no 5487, as a dual producer of insecticidal proteins and inducible chitinolytic enzymes with a potential utility in agriculture and forest pest management, plant disease control and mosquito control programs.

The strain *Brevibacillus laterosporus* Lak 1210 (MTCC 5487) is a novel, chitinolytic, insecticidal strain of *Brevibacillus* lateropsurus and its potential insecticidal activity and antifungal activity has not been documented, till it was reported by Prasanna et al. (Prasanna, L, Eijsink, V. G. H, Meadow, R, Gaseidnes, S (2013). *A novel strain of Brevibacillus laterosporus produces chitinases that contribute to its biocontrol potential. Appl. Microbiol. Biotechnol.* 97: 1601-1611) and (Lakshmi Prasanna, G (2012). A chitinase from *Brevibacillus laterosporus*, its production and use thereof. WO 2013050867 A2). WO 2013050867 A2 discloses that the multi-chitinolytic complex from the *Brevibacillus laterosporus* Lak 1210 has shown excellent chitin degradation ability, insecticidal activity against lepidopteran insects (diamond backmoth) as well as antifungal activity against several phytopathogenic fungi. The strains of *Brevibacillus laterosporus* are rarely distributed and more specifically hyperchitinolytic strain of *Brevibacillus laterosporus* is a rare find, the subject for the present invention is to isolate one of the chitinases from the multichitinolytic complex of the newly discovered strain, *Brevibacillus laterosporus* Lak 1210 and clone it in *E. coli* to obtain a recombinant, extracellular chitinase for biocontrol and other industrial applications.

In the present invention, the inventors have identified the issues in prior art and have contemplated a unique enzyme engineering approach wherein a modified recombinant chitinase enzyme from *Brevbacillus laterosporus* Lak 1210 has been invented. The present invention overcomes the technical problems involved in large scale production and cost-effective purification of chitinases for industrial use, existing in the prior art. Apart from several other advantages, the recombinant, modified enzyme is thermoactive (55-60° C.) with high thermo-stability (66.7° C.), can operate at a wide pH range (pH 3.0-11.0) with an alkaline pH optimum of 9.0. Because of the combined exo- and endochitinase activity and its alkaline pH optimum, the recombinant chitinase is highly efficacious in insecticidal knockdown both as a contact biopesticide and ingestion biopesticide. as compared to the other chitinolytic enzymes for biocontrol, existing in the prior art. It is also desirable to expand the insecticidal activity of *Bacillus*-based pesticides with addition of recombinant, modified chitinase for an improved pesticidal activity, where a wider range of pests are impacted.

The present invention overcomes the problems of the prior art to solve a long-standing problem of lack of large scale production and large scale, cost-effective purification methods to produce a highly efficient, industrial chitinase for commercial applications in agriculture, medicine and environment.

SUMMARY OF INVENTION

The present invention extends the current state of the art by engineering a chitinase from *Brevibacillus laterosporus* Lak 1210 in *E. coli* and the use of recombinant chitinase for biocontrol and proposed industrial applications in agriculture, medicine and environment. Since, Bt-based insecticide formulations have to be ingested and the timing is critical to ensure that the bacterial toxins remain stable in the environment until they are ingested by the target insect stage, there is a continuous search for new strains with novel mode of action. The present invention provides a recombinant, modified chitinase which is novel properties which could be an effective protein biopesticide for controlling wide range of insect pests and phytopathogenic fungi and furthermore, with possible industrial applications in agriculture, medicine and environment.

A full length chitinase gene (2583 bp) with a signal peptide of 42 aa (SEQUENCE ID NO: 1) from *Brevibacillus laterosporus* Lak 1210 (deposited under MTCC Accession No. 5487) was mutated at positions 661 and 2158 by site directed mutagenesis. The mutated nucleotide sequence (SEQUENCE ID NO: 3) was cloned in *E. coli* BL 21 (DE 3) for secreted expression of the recombinant, modified chitinase. The recombinant, modified chitinase carries an aminoacid substitution at positions 221 and 720, wherein, the tyrosine was replaced by histidine (example 1 and 2).

The recombinant, modified chitinase enzyme, designated as BRLA_Chi90 is secreted into the extracellular medium making it suitable for large scale production required for several industrial applications of chitinase, which will increase the commercial feasibility of the enzyme (example 3).

Based on the examples, the supporting figures and drawings of the present invention claims a new, non-obvious method of chitinase enzyme-based technology for biological control and industrial uses, the improvements in the production and purification processes and novelty and advantages of the recombinant, modified chitinase comprising Novel purification protocol by chitin adsorption affinity chromatography using powdered crustacean shells making the large scale purification strategy simple and cost-effective (example 3).

The recombinant, modified chitinase enzyme is thermoactive (optimum pH 55-60° C.) thermostable (66.7° C.) (FIG. 11 from the description of drawings) active over a broad range of pH (3.0-11.0) with a pH optimum of 9.0, suitable for several commercial biotechnology applications like bioremediation, biorefinery, where the industrial operations use highly stable, enzyme that can withstand harsh industrial environment, proving that its truly an industrial chitinase (example 8, 9 and 10).

The recombinant, modified enzyme exhibits dual enzyme activity (both exo- and endochitinase activity) is a very important feature which can make it a more efficacious biocontrol agent with enhanced biocontrol potential against insect pests and phytopathogenic fungi (example 10).

Substitution of tyrosine with histidine results in improved solubility which improves the amphipathic nature and physiological action of the chitinase, while acting on the chitin in the cuticle and pore formation in the chitin-lined midgut of the larvae to enhance the membrane permeability and allow the toxins to permeate through (example 6).

Contact bioassays followed by the SEM and histopathological studies have demonstrated insecticidal knockdown which results in mortality of the target insects in 48 h. The recombinant, modified chitinase from *Brevibacillus laterosporus* Lak 1210 can be developed into a novel, contact biopesticide due to its mode of action on the insect cuticle by the novel enzyme-based technology (example 11 and 12).

Contact insect bioassays have also demonstrated that the modification of protein helps the enzyme better to penetrate the insect cuticle has resulted in increased efficacy for degrading the cuticle during molting, resulting in the death of larvae and also delay in adult emergence (Example 17).

BRIEF DESCRIPTION OF DRAWINGS

This application contains at least one drawing executed in color. Copies of this patent application publication with color drawing(s) will be provided by the Office upon request and payment of the necessary fee.

FIG. 1: PCR amplification of BRLA_Chi 90 gene from *Brevibacillus laterosporus* Lak 1210 Lane 1-DNA marker-1 Kb ladder and Lane 2-2583 bp PCR product of Blchi gene.

FIG. 2A: SDS-PAGE analysis of recombinant, modified BRLA_Chi 90 from *Brevibacillus laterosporus* Lak 1210:

M-Protein marker, 1. lysate, 2. periplasmic fraction 3. culture supernatant 4. soluble fraction, 5. insoluble fraction, 6 and 7. chitinase fractions.

Figure 2A:
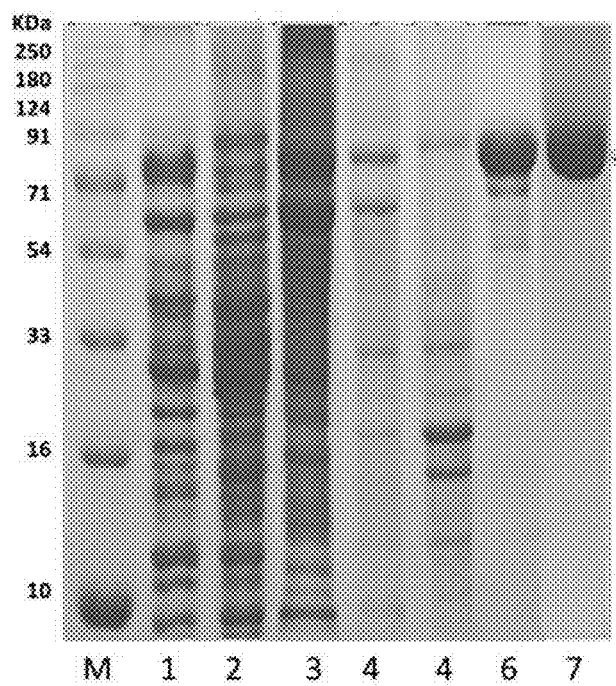
Figure 2B:
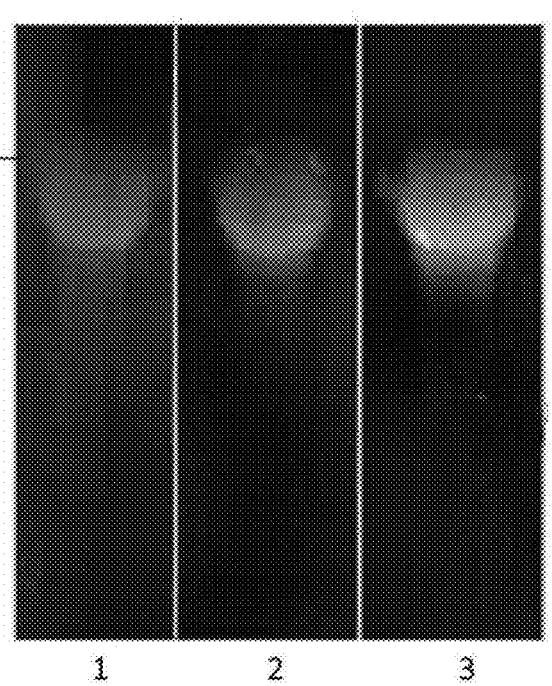

FIG. 2B. Chitinase zymography with 4-Methylumbelliferyl substrates using recombinant, modified BRLA_Chi 90 from Brevibacillus laterosporus Lak 1210: 1. N-acetylglucosaminide 2.4 MU-chitobioside 3.4 MU-chitotrioside). The numbers on the left dictate the molecular masses (in kilodaltons) of the protein standards. The positions of the purified chitinase fraction is indicated by arrows.

FIG. 3: Secretion profile of recombinant, modified chitinase BRLA_Chi 90 from *Brevibacillus laterosporus* Lak 1210 expressed in the different cell compartments—samples of the extracellular medium (■) periplasm (•) in the cytoplasm (▲) from 24-h time points of *E. coli* BL 21 (DE3). The β-galactosidase activity detected in the culture medium (♦) was used as an indicator of cell lysis. The culture was grown at 37° C. until $OD_{600}$ reached 0.8, induced with 0.1 mM IPTG and incubated for another 24 h. All experiments were evaluated under identical conditions and performed in triplicate.

FIG. 4: Multiple sequence alignment comparison of the 90 kDa recombinant, modified chitinase, BRLA_Chi 90 from *Brevibacillus laterosporus* Lak 1210 with the conserved domains of chitinases from entomopathogens.

FIG. 5: Multiple sequence alignment comparison of the 90 kDa recombinant, modified chitinase BRLA_Chi 90 of from *Brevibacillus. laterosporus* Lak 1210 with the conserved domains of chitinases from other bacterial chitinases.

FIG. 6: MALDI-TOF/MS spectrum of purified recombinant, modified BRLA_Chi 90 from *Brevibacillus laterosporus* Lak 1210. The molecular mass of the enzyme was 89680 Da.

FIG. 7: Optimum temperature profile of recombinant, modified chitinase, BRLA_Chi 90 from *Brevibacillus laterosporus* Lak 1210. Assay conditions-Assay buffer-sodium acetate (pH 5.0), reaction volume (100 μl) substrate concentration (10 μM), enzyme concentration (0.1 μg).

FIG. 8: Optimum pH profile of recombinant chitinase, BRLA_Chi 90 from *Brevibacillus laterosporus* Lak 1210.

Assay conditions—buffer systems used were citrate buffer (50 mM, pH 3.0-4.0), acetate (50 mM, pH 4.0-5.0), phosphate (50 mM, pH 6.0-8.0), Tris HCl (50 mM 8.0-9.0) and carbonate-bicarbonate (50 mM, pH 9.0-11.0), reaction volume (100 μl) substrate concentration (10 μM), enzyme concentration (0.1 μg).

FIG. 9: CD spectrum of recombinant, modified BRLA_Chi 90 from *Brevibacillus laterosporus* Lak 1210 showing secondary structure with 20.47% alpha helix, 27.09% beta sheets, 11.57% turns and 40.93% coils.

FIG. 10: CD spectrum of thermal unfolding of recombinant, modified chitinase, BRLA_Chi 90 from *Brevibacillus laterosporus* Lak 1210.

FIG. 11: Mass spectroscopic analysis-using electrospray ionization mass spectrometry (ESI-MS) of chitooligosaccharides standards showing their masses GlcNAc (244.11), $GlcNAc_2$(447.23) $GlcNAc_3$(650.30), $GlcNAc_4$(853.35), $GlcNAc_5$(1056.38) and $GlcNAc_6$(1259.4).

FIG. 12: ESI-MS profile for time course analysis of chitin hydrolysis using recombinant, modified BRLA_Chi 90 from *Brevibacillus laterosporus* Lak 1210 (20 min).

Reaction conditions: Substrate (colloidal chitin) 10 mg/ml, purified chitinase 100 μg, reaction volume—100 μl, reaction buffer—50 mM sodium acetate (pH 5.0).

Chitooligomers obtained from colloidal chitin after digestion (20 min) depicted two peaks corresponding to $GlcNAc_3$ (m/z 650.83) a sodium adducts of three NAG molecules (chitotriose) and $GlcNAc_2$ (m/z 447.2), a sodium adducts of two NAG molecules (chitobiose).

FIG. 13: ESI-MS profile for time course analysis of chitin hydrolysis using recombinant, modified BRLA_Chi 90 from *Brevibacillus laterosporus* Lak 1210 (1 h).

Reaction conditions: Substrate (colloidal chitin) 10 mg/ml, purified chitinase 100 μg, reaction volume—100 μl, reaction buffer—50 mM sodium acetate (pH 5.0).

Intensity of $GlcNAc_2$ increased with time. Apparently, $GlCNAc_3$ was also cleaved to form $GlcNAc_2$.

FIG. 14: ESI-MS profile for time course analysis of chitin hydrolysis using recombinant, modified BRLA_Chi 90 from *Brevibacillus laterosporus* Lak 1210 (3 h).

Reaction conditions: Substrate (colloidal chitin) 10 mg/ml, purified chitinase 100 μg, reaction volume—100 μl, reaction buffer—50 mM sodium acetate (pH 5.0).

After 3 h, the product is predominantly $GlCNAc_2$. No higher oligomers detected.

FIG. 15: ESI-MS profile for time course analysis of chitin hydrolysis (6 h) using recombinant, modified BRLA_Chi 90 from *Brevibacillus laterosporus* Lak 1210.

Reaction conditions: Substrate (colloidal chitin) 10 mg/ml, purified chitinase 100 μg, reaction volume—100 μl, reaction buffer—50 mM sodium acetate (pH 5.0).

Chitooligomers obtained from colloidal chitin after digestion (6 h) $GlcNAc_3$ (m/z 650.83) sodium adducts of three NAG molecules (chitotriose) and $GlcNAc_2$ (m/z 447.25), a sodium adducts of two NAG molecules (chitobiose).

FIG. 16: ESI-MS profile for time course analysis of chitin hydrolysis (12 h) using recombinant, modified BRLA_Chi 90 from *Brevibacillus laterosporus* Lak 1210.

Reaction conditions: Substrate (colloidal chitin) 10 mg/ml, purified chitinase 100 μg, reaction volume—100 μl, reaction buffer—50 mM sodium acetate (pH 5.0).

Chitooligomers obtained from colloidal chitin after digestion (12 h), only $GlcNAc_2$ (m/z 447.25), a sodium adduct of two NAG molecules (chitobiose) was detected FIG. 17: ESI-MS profile for time course analysis of chitin hydrolysis (24 h) using recombinant, modified BRLA_Chi 90 from *Brevibacillus laterosporus* Lak 1210.

Reaction conditions: Substrate (colloidal chitin) 10 mg/ml, purified chitinase 100 μg, reaction volume—100 μl, reaction buffer—50 mM sodium acetate (pH 5.0).

Chitooligomers obtained from colloidal chitin after digestion (24 h) and N-acetylglucosamine (m/z 226.86) was also a major product along with the $GlcNAc_2$ (m/z 447.25), a sodium adducts of two NAG molecules (chitobiose).

FIG. 18: ESI-MS profile for time course analysis of chitin hydrolysis (48 h) using recombinant, modified BRLA_Chi 90 from *Brevibacillus laterosporus* Lak 1210.

Reaction conditions: Substrate (colloidal chitin) 10 mg/ml, purified chitinase 100 μg, reaction volume—100 μl, reaction buffer—50 mM sodium acetate (pH 5.0).

Chitooligomers obtained from colloidal chitin after digestion (48 h) and N-acetylglucosamine (m/z 226.86) was predominantly detected along with the chitobiose (m/z 447.25) indicating that the chitobiose was cleaved to give N-acetylglucosamine as the final product of chitin hydrolysis.

FIG. 19A: Scanning Electron Microscopy (SEM) study of hydrolytic effects of the recombinant, modified chitinase BRLA_Chi 90, on an untreated cuticle of *Spodoptera litura* (topical bioassays); FIG. 19B: SEM study of hydrolytic effects of the recombinant, modified chitinase BRLA_Chi 90, on a treated cuticle (12 h) of *Spodoptera litura* (topical bioassays);

FIG. 19C: SEM study of hydrolytic effects of the recombinant, modified chitinase BRLA_Chi 90, on a treated cuticle (24 h) of *Spodoptera litura* (topical bioassays).

Figure 20A:
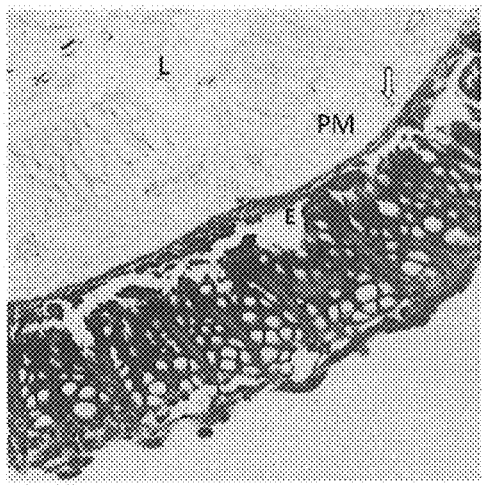

FIG. 20A: Histopathological study showing ultrastructural changes in the untreated midgut (control) of *Spodoptera litura* following droplet feeding insect bioassays in which the larvae were orally fed with recombinant, modified chitinase, BRLA_Chi 90 from *Brevibacillus laterosporus* Lak 1210; FIG. 20B: Histopathological study showing ultrastructural changes in the treated midgut (48 h) of *Spodoptera litura* following droplet feeding insect bioassays in which the larvae were orally fed with recombinant, modified chitinase, BRLA_Chi 90 from *Brevibacillus laterosporus* Lak 1210.

FIG. 21: Antifungal activity of recombinant, modified chitinase, BRLA_Chi 90 from *Brevibacillus laterosporus* Lak 1210 against *Fusarium oxysporum* (hyphal extension inhibition assay).

FIG. 22A: Scanning Electron Microscopy (SEM) study of hyphal morphology (untreated hyphae) of *Fusarium oxysporum* treated with recombinant, modified chitinase, BRLA_Chi 90 from *Brevibacillus laterosporus* Lak 1210; FIG. 22B: SEM study of hyphal morphology (treated hyphae, 6 h) of *Fusarium oxysporum* treated with recombinant, modified chitinase, BRLA_Chi 90 from *Brevibacillus laterosporus* Lak 1210.

FIGS. 23A-23D: Localization of FITC-BRLA_Chi 90 from *Brevibacillus laterosporus* Lak 1210 in the hyphae of *Fusarium oxysporum*. Hyphae were identified based on the differential interference contrast (DIC) image. Subsequently, the localization of the GFP signal was scored in at least 100 hyphae. FIG. 23A: Localization of FITC-labelled recombinant chitinase BRLA_Chi 90 at the septa. FIG. 23B: Localization of FITC-labelled chitinase in the cortex of mature hypha FIG. 23C: Localization of FITC-labelled recombinant chitinase on the cell wall FIG. 23D: Localization of FITC-labelled recombinant chitinase at the hyphal tip.

FIGS. 24A and 24B: Fluorescence microscopy study to evaluate localization of FITC-BRLA_Chi 90 from *Brevibacillus laterosporus* Lak 1210, in the hyphae of *Fusarium oxysporum*. FIG. 24A: Swelling of hyphal tip. FIG. 24B: Complete destruction of the hypha.

FIGS. 25A and 25B: Bright field photomicrographs of histology of heart in rats (40×, H & E stain) FIG. 25A: Control treated with sterile PBS. FIG. 25B: Test treated with 20 mg/kg of purified chitinase from *Brevibacillus laterosporus* Lak 1210.

FIGS. 26A and 26B: Bright field photomicrographs of histology of kidney in rats (40×, H & E stain) FIG. 26A: Control treated with sterile PBS. FIG. 26B: Test treated with 20 mg/kg of purified recombinant, modified chitinase BRLA_Chi 90 from *Brevibacillus laterosporus* Lak 1210.

FIGS. 27A and 27B: Bright field photomicrographs of histology of liver in rats (40×, H & E stain) FIG. 27A: Control treated with sterile PBS, FIG. 27B: Test treated with 20 mg/kg of purified recombinant chitinase BRLA_Chi 90 from *Brevibacillus laterosporus* Lak 1210.

FIGS. 28A and 28B: Bright field photomicrographs of histology of lungs in rats (40×, H & E stain) FIG. 28A: Control treated with sterile PBS, FIG. 28B: Test treated with 20 mg/kg of purified recombinant chitinase BRLA_Chi 90 from *Brevibacillus laterosporus* Lak 1210.

FIGS. 29A and 29B: Bright field photomicrographs of histology of spleen in rats (40×, H & E stain) FIG. 29A: Control treated with sterile PB S, FIG. 29B: Test treated with 20 mg/kg of purified recombinant chitinase BRLA_Chi 90 from *Brevibacillus laterosporus* Lak 1210.

FIG. 30: Protein structure-function prediction of the substitution site of the modified recombinant chitinase enzyme from *Brevibacillus laterosporus* Lak 1210.

DETAILED DESCRIPTION OF THE INVENTION

Development of bioinsecticides for use against insects has generally been limited to *Bacillus thuringiensis* and majority of the patents in insect control are based on cry toxins of *Bacillus thuringiensis*. The knowledge base on enzyme-based biological control is very little and it needs increased scientific space in entomological and biotechnological research. The scope of the invention is to develop a novel chitinase enzyme for controlling key insect pests and fungal diseases of importance agriculturally important crops, fruit and vegetable crops, natural forests and forest plantations and other industrial applications. Strong contact toxicity through topical application of the novel chitinase from the strain of *Brevibacillus laterosporus* Lak 1210 has proved that it is toxic to the insect upon direct contact and may result in quick kill.

Nucleic acids described herein as "isolated" are nucleic acids that have been obtained from their natural source or separated from the genomic DNA using biological and/or and chemical methods. Nucleic acids described herein as "recombinant" are nucleic acids or fragments or variants thereof which have been generated by molecular techniques such as PCR, including conventional PCR, overlap extension PCR-mediated site-directed mutagenesis that alter or extend the gene coding sequence by virtue of substitution of one or more nucleotides in the oligonucleotides utilized in the PCR amplification and/or cloning into an expression vector using restriction enzymes. As described herein, "active form" means chemically active and capable of hydrolysing and or solubilizing chitinous substrates and "biologically active" means capable of controlling insects and inhibiting phytopathogenic fungi.

In an embodiment of the present invention, an isolated nucleic acid sequence set forth in SEQUENCE ID NO:1 encoding chitinase having the amino acid sequence set forth in SEQUENCE ID NO:2 from *Brevibacillus laterosporus* Lak 1210 deposited under MTCC Accession No. 5487 is disclosed. The SEQUENCE ID NO:2 from position 1 to 42 is a secretory signal peptide encoded by a sequence set forth in SEQUENCE ID NO:6. The signal peptide sequence has the amino acid sequence as set forth in SEQUENCE ID NO:40: MRKMYQHIPTAHSVRKFNFLLLAFVLFAS-IFPAILPASVSAS. The signal peptide sequence derived from the chitinase gene of the strain of *Brevibacillus laterosporus* Lak 1210 has been found to function as a strong secretion signal when fused to gene sequences of the expression vector pET 21b to construct a recombinant expression plasmid, pET/BLRA_Chi90 and expressed in the host cells. The signal peptide, when fused to gene sequences and expressed as a polypeptide, localize the recombinant protein as periplasmic, cytoplasmic fractions and also secreted from the cell and recovered from the extracellular medium. The native secretory signal sequence of BLRA_Chi 90 gene of SEQUENCE ID NO: 6 can be linked to foreign DNA for secreted expression of the recombinant protein from other organisms. The nucleotide sequences for the native chitinase were deposited with the GenBank with the accession number MF397932.

The present invention also includes a recombinant nucleic acid sequence as set forth in SEQUENCE ID NO:3 from *Brevibacillus laterosporus* Lak 1210 encoding recombinant chitinase having an amino acid sequence set forth in SEQUENCE ID: 0.4 or SEQUENCE ID: 5. The nucleotide sequences for the recombinant (mutated) chitinase sequence were deposited with the GenBank with the accession numbers MF 397933. Particular embodiments of the invention further provide isolated biocidal (e.g., insecticidal activity and antifungal activity) polypeptides encoded by either a full length native or recombinant nucleic acid of the embodiments. In particular examples, biocidal proteins of the embodiments include fragments of full-length proteins and polypeptides that are produced from mutagenized nucleotide sequence designed to introduce one or more nucleotide residues that is not present in the corresponding native sequence. The embodiments further provide mutant nucleotide sequence which confer improved or altered properties on the polypeptides of the embodiments to accomplish the object of mutation, for example, an enhanced insecticidal activity, antifungal activity and chitin hydrolyzing activity The recombinant nucleic acid with a nucleotide sequence (SEQUENCE ID NO:3) further encodes truncated polypeptide sequences having SEQUENCE ID NO:7 to SEQUENCE ID NO:39 as shown in Table 1 below:

TABLE 1

Listing of unique peptides from peptide mass fingerprinting of recombinant, modified BLRA_Chi_90 (SEQUENCE ID NO: 7-SEQUENCE ID NO: 39)

| SEQUENCE ID | PROTEIN SEQUENCE |
| --- | --- |
| SEQ ID NO: 7 | IEVTGFQLGDQNYPINPTLK |
| SEQ ID NO: 8 | NYDSTLVAPWLWNAEK |
| SEQ ID NO: 9 | NLTHINYAFAHVDSNNR |
| SEQ ID NO: 10 | VFLSTEDEQSIGAK |
| SEQ ID NO: 11 | AKDNQGLESEASQPLK |
| SEQ ID NO: 12 | DNQGLESEASQPLK |
| SEQ ID NO: 13 | GFQNVVGGTDGLWGK |
| SEQ ID NO: 14 | DENGKEEGAGSNPMWHAK |
| SEQ ID NO: 15 | NDGKGEYYMGSTLTK |
| SEQ ID NO: 16 | DHGIVNPVLTGTYK |
| SEQ ID NO: 17 | GHFNLLTQWK |
| SEQ ID NO: 18 | DENGKEEGAGSNPMWHAK |
| SEQ ID NO: 19 | EEGAGSNPMWHAK |
| SEQ ID NO: 20 | YYMLTIASPSSAYLLR |
| SEQ ID NO: 21 | LDQASAEDEK |
| SEQ ID NO: 22 | GEYYMGSTLTK |
| SEQ ID NO: 23 | NDGKGEYYMGSTLTK |
| SEQ ID NO: 24 | IISAGHTGPNVGGLK |
| SEQ ID NO: 25 | GEYYMGSTLTK |
| SEQ ID NO: 26 | GLMEGYNALLK |
| SEQ ID NO: 27 | EEGAGSNPMWHAK |
| SEQ ID NO: 28 | GMESFQALK |
| SEQ ID NO: 29 | TIYTSGQQASYK |

TABLE 1-continued

Listing of unique peptides from peptide mass fingerprinting of recombinant, modified BLRA_Chi_90 (SEQUENCE ID NO: 7-SEQUENCE ID NO: 39)

| SEQUENCE ID | PROTEIN SEQUENCE |
| --- | --- |
| SEQ ID NO: 30 | GLMEGYNALLK |
| SEQ ID NO: 31 | YLVTDIPWK |
| SEQ ID NO: 32 | IIGYFTSWR |
| SEQ ID NO: 33 | GMESFQALK |
| SEQ ID NO: 34 | INIGVPYYTR |
| SEQ ID NO: 35 | VTTDTDTLPPEPATPCRPAGLYDSGV |
| SEQ ID NO: 36 | VAVTIPTWK |
| SEQ ID NO: 37 | GHEWTAK |
| SEQ ID NO: 38 | KYAVTDK |
| SEQ ID NO: 39 | VKLDQASAEDEK |

In an aspect, SEQ ID NO:3 is a mutated sequence set forth in an isolated nucleic acid sequence set forth in SEQ ID NO:1. CATATG is the restriction site for the restriction enzyme Nde 1, the native chitinase sequence can be cut by the restriction enzyme Nde 1 at two places. To facilitate the cloning of complete ORF and ensure the translation of the ORF into a functional protein, single point mutations have been incorporated by site directed mutagenesis at the positions 661 and 2158 to replace the nucleotide 'T' with the nucleotide 'C'. The CATATG in the ORF of the native sequence has been changed to CACATG. The recombinant (mutated) sequence ORF has the sequence CACATG. Though the base 'T' is replaced with 'C' since both the codons, CAT and CAC code for the same amino acid, Histidine, and hence there is no change in the functionality of the protein.

The site directed mutagenesis resulted in the substitution of a polar, hydrophilic histidine (H) residue for a hydrophobic aromatic amino acid tyrosine (Y) at positions 221 and 720 in the SEQUENCE NO. 4 and SEQUENCE NO. 5. The amino acid substitution may increase the interaction with the negatively charges insect cuticle. The increase in positive charge is crucial for binding negatively charged insect cuticle and subsequently move into the aqueous haemolyph and continue to induce cell lysis, resulting in the death of the target insect. Histidine is interesting in that it is an ideal residue for protein functional centers, most common amino acid in protein active or binding site, with a pKa near that of physiological pH. The variation in peptide sequence should be possible without losing its biological activity. Substitution of tyrosine with histidine did not affect the amphipathic nature and physiological action of the protein while acting on the chitin the cuticle and pore formation in the chitin-lined midgut region to enhance the membrane permeability and allow the toxins to permeate through.

Contact insect bioassays have demonstrated that the modification of protein to better penetrate the insect cuticle has resulted in increased efficacy for degrading the cuticle during molting, resulting in the death of larvae and also delay in adult emergence.

Soluble proteins tend to have polar or hydrophilic residues on their surfaces. The aminoacid substitution at position 221 replacing tyrosine with histidine resulted in improved solubility of the protein, another important desirable characteristic feature that enhances the efficacy of a biocontrol agent/biopesticide and is much suitable for various industrial applications of chitinase.

In an aspect of the present invention, a DNA construct including the isolated nucleic acid sequence set forth in SEQUENCE ID NO:1 encoding native chitinase having the amino acid sequence set forth in SEQUENCE ID NO:2 from *Brevibacillus laterosporus* Lak 1210 deposited under MTCC Accession No. 5487 is provided. In another aspect of the present invention, a DNA construct including the recombinant nucleic acid sequence as set forth in SEQUENCE ID NO:3 from *Brevibacillus laterosporus* Lak 1210 encoding recombinant, modified chitinase having amino acid sequence set forth in SEQUENCE ID NO:4 or SEQUENCE ID NO 5 is provided.

In a further aspect, an expression vector including the DNA construct having the recombinant nucleic acid sequence as set forth in SEQUENCE ID NO:3 from *Brevibacillus laterosporus* Lak 1210 encoding recombinant chitinase having amino acid sequence set forth in SEQUENCE ID NO:4 or SEQUENCE ID NO 5 is provided. The expression vector includes the recombinant nucleic acid sequence set forth in SEQUENCE ID NO:3 from *Brevibacillus laterosporus* Lak 1210 encoding chitinase having the amino acid sequence set forth in SEQUENCE ID NO:4 or SEQUENCE ID NO:5, operably linked with T7 promoter and a native regulator sequence set forth in SEQUENCE ID NO: 6. The expression vector carrying the isolated nucleic acid sequence (SEQUENCE ID No 1) or recombinant nucleic acid sequence (SEQUENCE ID NO 3) designated as pET/BRLA_Chi90.

Truncated polypeptides of SEQUENCE ID No: 7 to SEQUENCE ID No: 39 encoded by the polynucleotide fragments of the embodiments are characterized by insecticidal and antifungal activity that is either equivalent to, or improved, relative to the activity of the corresponding full-length polypeptide of SEQUENCE ID No: 2, SEQUENCE ID No: 4 and SEQUENCE ID No 5 encoded by the nucleic acid sequence of SEQUENCE ID No: 1 and 3 from which the fragment is derived.

Generally, purification of chitinolytic enzymes is a multistep process exploiting a range of biophysical and biochemical characteristics such as its relative concentration in the source, solubility, charge, size (molecular weight), hydrophobicity/hydrophilicity of the target protein. In general, purification strategy is focused on high yield and recovery, purity of the enzyme, reproducibility of the method, economical use of the chemicals and reagents and shorter time for complete purification.

In an aspect, the present invention provides a single step purification method by chitin affinity chromatography. The soluble, active recombinant, modified chitinase BRLA_Chi 90 from the extracellular milieu of *E. coli* can be purified by a single step, large scale, cost-effective chitin adsorption affinity purification method using colloidal chitin or fishery waste from sea food processing industry like crustacean shells (crab shells, shrimp shells and krill shells). The recombinant, modified chitinase of the present invention can be biologically pure and can have a molecular weight of 89.68 kDa determined by SDS-PAGE and MALDI-TOF (FIG. 2A). The aminoacid sequence of the recombinant chitinase expressed as a mature protein (without signal peptide) was listed as SEQUENCE ID NO: 5.

Based on the cleavage pattern, chitinases have been classified into two broad categories i.e. endochitinases and exochitinases. Endochitinases (EC 3.2.1.14) randomly cleave β-1,4-glycosidic bonds of chitin polymer to produce oligomers of different length which can be converted into mixtures of dimers (diacetylchitobiose) and monomeric units (N-acetylglocosamine). Exochitinases are divided into two subcategories based on the type of the product released: exo-N,N'-diacetylchitobiohydrolases, also designated as chitobiosidases (EC 3.2.1.29) which catalyze the progressive release of the dimer, diacetylchitobiose (GlcNAc2) from the non-reducing end of the chitin and β-1-4 N-acetyl-D-glucosaminidase (EC 3.2.1.30) which cleave the oligomeric products of endochitinases and chitobiosidases, typically chitobioses generating N-acetylglucosamine. They hydrolyze $GlcNAc_2$ into GlcNAc or produce GlcNAc from the nonreducing end of the chitooligomers. In addition, exo-N,N',N''-acetylchitotriohydrolases cleave monomeric units of GlcNAc from longer chitin chain or release chitotriose which is subsequently cleaved to form diacetylchitobiose and N-acetylglucosamine (Brurberg M. B, Nesl I. F and Eijsink, V. G. H (1996) *Comparative studies of chitinases A and B from Serratia marcescens Microbiol.* 142: 1581-1589).

Generally, the chitinases known in the art show either endochitinase activity or exochitinase activity. The recombinant chitinase enzyme of the present invention exhibits the exochitinase activity and endochitinase activity. Fluorogenic assays showed that the recombinant, modified chitinase enzyme of the present invention, BRLA_Chi 90 exhibits two types of major exochitinase activity, predominantly a chitobiosidase activity and also a prevalent N-acetylglucosaminidase activity, with some endochitnase activity. Chitinase activity assays using the three types of fluorogenic substrates-, 4-MU-β-D-N, N,N''-triacetylchitotriose, 4-MU-diacetyl-β-D-chitobioside and 4-MU-N-acetyl-β-D-glucosaminide, showed that the recombinant, modified chitinase enzyme exhibits endochitinase activity, exo-N,N'-diacetylchitobiohydrolase activity and also β-N-acetyl-D-glucosaminidase activity.

Zymography analyses and real time ESI-MS studies also confirmed that the recombinant modified chitinase BRLA_Chi 90 is a unique, chitinolytic enzyme with dual enzyme activity, both exo and endochitinase activity. The combined endo- and exo-chitinase activity results in a synergistic increase in the chitinolytic activity resulting in a greater efficacy of chitinase for insect control and efficient chitin degradation. Analysis of chitin hydrolysis using colloidal chitin, an insoluble chitin substrate, indicates that the recombinant chitinase enzyme can also be capable of producing monomers from longer chitin chain, indicating that they also have an endochitinase or exo-N,N',N''-triacetylchitotriohydrolase activity. While exo- and endochitinases are able to hydrolyze chitin independently to yield chitooligomers of different length, the presence of both activities significantly enhances the efficiency of chitinolytic machinery. The recombinant chitinase enzyme of the present invention exhibits both the exochitinase activity and endochitinase activity at a temperature from 25° C. to 67° C., a novel and most important desirable feature which makes it suitable for various commercial applications in agriculture, medicine and environment.

As demonstrated by most sensitive, reliable ESI-MS experiments, the recombinant, modified chitinase, BRLA_Chi 90 exhibits exo- and endochitinase activity to completely degrade the chitin to yield chitobiose and N-acetylglucosamine, as major products. The ability of BRLA Chi 90 to act on insoluble chitin substrate (colloidal chitin) strongly indicates that it is a "true chitinase" and not a chitodextrinase. The recombinant chitinase is suitable for many industrial applications, in particular, it could completely utilize naturally occuring, cheap, abundant sources of chitin wastes from the environment like crustacean shells to yield value added chemicals, biofuels and biopolymers.

Though the recombinant, modified chitinase exhibits sequence homology with two other proteins, chitodextrinase from *Brevibacillus laterosporus* GI-9 (Genbank Accssion No-CCF12514.1) and a chitodextrinase from *Brevibacillus laterosporus* LMG 15411(Genbank Accession No-WP 003335299.1), it doesn't exhibit any functional homology with these proteins.

Chitodextrinase processively hydrolyzes disaccharides from the non-reducing end of soluble chitin oligosaccharides and is not active on chitin. The chitodextrinase from *Brevibacillus laterosporus* GI-9 and *Brevibacillus laterosporus* LMG 15411, is an endo-cleaving chitodextrinase acts only on soluble chitoligosaccharide substrates and it has no activity on insoluble chitin substrates. Irrespective the source of organism, the enzyme chitodextrinase doesn't solubilise insoluble forms of chitin like crystalline chitin (chitin flakes), amorphous chitin (colloidal chitin), it will only act on soluble chitooligomers, whereas, a true chitinase will act on native chitin and completely degrade it to monomer, N-acetylglucosamine. Two proteins with similar sequence homology can be functionally different and have different biological activity and mode of action.

Figure 7:
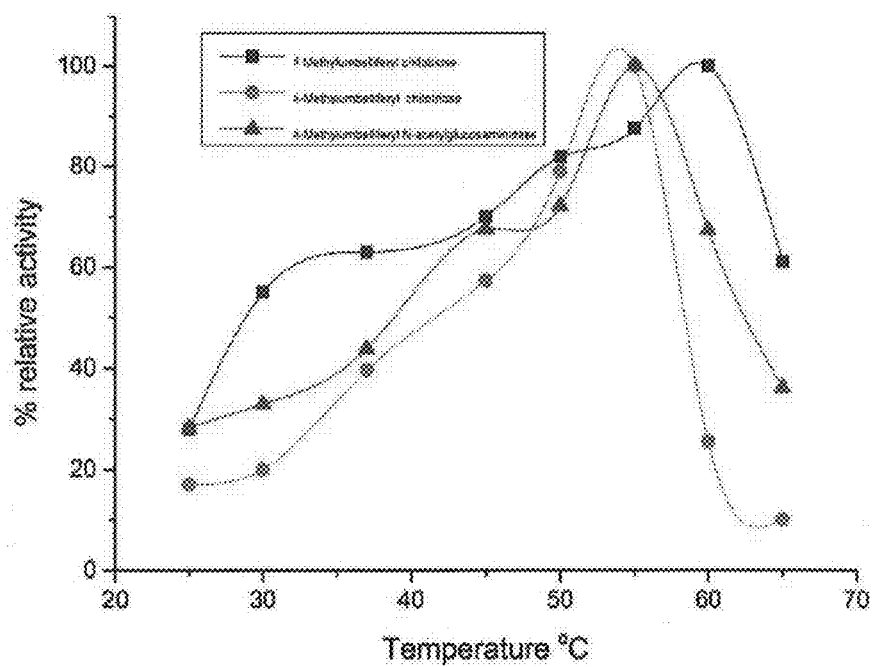

FIG. 7 shows the temperature profile of the recombinant chitinase of the present invention. Further, fluorogenic assays revealed that the recombinant chitinase BRLA_Chi 90 of the present invention exhibits an as endochitinase activity and an exochitinase activity (β-1, 4-N-acetylglucosaminidase activity and/or N, N', N"-triacetylchitotriohydrolase activity) at an optimum temperature of 55° C. and an exochitinase activity, exo-N, N'-diacetylchitobiohydrolase activity) at an optimum temperature of 60° C.

The optimal pH for the recombinant chitinase BRLA_Chi 90 was determined by assaying the purified enzyme at different pH (3.0-11.0) using appropriate buffers and measuring the relative activity under standard assay conditions using fluorogenic 4-methylumbelliferyl substrates. The desirable physicochemical features of the recombinant chitinase BRLA_Chi 90 includes its activity at a broad range of pH (3.0-11.0) and an optimum pH—9.0, indicating that it is alkaline active enzyme, a desirable feature suitable for insect control and industrial processing of chitin.

The chitinase enzyme based biological control using novel, chitinase compositions of the present invention from a new strain of entomopathogen, *Brevibacillus laterosporus* Lak 1210, as a potential, contact biopesticide. This aspect of the invention may lead to the development of a novel, contact insecticidal compositions having the recombinant chitinase, BRLA_Chi 90, as an alternative to Bt-based biopesticide, since Bt is effective only when eaten by the insect as a larva. The present invention will majorly focus on its successful use as contact biopesticide with substantially reduced requirement of frequent application, unlike the other biopesticides, which need frequent field application.

In an embodiment of the present invention, a composition having the recombinant chitinase enzyme of the present invention and a carrier is provided. Preferred combinations can be formulated with an acceptable carrier into a biopesticide/biocontrol agent. Furthermore, these combinations of this invention have an advantage of being formulated as an adjuvant, a colloid, a wettable powder, an emulsifiable concentrate, an aerosol or spray, a dusting powder, a dispersible granule or pellet, an impregnated granule, a suspension, a solution, an emulsion and also microencapsulations. The compositions can be formulated by conventional methods such as those described in, for example, Winnacker-Kuchler (1986), "*Chemische Technologie*" [*Chemical Technology*], Vol. 7, C. Mauser Verlag Munich, 4th Ed. 1986; van Valkenburg, "*Pesticide formulations*", Marcel Dekker N. Y., 2nd Edition 1972-73; K Martens, "*Spray Drying Handbook*", 3rd Edition, G. Goodwin Ltd. London. Necessary formulation aids include carriers, inert materials, surfactants, solvents, and other additives. Such formulated compositions may be prepared by concentration of a culture of cells having the polypeptides by methods like desiccation, extraction, filtration, centrifugation, sedimentation, homogenization and lyophilization.

The composition of the present invention can be a contact biopesticide, ingestion biopesticide, biofungicide, bioinsecticide, or a bionematicide. In certain exemplary embodiments, insecticidal and antifungal compositions for enzyme-based formulations containing the recombinant, modified chitinase, BRLA_Chi 90 are provided. Specific embodiments also provide screening of different classes of compositions or formulations based on the determined and desired characteristics of the recombinant, modified chitinolytic enzyme, BRLA_Chi 90. The antifungal and insecticidal compositions can include culture supernatant containing the secreted recombinant, modified chitinase, BRLA_Chi 90 and/or culture broth containing the whole cells of recombinant *E. coli* carrying the expression vector pET/BRLA_Chi90. The insecticidal and antifungal compositions can be formulated as dry formulations (wettable powders, dry flowables, dust, granules) or b) liquid formulations (oil-based, aqueous-based) or combinations thereof. For liquid compositions, the antifungal and insecticidal compositions including recombinant, modified chitinase, BRLA_Chi 90 can be blended with mineral or vegetable-based oil carrier and emulsifiers or stabilizers, stickers, surfactants and antifreeze compounds. Dry compositions or formulations can include an inert carrier (peat, vermiculite etc) or chitin and chitosan materials or natural chitinous sources like crustacean shells. The antifungal and insecticidal compositions can also be formulated as controlled release formulations (nanoformulations based on nanomaterials or microencapsulated formulations using microencapsulation technologies).

The present invention is also directed to a method of protecting or treating or modulating phytopathogenic infection in a plant or a part thereof including applying a composition as disclosed. The phytopathogenic infection in a plant can be caused by a fungi or an insect. An effective amount of the compositions of the present invention can be applied to the environment hosting the target insect pest/ pathogenic fungus, e.g., soil, water or a plant or a part thereof wherein seeds, plantules, plants, foliage of plants of the plant to treat the infection.

More specifically, exemplary embodiments provided methods for utilizing nucleotide sequences and their encoding polypeptides with insecticidal and antifungal activity produced by the recombinant microorganisms and also methods and compositions of chitinase enzyme-based formulations for impacting insect pests and phytopathogenic fungi.

The phytopathogenic infection as described in the present invention is a plant disease caused by at least one fungus selected from the group consisting of *Fusarium, Rhizoctonia, Pythium, Phytophthora, Cercospora, Puccinia, Venturia, Alternaria, Uncinula, Ustilago, Colletotrichum, Erysiphe, Botrytis, Sclerotium* and *Monilinia* which comprises contacting such fungus with purified antifungal chitinases effective to obtain said inhibiting. The method of the present invention involving application of a chitinolytic enzyme can be carried out through a variety of procedures when all or part of the plant is treated, including seeds, roots, stems and leaves etc.

The examples of the *Fusarium* species include *Fusarium oxysporum, Fusarium lycopersici, Fusarium moniliforme, Fusarium graminearum* and *Fusarium equiseti*.

The active compounds and compositions of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Diptera, Lepidoptera, Coleoptera, Hymenoptera, Homoptera, Hemiptera, Orthoptera, Thysanoptera, Isoptera, more specifically insects from Diptera, Coleoptera and Lepidoptera. Further, the phytopathogenic infection as described in the present invention may be caused by at least one insect belonging to Lepidoptera, Diptera, Coleoptera, Homoptera or Hymenoptera. In a preferred embodiment of the present invention there is provided a method for protecting or treating or modulating phytopathogenic infection in plant or a part thereof, wherein the method comprises applying the composition as disclosed in the present invention as a contact biopesticide. In another embodiment, there is provided a method for protecting or treating or modulating phytopathogenic infection in plant or a part thereof, wherein the method comprises applying the composition as disclosed in the present invention as an ingestion biopesticide in an effective amount. The ingestion biopesticide can be applied in an effective amount to damage the midgut in said insect larvae and insects.

In another embodiment of the present invention there is provided a method for protecting or treating or modulating phytopathogenic infection in plant or a part thereof, wherein the method comprises applying the composition as disclosed in the present invention concurrently with the *Bacillus*-based insecticides, wherein the method enhances the insecticidal effectiveness of the *Bacillus*-based insecticides for insect control.

In an embodiment, the present invention provides a safe, biopesticidal composition including culture supernatant containing the recombinant chitinase enzyme and/or cell suspensions of recombinant *E. coli* secreting the recombinant chitinase enzyme, as a contact and ingestion (stomach) biopesticide. In an embodiment, toxicological studies were performed to prove the safety in application of biopesticidal compositions of the present invention as a contact and ingestion biopesticide (Example 16). The recombinant, modified chitinase, BRLA_Chi 90 purported to be used on agricultural fields, horticulture farms, forests, forest nurseries is evaluated for interim risk assessment towards non-target animals.

Low or non-existing toxicity of the culture supernatant containing the recombinant chitinase enzyme and/or cell suspensions of recombinant *E. coli* secreting the recombinant chitinase enzyme, through three different toxicity studies in animal models, such as acute oral toxicity in a murine model (adult Wistar rats) and a dermal irritation test in rabbits. The preliminary toxicological profiling of the recombinant chitinase enzyme provided useful and necessary information for risk assessment and indicates an absence of toxicity and pathogenicity of the chitinase to mammals in laboratory animals (rats and rabbits), guiding the choice for development of a "low risk" next generation, potential biopesticide, as a possible alternative to Bt.

In an aspect, the compositions including the recombinant chitinase of the present invention can be used in combination with other Bt-based biopesticides or other proteins with insecticidal activity to increase insect target range for insect resistance management and control. Furthermore, the compositions can also be used in combination with other biocontrol agents or chemical fungicides for integrated pest management.

The use of recombinant chitinase as an ingestion biopesticide, as an alternative to Bt-based biopesticide, with substantially reduced threat of resistance to be developed. The biological efficacy of the recombinant chitinase, modified BRLA_Chi 90, of the present invention makes it an attractive bioinsecticide/biocontrol agent/and a biofungicide. The development of chitinase-enzyme based technology based on recombinant chitinase, BRLA_Chi 90 from *Brevibacillus laterosporus* as a next generation biopesticide and possible alternative to Bt contributes to an innovation in biopesticide research. The chitinase enzyme-based biological control using *Brevibacillus laterosporus* Lak 1210 could provide a preferred solution for integrated pest management, especially for the control of major insect pests and fungal diseases of significance to forestry and agriculture.

The special characteristics of enzymes exploited for their commercial interest and industrial applications include thermotolerance, tolerance to a varied range of pH, stability of enzyme activity over a range of temperature and pH, and other harsh processing conditions. The recombinant, modified chitinase of the present invention possess many attributes required for an ideal biopesticide for use in integrated pest management programs and with possible applications in bioremediation and biofuel industry. The recombinant chitinase functions in a broad pH range (pH 3.0-11.0), highly alkaline active with a pH optimum of 9.0, thermoactive with a temperature optimum of 55-60° C. and hence could be used in several industrial bioprocesses followed by scale up and commercialization.

In a further embodiment, using the method of chitin affinity adsorption the recombinant, modified chitinase BRLA_Chi 90 secreted into the culture medium can be adsorbed on to crustacean shells for the utilization of fishery wastes generated from seafood processing industries. It can be proposed to be not only as an efficient, inexpensive method of bioremediation for the disposal of marine food wastes (crustacean shells like crab shells, shrimp shells and krill shells) contributing to a substantially cleaner, greener environment but possibly an environmentally benign alternative to extract industrial chitin and chitosan over the traditional chemical method of extraction.

Using the method of chitin hydrolysis herein described, chitin affinity adsorption method is also used for reclamation of the crustacean shells for the production of industrially important chitooligomers, N-acetylglucosamine and glucosamine of therapeutic interest.

The recombinant chitinase of the present invention, BRLA_Chi 90 is an unique enzyme which exhibits endo-chitinase activity, and two types of exochitinase activity. The desirable physicochemical features of the recombinant, modified chitinase, BRLA_Chi 90 includes, its activity at varied pH (pH 3.0-11.0), alkaline activity (optimum pH—9.0) and thermoactivity (optimum temperature-55-60° C.), inherent thermostability (Tm of 66.7° C.) and specificity towards insoluble substrates, in particular natural substrates like chitin rich crustacean shells, which are some of the key considerations for the proposed application of recombinant, modified chitinase, BRLA_Chi 90, in a diverse spectrum of industrial processes.

The recombinant chitinase of the present invention produces industrially important chitobiose and N-acetylglucosamine as major end products, in substantial amounts. The recombinant chitinase is a robust enzyme with industrial applicability because of its unique chitin degradation ability, activity, and stability, since the industrial use of the chitobiose and N-acetyl glucosamine have been limited by the lack of enzyme efficient biotechnological process to produce the large scale production of these commercially valuable products.

In an aspect, the combined endo- and exo-chitinase activity results in a synergistic increase in the chitinolytic activity resulting in greater efficacy of chitinase for insect control and chitin hydrolysis. Evaluation of the efficacy and effectiveness of the recombinant chitinase of the present invention is shown in Examples 1 to 18.

Following are the illustrative and non-limiting examples, including the best mode, for practicing the present invention.

Example 1

Genomic DNA Extraction and PCR Amplification of Chitinase Gene, B/Chi
PCR Amplification of B/Chi Gene from *Brevibacillus laterosporus* Lak 1210 (FIG. 1)

Genomic DNA was extracted from *Brevibacillus laterosporus* Lak1210 (MTCC 5487) as described by Pospiech and Neumann. Briefly, cells of *Brevibacillus laterosporus* were grown in Nutrient Broth with 1% colloidal chitin at 30 C and 200 rpm. Cells were pelleted down and resuspended in 0.5 ml of saline-EDTA (150 mM NaCl, 100 mM EDTA) containing 30 mg/ml lysozyme and 40 mg/ml of RNase. Following incubation at 65° C. for 15 min, proteinase K was added to a concentration of 200 mg/ml followed by 10 ml of a 25% sodium dodecyl sulfate (SDS) solution. After incubating at 65° C. for 15 min, the resulting lysate was chilled briefly on ice and then extracted with phenol-chloroform method.

The extracted genomic DNA was used as a template to amplify chitinase gene. BLASTX analysis (http://www.ncbi.nlm.nih.gov/blast) was performed for selecting the closest chitinase genes and the assembled candidate chitinase sequences were subjected to contig analysis with the DNAMAN software (Version 5.2.2, Lynnon BioSoft, Quebec, Canada) to design the primers. All oligonucleotide primers used in this study as listed in Table 2, were designed using the software PRIMER 3 (http://Frodo.wi.mit.edu/). A pair of gene specific primers chi F (5'-TAACAACAATGATATGAACTGACCTAAG3') and Chi R (5'-CTTCTTCATTTCCAAACGCAGTCATA3') was used to amplify the full length open reading frame (ORF) of 2583 bp. Genomic DNA was digested with Hind III and chitinase gene was amplified in a reaction volume of 25 μL reaction having 50 ng genomic DNA, 50 mM each of dNTPs, 1.5 μl DMSO and 100 ng of each primer, 5× GC buffer and 0.5 units of q5 DNA polymerase.

TABLE 2

Oligonucleotide primers used in this study

| Oligonucleotide | Sequence (5'-3') | Length | Tm | Description |
|---|---|---|---|---|
| CHI-F | TAACAACAATGATATGAACTGACCTAAG | 28-mer | 54.1° C. | Primer for amplification of chi ORF from genomic DNA, forward |
| CHI-R | CTTCTTCATTTCCAAACGCAGTCATA | 26-mer | 54.8° C. | Primer for amplification of chi ORF from genomic DNA, reverse |
| CHI-1 IF | CTTATTGCCAAGCACATGATCAGGATGGAC | 30-mer | 61.6° C. | Primer for site-directed mutagenesis, internal forward 1 |
| CHI-1 IR | GTCCATCCTGATCATGTGCTTGGCAATAAG | 30-mer | 60.1° C. | Primer for site-directed mutagenesis, internal reverse 1 |
| CHI-2 IF | GCAGCAACCCCACATGATGCTTCAAATAG | 29-mer | 61.5° C. | Primer for site-directed mutagenesis, internal forward 2 |
| CHI-2 IR | CTATTTGAAGCATCATGTGGGGTTGCTGC | 29-mer | 61.5° C. | Primer for site-directed mutagenesis, internal reverse 2 |
| CHI_F | GCGGCGCATATGAGAAAGATGTATCAACACATTCCTACTGC[a] | 41-mer | 57.3° C. | Cloning |
| CHI-R | GCCGCCCTCGAGCTTCTTCATTTCCAAACGCAGT-CATATC[b] | 40-mer | 57° C. | Cloning |

[a]The underlined nucleotide sequence in Nde 1 restriction site
[b]The underlined nucleotide sequence is Xho 1 restriction site
The single bases underlined are mutated bases from the native chitinase sequence shown in bold face All the PCR reactions were performed by in the thermal cycler (Bio-Rad, Hercules, Calif., USA) with standard high fidelity phusion PCR protocol using high fidelity polymerase, Q 5 phusion polymerase (New England Biolabs, USA) using the following cycling parameters: 30 s initial denaturation at 98° C., followed by 35 cycles of 10 s at 98° C., 20 s annealing at 60° C., and 60 s at 72° C. followed by a final extension of 10 min at 72° C. (Table 3).

TABLE 3

PCR reaction conditions for amplification of B/chi gene

| Step | Temperature | Time |
| --- | --- | --- |
| Initial denaturation | 98° C. | 60 s |
| 35 cycles | 98° C. | 10 s |
|  | 60° C. | 20 s |
|  | 72° C. | 60 s |
| Final extension | 72° C. | 10 min |

The amplified PCR product was sized by electrophoresis in 1% agarose gels, purified using quick Clean DNA gel extraction kit (Qiagen, Netherlands). The nucleotide sequence of the amplicon was confirmed using a BigDye-eTerminator cycle sequencing kit and an automated DNA sequencer (Applied Biosystems, CA, USA).

The amplified PCR product is 2583 bp in length and designated as BlChi shown in FIG. 1. The sequence of native chitinase gene is listed as SEQUENCE ID No:1.

Example 2—Site Directed Mutagenesis, Cloning and Construction of Expression Plasmid pET/BRLA_Chi 90

Site directed mutagenesis was carried out by overlapping extension-PCR using pET/BRLA_Chi 90 expression plasmid as a template. A single point mutation were introduced to the full length ORF (2583 bp) that was previously cloned into the pET 21 b expression vector to modify the gene sequence using mutagenic primers to generate a restriction site suitable for Nde 1 and xho 1.

The forward mutagenic primers used for site directed mutagenesis are:

```
5'-CTTATTGCCAAGCACATGATCAGGATGGAC-3'
and

GCAGCAACCCCACATGATGCTTCAAATAG.

The reverse sequence is
5'-GTCCATCCTGATCATGTGCTTGGCAATAAG
and

CTATTTGAAGCATCATGTGGGGTTGCTGC-3'.
```

The nucleotide underlined represents the mutated nucleotide and the sequences underlined CACATG and CATGTG represents the restriction site for the enzymes Nde I and xho I, respectively. The mutant clones were selected after sequencing the entire open reading frame to ensure that the desired mutation was successfully introduced as the only mutation in the mutated gene. The mutated sequence of the chitinase gene BlChi was listed as SEQUENCE ID No: 3.

The amplicon B/Chi (2583 bp) was digested with Nde 1 and Xho 1 and cloned into the pET-21 b (+) vector (Novagen), resulting in the construction of recombinant expression plasmid pET/BRLA_Chi 90. The recombinant expression vector was constructed such that the native signal peptide sequence of *Brevibacillus laterosporus* LAK 1210 was in frame with the C-terminus. The expression vector pET/BRLA_Chi 90 was transformed into *E. coli* BL21 (DE3) competent cells.

Recombinants selected on LB agar plates containing 100 µg/ml ampicillin were analyzed by colony per. Six positive genomic clones carrying the full length ORF (2583 bp) were chosen and the recombinant clones were verified by sequencing using gene specific (CHI-F and CHI-R) and vector specific (T7 forward and T 7 reverse) primers. The sequence of the DNA insert was confirmed using 3730XL DNA Analyzer (Applied Biosystems, CA, USA).

The ORF (2583 bp) translates to a polypeptide of 860 amino acid residues with a calculated molecular mass of 89.68 kDa and pI of 5.93. The deduced chitinase enzyme was designated as BRLA_Chi90. The deduced native and mutated amino acid sequence of the recombinant BRLA-_Chi 90 was listed as SEQUENCE ID NO: 3 and SEQUENCE ID No: 4 respectively. The mutated amino acid sequence of the recombinant BRLA_Chi 90, without native signal sequence was listed as SEQUENCE ID NO: 5. The native signal peptide sequence with 42 amino acids was listed as SEQUENCE ID NO: 40. The nucleotide sequences and their encoded sequences were aligned by running a BLAST search on NCBI (http://blast. ncbi.nlm.nih.gov/blast.cgi) and analyzed the DNAMAN software package (Version 5.2.2, Lynnon BioSoft, Vaudreuil Dorton, Quebec, Canada). The nucleotide sequences for the native chitinase and the recombinant (mutated) chitinase sequence were deposited with the GenBank with the accession numbers MF397932 and MF 397933, respectively.

Example 3—Expression, Large Scale Production and Purification of Recombinant, Modified Chitinase, BRLA_Chi 90

SDS-PAGE Analysis of Recombinant, Modified Chitinase, BRLA_Chi 90 (FIG. 2A)

For protein expression, large scale production and purification, positive clones of *Escherichia E. coli* BL21(DE3) harboring the pET/BRLA_Chi 90 vector were grown in Terrific Broth medium supplemented with 100 µg/ml ampicillin at 37° C. to $OD_{600}$ nm of 1.0. Expression of pET/BRLA_Chi 90 was induced with 0.1 mM IPTG and the cells were grown for different time intervals to optimize the overexpression and extracellular secretion of the recombinant chitinase. To analyze expression levels of the secretory protein and the optimal post-induction time for harvesting the cells, the culture supernatant was collected at 1, 2, 3, 6, 8 and 12 h and the protein samples were analyzed by 12% sodium dodecyl sulfate polyacrylamide gel electrophoresis (SDS-PAGE). The cells were harvested after 6 h, post-induction by centrifugation at 8000 g, 4° C., for 10 min, washed with STE buffer (20 mM Tris-HCl pH 7.4, 1 mM EDTA, 300 mM NaCl) and were sonicated on ice (5 cycles, 30 s, each).

The recombinant chitinase was purified from the concentrated culture supernatant and the cytoplasmic fraction of the cell lysate by a single step chitin affinity chromatography using chitin beads (New England Biolabs, USA). The cell lysate/ammonium sulphate dialysate/concentrated culture supernatant was loaded onto a 2 ml Poly-Prep chromatography columns (9×0.8×4 cm) (Amersham Biosciences, USA) packed with chitin beads (New England Biolabs, USA) previously equilibrated with 20 mM Tris HCl (8.0) and the bound proteins were eluted with 20 mM Tris HCl (8.0) and the recombinant chitinase was eluted stepwise with 0.5 M, 0.1 M and 20 mM acetic acid. Fractions with high chitinase activity were collected and concentrated using ultrafiltration. The yield for the recombinant, modified chitinase is about 6 mg/L and could further improved by optimizing the process conditions.

A cost-effective, large scale purification method was developed by chitin affinity adsorption chromatography to selectively adsorb the extracellular chitinase present in the culture supernatant/fermentation broth. The culture supernatant was concentrated using AMICON PM 30 (MWCO 30 kDa). Borosil glass chromatography columns (500 mm) fitted with a stopcock were packed with pretreated, powdered crustacean shells (crab shells or, shrimp shells). The concentrated culture supernatant was loaded onto powdered crustacean shell matrix, previously equilibrated with 20 mM Tris HCl (8.0) and the bound proteins were eluted with 20 mM Tris HCl (8.0). After several washes with distilled water, the recombinant chitinase was eluted stepwise with 0.5 M, 0.1 M and 20 mM acetic acid.

Powdered, crude shrimp shell chitin exhibited an adsorption capacity of 95.2 U/g which was 36.3% higher than the powdered, crude crab shell chitin. The recombinant chitinase, when eluted with 20 mM acetic acid resulted in 93% chitinase recovery with a purification fold of 9.6. The enhanced adsorption could be due to the efficient binding of the substrate binding domain of BRLA_Chi 90 to the insoluble chitin substrates chitin hydrolysis and also efficient chitin hydrolysis due to the unique dual enzyme activity.

The purity of BRLA_Chi 90 was analyzed using 12% sodium dodecyl sulfate-polyacrylamide gel electrophoresis (SDS-PAGE). The molecular mass (94488 Da) calculated from the deduced amino acid sequence without the signal peptide is in reasonable agreement with the molecular mass (89680 Da) of the recombinant chitinase assessed by SDS-PAGE (FIG. 2 A) indicating that BRLA_Chi 90 is a monomeric enzyme. The aminoacid sequence of the recombinant chitinase expressed as a mature protein (without signal peptide) was listed as SEQUENCE ID NO: 5.

Example 4—Zymography Assays (in-Gel Activity Staining) Using Recombinant, Modified Chitinase BRLA_Chi 90

Chitinase Zymography with 4-Methylumbelliferyl Substrates Using Recombinant, Modified Chitinase BRLA_Chi 90
(FIG. 2B)

In gel activity staining assays were performed for rapid detection and semi-quantitative analysis of chitinase by using agarose overlay containing fluorogenic chitooligosaccharide analogs, 4-methylumbelliferyl N-acetyl-β-D-glucosaminide (4-MU-GlcNAc), 4-methylumbelleferyl N,N'-diacetyl-β-D-chitobioside (4-MU-GlcNAc$_2$) and 4-methylumbelleferyl N,N', N"-triacetyl-β-D-chitotrioside (4-MU-GlcNAc$_3$) (Sigma Chemicals, St Louis, USA) for N-acetyl-beta-glucosaminidase, chitobiosidase and endochitinase, respectively.

Protein samples were separated on 12% SDS-PAGE. After electrophoretic separation, the recombinant enzyme was renatured by incubating the gel in 0.1M sodium acetate buffer (pH 5.0) containing 1% (v/v) Triton X-100 at 37° C. for 2 h. An overlay gel containing 4-methylumbelliferyl substrate (10 μm in 1% agarose) was overlaid on the slab gel and the gel sandwich was allowed to incubate at 37° C. for 15 min. The enzyme activity was visualized as bright, fluorescent bands where enzyme had released 4-methylumbelliferone from the chitin analog.

Zymography analyses revealed that the recombinant chitinase exhibited in gel activity against all the three fluorogenic chitooligosaccharide analogs indicating that it has a combined exo- and endochitinase activity (FIG. 2B).

Figure 3:
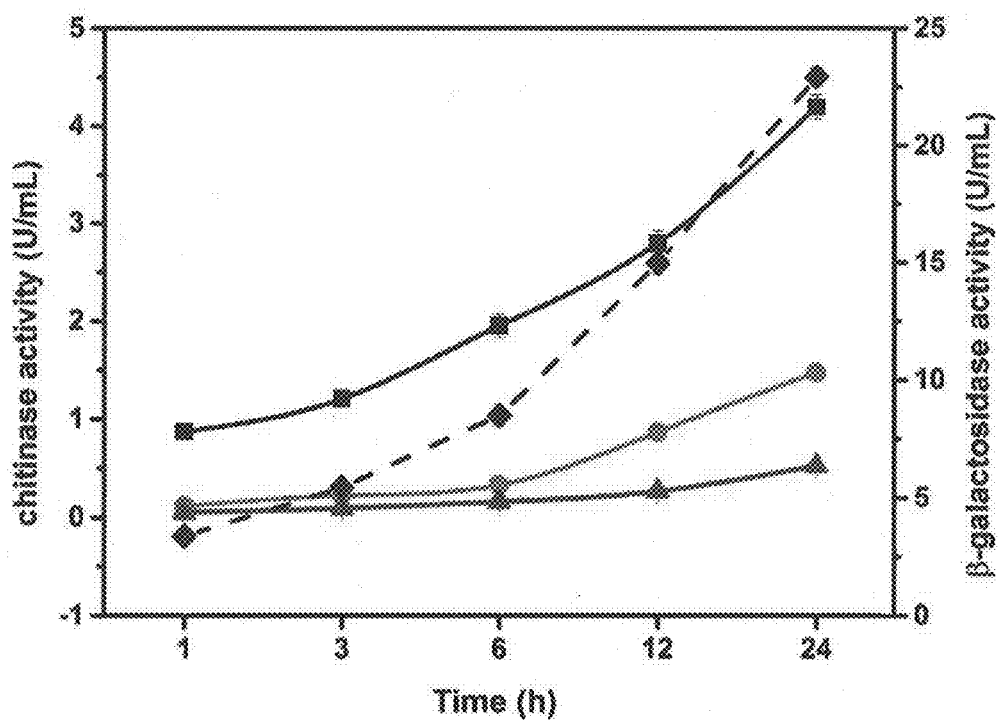

Example 5—Secretion Profile, Extracellular Targeting of the Recombinant, Modified Chitinase BRLA_Chi 90 and Evaluation of Membrane Integrity (Cell Leakage/Permeability/Viability) by β-Galactosidase Activity Secretion Profile of Recombinany, Modified Chitinase BRLA_Chi 90 Expressed in the Different Cell Compartments (FIG. 3)

Cells were harvested by centrifugation at 5,000 g for 20 min at 4° C., and the supernatants were pooled (culture medium with extracellular fraction). Cells were fractionated to separate the recombinant proteins into periplasmic, cytoplasmic and with the EDTA/lysozyme/cold osmotic shock method. Cells were suspended in 30 mL of 20 mM Tris-HCl (pH 7.4) containing 20% sucrose (w/v), 0.5 mM EDTA and a protease inhibitor, incubated on ice for 30 min, and then centrifuged at 15,000 g for 15 min at 4° C. After the addition of 120 mL of 20 mM Tris-HCl (pH 7.4) containing the protease inhibitor, the cells were further incubated on ice for 30 min and centrifuged at 15,000 g for 15 min at 4° C. The supernatants were combined (periplasmic fraction). The resulting cell pellet was suspended in STE buffer (20 mM Tris-HCl pH 7.4, 1 mM EDTA, 300 mM NaCl) and sonicated and centrifuged at 15,000 g for 15 min at 4° C. and the supernatant was pooled (cytoplasmic soluble fraction).

The B/Chi gene ORF with its native signal peptide was efficiently secreted, at first into the periplasmic space of *E. coli* cells and then excreted into the culture medium. Targeting of the recombinant chitinase BRLA_Chi 90 into the extracellular medium allows efficient purification by chitin adsorption chromatography using shrimp shell and crab shell chitin. β Galactosidase is a cytosolic protein and the extracellular β-galactosidase activity detected in the culture medium was used as an indicator of cell leakage/lysis. Post-induction, the culture supernatant was collected at different time points and assayed for β-galactosidase activity. The β-galactosidase activity was quantified by determining the amount of β-galactosidase in the extracellular medium using o-nitrophenyl-D-galactopyranoside (ONPG). The enzyme assay mixture contains 50 μl of the substrate buffer containing 2.0 mg/ml ONPG in 0.2 M phosphate buffer (pH 7.2) was added to 50 μl of the sample, which was then incubated at 37° C. for 10 min. The reaction was stopped by addition of 0.1 ml of 1 M sodium carbonate, and the absorbance was read at 420 nm. One unit of β-galactosidase is defined as the amount which hydrolyzes 1 μmol of ONPG to o-nitrophenol and D-galactose per minute under the experimental conditions.

We have observed that the amount of β-galactosidase activity in the culture medium concomitantly increased with increase in chitinase activity from 1 h to 24 h (FIG. 3). These results demonstrated that the improved secretion during the cultivation period is independent of cell lysis and due to the possible membrane permeabilization/leakage of *E. coli* cells.

Figure 4:
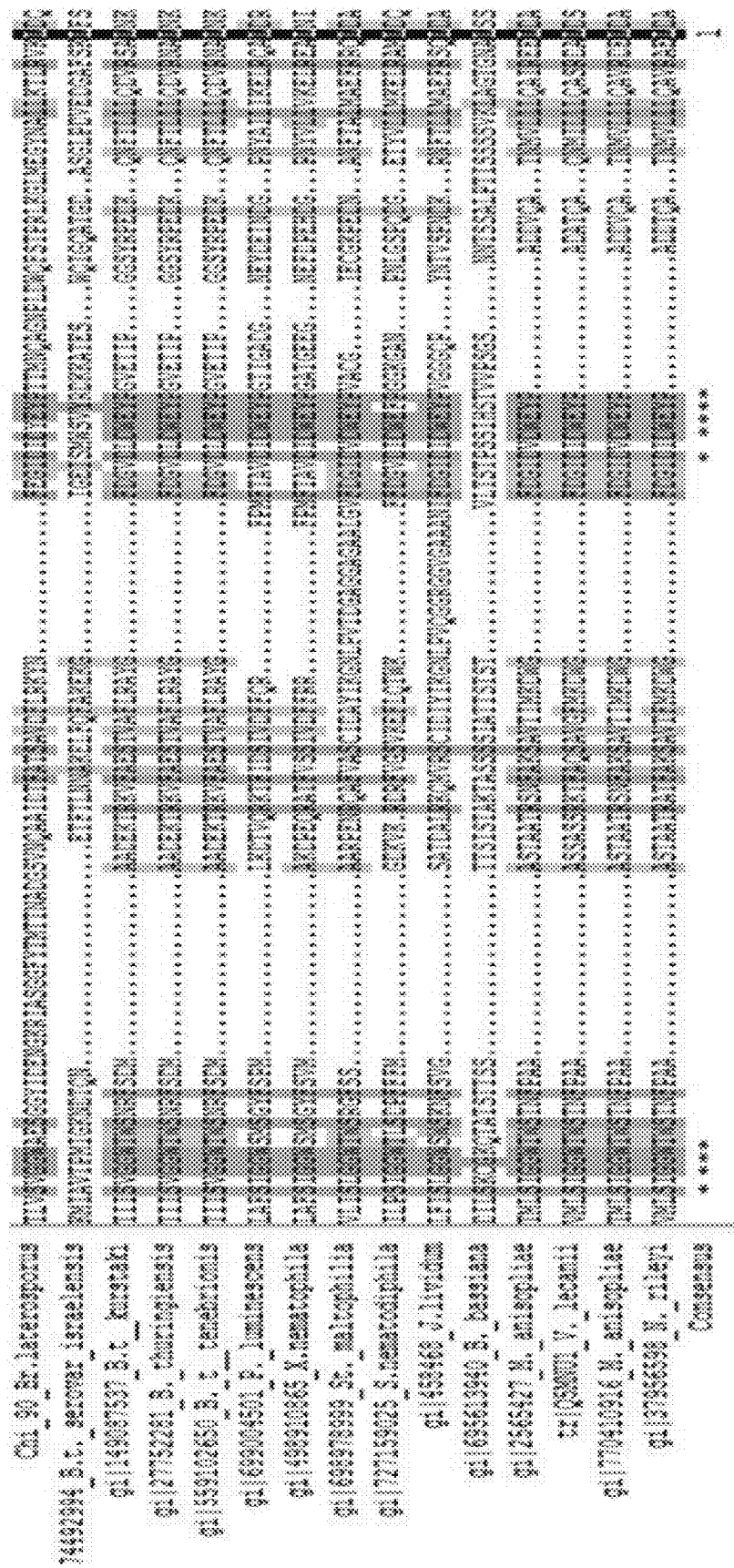

Example 6—in Silico Analysis of the Recombinant, Modified Chitinase, BRLA_Chi 90 Multiple Sequence Alignment Comparison of the Recombinant, Modified Chitinase, BRLA_Chi 90 of *Brevibacillus laterosporus* with the Conserved Domains of Chitinases from Entomopathogens (FIG. 4)

Multiple Sequence Alignment Comparison of the Recombinant, Modified Chitinase, BRLA_Chi 90 of *Brevibacillus*

Figure 5:
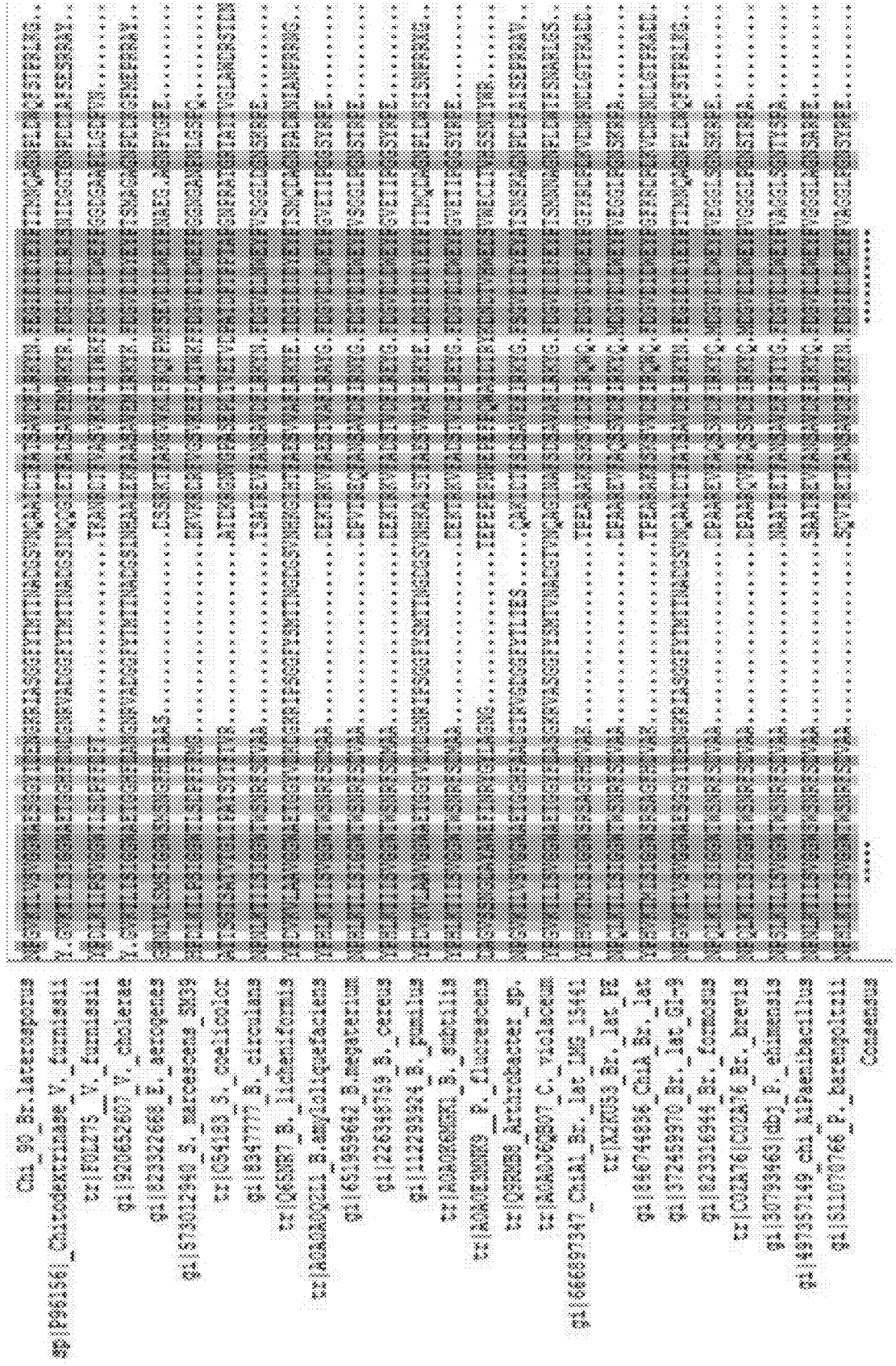
Figure 6:
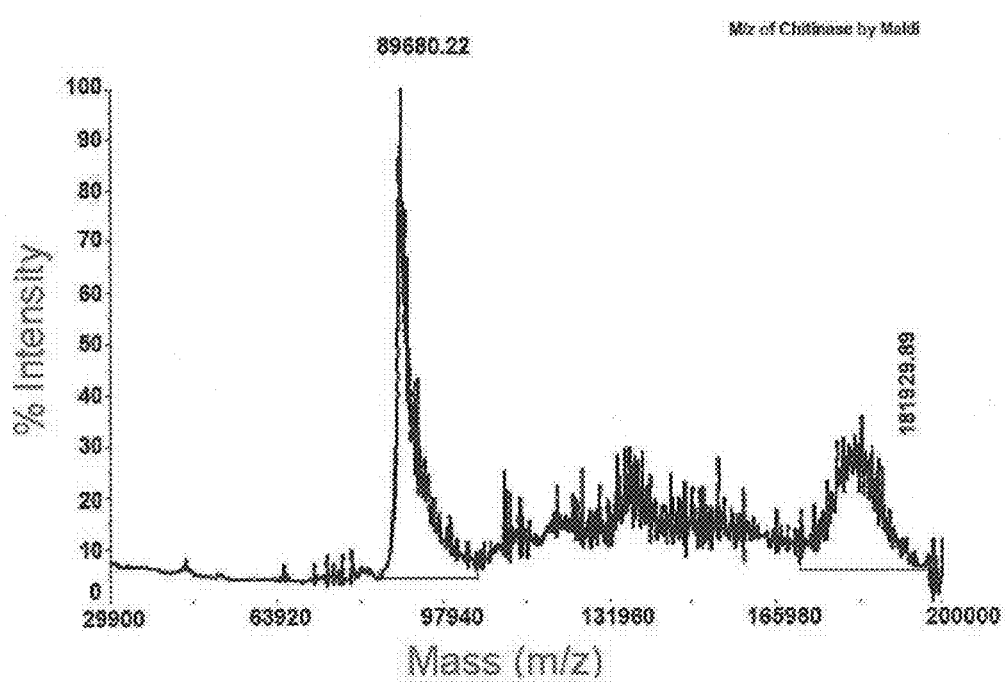
Figure 30:
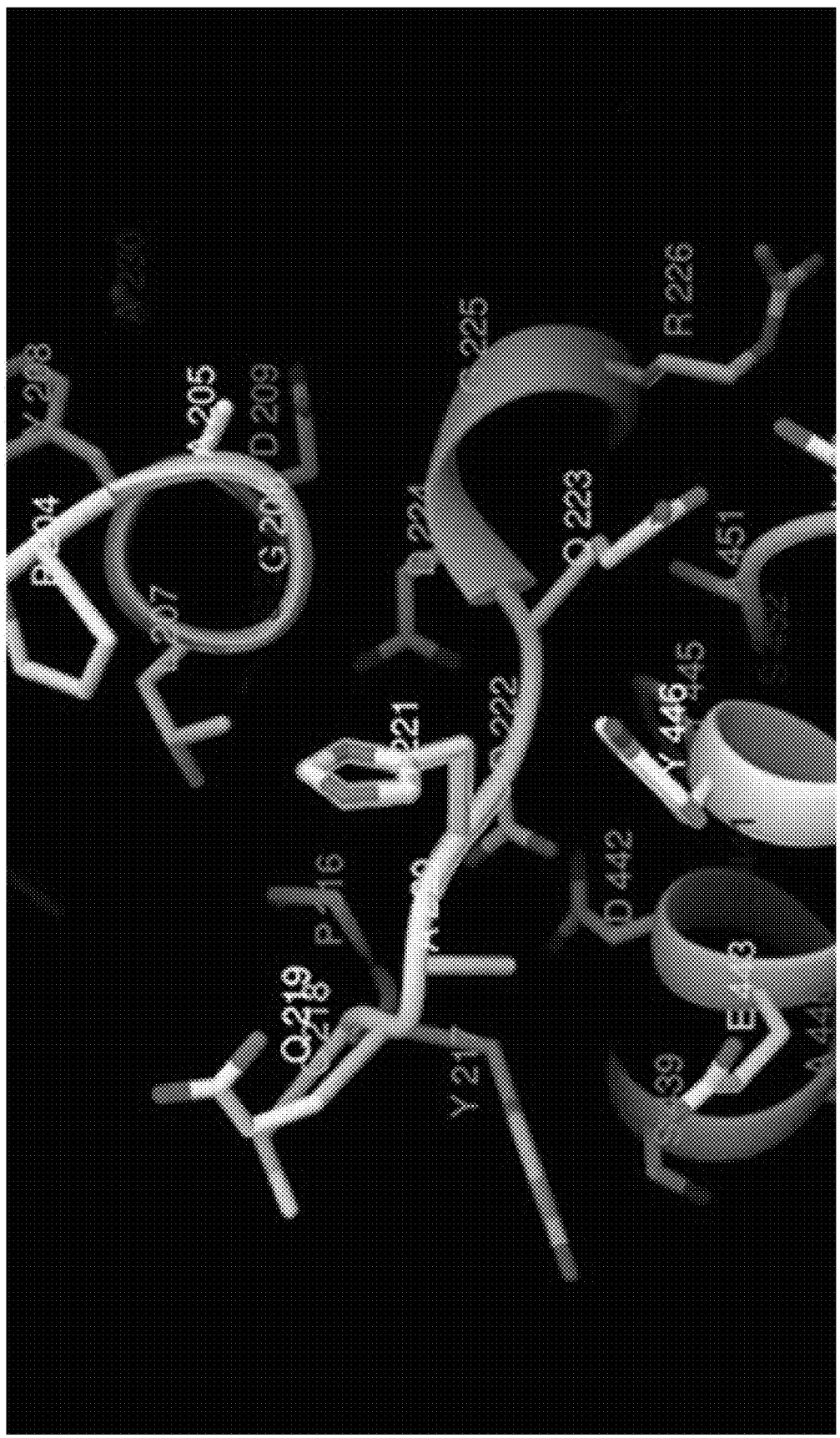

*laterosporus* with the Conserved Domains of Chitinases from Other Bacterial Chitinases (FIG. 5)
Structural Analysis of the Recombinant, Modified Chitinase at Substitution Site Through Protein Structure Prediction Approach (FIG. 30)

The identification of nucleotide sequences from the chitinase recombinant clones was established using the NCBI Blast program (http://www.ncbi.nlm.nih.gov/BLAST). Open reading frame and protein prediction were made using NCBI ORF Finder (http://www.ncbi.nlm.nih.gov/gorf/gorf.html). Sequence alignment was conducted and a phylogenetic tree was constructed using the DNAMAN software ((Version 5.2.2, Lynnon BioSoft, Quebec, Canada).

Multiple sequences alignment of BRLA_Chi 90 and other chitinase sequences retrieved from the predicted proteomes of the genomes from NCBI (http://www.ncbi.nlm.nih.gov/) was done more importantly by identifying the conserved active site signature motif DXXDXDXE. Comparison of the predicted BRLA_Chi 90 chitinase sequence with chitinase sequences from entomopathogens and other bacterial chitinases. It revealed two highly conserved consensus motifs (SIGG and EGIDIDYE) corresponding to a substrate-binding site and catalytic domain respectively confirmed that BRLA_Chi 90 was a member of glycosyl hydrolase family 18 (FIGS. 4 and 5). The consensus sequence ((EGIDIDYE) corresponding to the catalytic domain of BRLA_Chi 90 is novel and different from the other chitinases. The novelty of the consensus sequence of the catalytic domain attributes to the unique functional properties of BRLA_chi 90.

The sequence of BRLA_Chi 90 was analyzed to evaluate their theoretical isoelectric point (pI) molecular weight, percentage of amino acid composition (%)), number of positively and negatively charged residues, extinction coefficient, instability and aliphatic index, Grand Average of Hydropathy (GRAVY) using Expasy Protparam tool (http://us.expasy.org/tools/protparam.html). Protein sequences encompassing signal peptides and the putative signal peptide cleavage site was predicted by SignalP and TargetP tools (http://www.cbs.dtu.dk/services/SignalP/andhttp://www.cbs.dtu.dk/services/TargetP/).

Subcellular localization presumption was performed using ProtComp and WOLF PSORT to refine the secretome predictions.

(http://liux1.softberry.com/berry.phtml?topic=protcomppl&group=programs&subgroup=pro loc and http://wolfpsort.org).

Secondary structure was predicted using PSIPRED server (http://bioinf.cs.ucl.ac.uk/psipred/). The three-dimensional structure of the recombinant chitinase BRLA_Chi 90 protein domain was predicted using the SWISS-MODEL workspace (http://swissmodel.expasy.org) using a chitinase template of chitinase from Chromobacterium violaceum ATCC 12472 (GenBank Accession No. GI:939186282; PDB code 4 TXG A).

The ORF (2583 bp) translates to a gene product of 860 amino acid residues with a deduced molecular mass of 94.4 kDa and a pI of 5.93. The molecular mass of the mature chitinase (89.68 kDa) as estimated by MALDI-TOF and SDS-PAGE analyses which corresponds well with the deduced molecular mass (94.4 kDa). The signal peptide prediction by both Signal P v4.1 (http://www.cbs.dtu.dk/services/SignalP/) and Target P v1.1(http://www.cbs.dtu.dk/services/TargetP/) predicted that BRLA_Chi 90 contained a putative N-terminal signal peptide of 42 amino acids (SEQUENCE ID: 40). The predicted signal sequence of 42 amino acids at the N-terminus of the deduced BRLA_Chi 90 exhibited a typical feature of the signal peptide characteristic of Grampositive bacteria producing secreted proteins. The recombinant chitinase, BRLA_Chi 90 was predicted to be cleaved by a signal peptidase between positions A 41 and S 42.

Soluble proteins tend to have polar or hydrophilic residues on their surfaces. The site directed mutagenesis at positions 661 and 2158 in the native chitinase gene resulted in the aminoacid substitution at position 221 and replacing tyrosine with histidine. The substitution of a polar, hydrophilic histidine (H) residue for a hydrophobic aromatic aminoacid tyrosine (Y) h may increase the interaction with the negatively charged insect cuticle. The substitution also resulted in improved solubility of the protein, another important desirable characteristic feature suitable for biocontrol and other industrial applications of chitinase.

The structure-function of the modified chitinase at the substitution site was predicted using Rosetta (version 3.4) software. The predicted 3 D structure of the recombinant, modified chitinase showing surface exposed histidine at position 221 as depicted in FIG. 30.

Example 7-Mass Analysis and Peptide Mass Fingerprinting of the Recombinant, Modified BRLA_Chi 90

MALDI-TOF/MS Spectrum of Purified BRLA_Chi 90 (FIG. 6)

Listing of Unique Peptides from Peptide Mass Fingerprinting of Recombinant, Modified Chitinase, BRLA_Chi 90 (SEQUENCE ID NO: 7-SEQUENCE ID NO: 39) Table 1

Recombinant chitinase, BRLA_Chi 90 was applied in parallel onto a 12% SDS-PAGE gel using a Laemmli buffer system. Following electrophoresis, protein was stained with Coomassie blue. After destaining, protein bands were excised from the gel and in-gel digested with trypsin (sequencing grade, Promega, WI, USA) using a standard protocol. After overnight digestion at 37° C., the peptides were extracted, dried in a SpeedVac vacuum centrifuge and resuspended in 10 μl of 70% acetonitrile. MALDI-TOF-MS using the UltrafleXtreme MALDI-TOF/TOF (tandem TOF) system (Bruker Daltonics) and α-Cyano-4-hydroxycinnamic acid (5 mg/ml in 60% acetonitrile in 1 mM citric acid) was used as MALDI matrix. An aliquot (1 μl) of the extracted supernatant was mixed with 1 μl of matrix solution directly on the MALDI target plate. Measurements were done in the positive reflectron mode.

For peptide mass fingerprinting, all experiments were performed on a Dionex Ultimate 3000 nano-LC system (Sunnyvale Calif., USA) connected to a linear ion trap-Orbitrap (LTQ-Orbitrap) mass spectrometer (ThermoElectron, Bremen, Germany) equipped with a nanoelectrospray ion source. The mass spectrometer was operated in the data dependent mode to automatically switch between OrbitrapMS and LTQ-MS/MS acquisition. Survey full scan MS spectra (from m/z 300 to 2000) were acquired in the Orbitrap with resolution R=60,000 at m/z 400 (after accumulation to a target of 1,000,000 charges in the LTQ). The method allowed sequential isolation of the most intense ions, up to six, depending on signal intensity, for fragmentation on the linear ion trap using collisionally induced dissociation at a target value of 10,000 charges. General mass spectrometry conditions were: electrospray voltage, 1.5 kV; no sheath and auxiliary gas flow. Ion selection threshold was 500 counts for MS/MS, and an activation Q-value of 0.25 and activation time of 30 ms were also applied for MS/MS.

MS/MS peak lists from individual RAW files were generated using DTA SuperCharger package, version 1.29, available at the MSQuant validation tool. Protein identification was performed by using MASCOT Deamon for multiple searches submission on a local Mascot server v2.1 (Matrix Science) The fragment spectra obtained by tryptic digestion were evaluated and submitted to the bacteria subset of the chitinase database. The search parameters used were: Enzyme: Trypsin/P (no proline restriction); Maximum missed cleavages: 3; Carbamidomethyl (C) as fixed modification; N-acetyl (Protein), Oxidation (M), pyro-glu (Q) and pyro-glu (E) as variable modifications; Peptide mass tolerance of ±15 ppm; MS/MS mass tolerance of 0.5 Da. Under these criteria, Mascot indicated a minimal score of 22 for p≤0.01 and 15 for p≤0.05. All data had an average mass accuracy of 2.8 ppm. Spectra and protein validation were performed using an open source software called MSQuant (version 1.5a61), largely used for LC-MS/MS data analysis. Proteins were validated statistically, based on the score of their individual peptides. Tryptic peptides with a minimal score of 22 for each (protein false-positive probability of 0.01%) but a MS/MS score higher than 38 were accepted (protein false-positive probability lower than 0.25%). Using these criteria, all MS/MS identifications of peptides present in entries with reversed sequences (i.e. false positive identifications) were not validated, since none of the Identifications with only one unique peptide were accepted only after manual validation. Quality criteria for manual validation were the assignment of major peaks, the occurrence of uninterrupted y- or b-ion series of at least 3 consecutive amino acids, the preferred cleavages N-terminal to proline bonds and C-terminal to Asp or Glu bonds, and the possible presence of a2/b2 ion pairs.

The identified peptide sequences are novel compared to the previously reported sequences. The spectra matched 33 tryptic peptides (SEQUENCE ID NO 7-39) (Table 1) that could be correlated to the peptide sequences from chitinase (Uniprot KB-A0A0F7C0B6_BRELA) from *Brevibacillus laterosporus* ATCC 64 and chitodextrinase (UniprotKB-A0A075R004 BRELA) from *Brevibacillus laterosporus* LMG 15441 with 100% identity. Though recombinant chitinase, Chi 90 shows 99% identity with Chitodextrinase (CCF12514.1) from *Brevibacillus laterosporus* (GI 9), they don't share any functional homology. Irrespective the source of organism, the enzyme chitodextrinase doesn't solubilise insoluble forms of chitin like crystalline chitin (chitin flakes), amorphous chitin (colloidal chitin), it will only act on soluble chitooligomers.

(http://www.prospecbio.com/Chitodextrinase_8_50/and http://www.uniprot.org/uniprot/P96156). Whereas, a true chitinase will act on native chitin and completely degrade it to monomer, N-acetylglucosamine.

As demonstrated by most sensitive, reliable ESI-MS experiments, the recombinant, modified chitinase, BRLA-_Chi 90 is predominantly an exochitinase (with chitobiosidase activity) acting on insoluble, colloidal chitin to yield chitobiose which is then converted to monomer, N-acetylglucosamine. The ability of Chi 90 to act on native chitin (insoluble colloidal chitin) strongly indicates that it is "true chitinase" and not a chitodextrinase. The complete degradation of native chitin also demonstrates that Chi 90 also exhibits N-acetyl β glucosaminidase activity proving that it is an efficient chitinase suitable for industrial applications, also taken into consideration, its other novel characteristics (FIGS. 12-18, 19A-19C).

The examples clearly illustrate that the recombinant modified chitinase is a novel enzyme since two proteins with similar sequence homology can be functionally different and have different biological activity and mode of action.

Example 8—Determination of Chitinase Activity by Fluorogenic Assays, Optimum, pH and Temperature Profile of Recombinant, Modified Chitinase BRLA_Chi 90

Optimum pH Profile for Exo- and Endochitinase Activity Using Fluorogenic 4-Methylumbelleferyl Substrates (FIG. 7)

Figure 8:
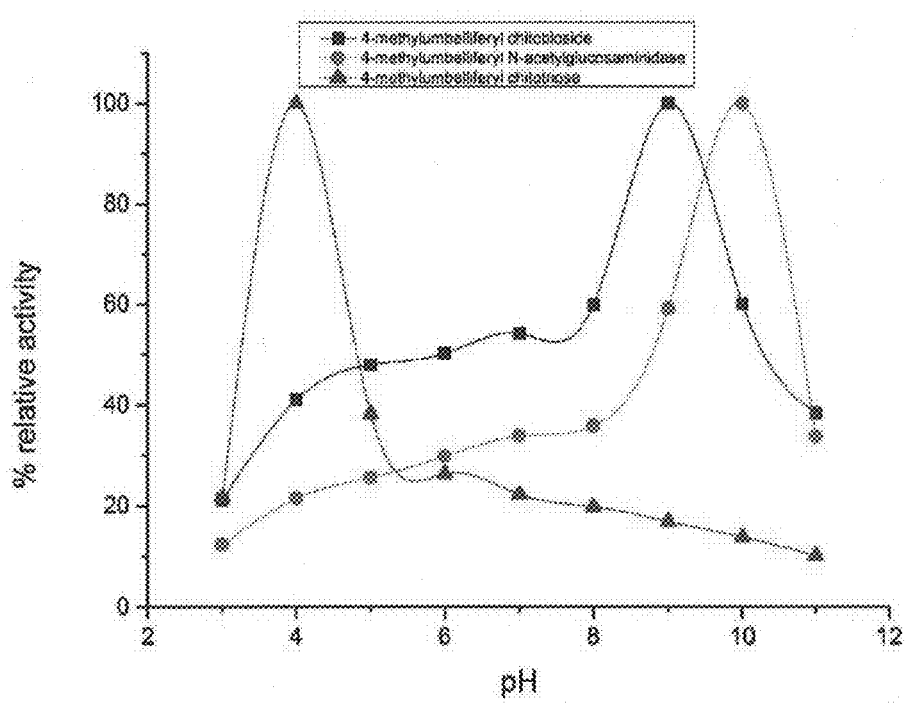

Optimum Temperature Profile for Exo- and Endo Chitinase Activity Using Fluorogenic 4-Methylumbelleferyl Substrates (FIG. 8)

Most sensitive and reliable microplate fluorometric enzyme assays were performed using fluorogenic 4-methylumbelleferyl substrates in a Enspire multimode plate reader (Perkin Elmer Inc, Japan) at an excitation wavelength of 360 nm and an emission wavelength of 450 nm. Chitinolytic activity was fluorimetrically assayed by using fluorogenic chitin analogs, 4-methylumbelliferyl N-acetyl-β-D-glucosaminide (4-MU-GlcNAc$_1$), 4-methylumbelliferyl N, N'-diacetyl-β-D-chitobioside (4-MU-GlcNAc$_2$) and 4-methylumbelliferyl N, N', N''-triacetyl-β-D-chitotrioside (4-MU-GlcNAc$_3$) as substrates to detect exochitinase and endochitinase activity. Chitinase specificity was estimated by the cleavage of the β-1,4-bond that releases 4-methyllumbelliferone from the different fluorogenic substrates.

In a standard assay, a mixture of 10 μM of 4-MU substrate in 0.05 M sodium acetate buffer (pH 5.0) and 1 μl (0.1 μg) of purified enzyme in a total volume of 100 μl was incubated at 37° C. for 5 min as described previously (56). The reaction was stopped by the addition of 100 μl of 0.2 M sodium carbonate solution. One unit of enzyme activity was defined as the amount of enzyme releasing 1 μmol of 4-MU of the substrate per minute under assay conditions. Net values of each reaction were calculated by subtracting the fluorescence obtained in substrate and enzyme blanks a parallel reaction. A standard curve for free 4-methylumbelliferone was used to determine the amount of the products formed. Enzyme activity was expressed as nmol of 4-methylumbelliferone released/min/mg of protein.

Highest activity was obtained with 4-MU-GlcNAc$_2$ (exochitinase, chitobiosidase activity) followed by 4-MU-GlcNAc$_1$ (Glucosaminidase activity) and lower activities with 4-MU-GlcNAc$_3$ (endohtinase activity) (Table 6).

TABLE 6

Specific activity for culture supernatant and cell fraction of the recombinant, modified chitinase BRLA_Chi 90 using fluorogenic 4-methylumbelliferyl substrates

| Substrate | Culture supernatant | Cytoplasmic fraction of cell lysate |
| --- | --- | --- |
| 4-MU - GlcNAc$_1$ | 3623 ± 38* | 1455 ± 56 |
| 4-MU - GlcNAc$_2$ | 6954 ± 42 | 2946 ± 39 |
| 4-MU - GlcNAc$_3$ | 1378 ± 28 | 560 ± 31 |

*Values are mean of the three replicates

Based on the cleavage pattern, chitinases have been classified into two broad categories-endochitinases and exochitinases. Endochitinases cleave chitin randomly at internal sites to form oligomers of different length, whereas exochitinases are classified as a) chitobiosidases, which catalyze the progressive release of chitobiose from the nonreducing end of the chitin chain, and b) β 1-4-N-acetylglucosaminidases, which cleave the oligomeric products ofendochitinases and chitobiosidases, typically chitobioses generating N-acetylglucosamine. Fluorogenic assays showed that BRLA_Chi 90 exhibits a major exochitinase activity, predominantly a chitobiosidase activity and also N-acetylglucosaminidase activity, with some endochitinase activity. Zymogram analyses and real time ESI-MS studies also confirmed that BRLA_Chi 90 is a unique, chitinolytic enzyme with a combined exo- and endo-chitinase activity. The combined exo- and endo-chitinase activity results in a synergistic increase in the chitinolytic activity resulting in greater efficacy of chitinase for insect control and chitin hydrolysis.

The optimal pH for recombinant BRLA_Chi 90 was determined by assaying the purified enzyme at different pH (3.0-11.0) using appropriate buffers and measuring the relative activity under standard assay conditions using fluorogenic 4-methylumbelliferyl substrates. The buffer systems used were citrate buffer (50 mM, pH 3.0-4.0), acetate (50 mM, pH 4.0-5.0), phosphate (50 mM, pH 6.0-8.0), Tris HCl (50 mM 8.0-9.0) and carbonate-bicarbonate (50 mM, pH 9.0-11.0). The optimum temperature for the purified recombinant chitinase was determined by performing the standard assay at temperatures of 25-90° C. in 50 mM sodium acetate buffer (pH 5.0) and the enzyme activity was measured as relative activity.

The optimal temperature of the recombinant chitinase was found to be 55° C. for the N-acetylglucosaminidase and chitotriosidase activity and 60° C. for the chitobiosidase activity (FIG. 7). The recombinant chitinase was active in a broad range of varied pH (3.0-11.0) with a pH optimum of 9.0 (Tris HCl buffer), 10.0 (sodium carbonate-bicarbonate buffer) and 4.0 (citrate buffer) for the chitobiosidase, N-acetylglucosaminidase and chitotriosidase activity, respectively (FIG. 8).

Example 9—Evaluation of Secondary Structure and Thermal Stability of Recombinant, Modified Chitinase, BRLA_Chi 90 by Circular Dichroism Spectroscopy (CD)

Figure 9:
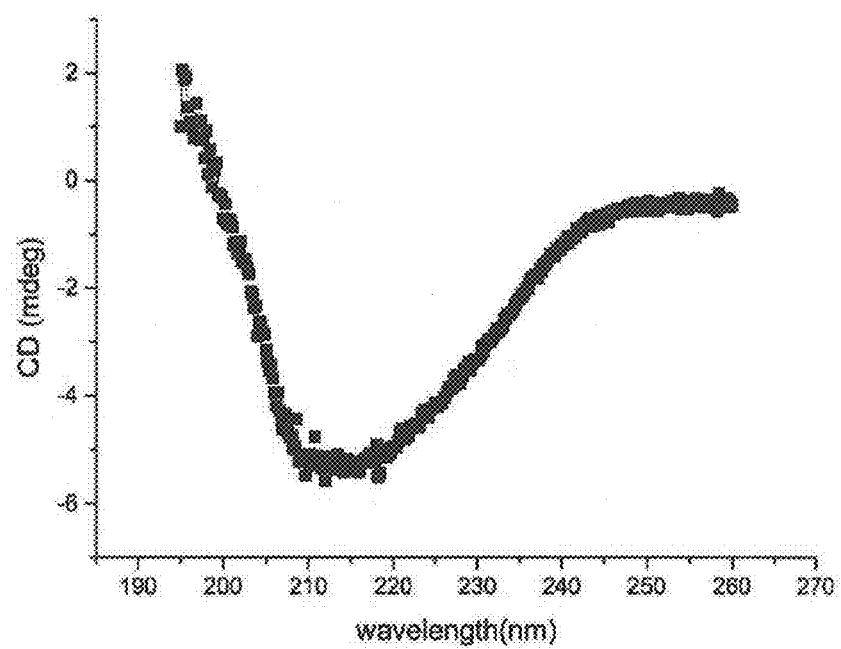
Figure 10:
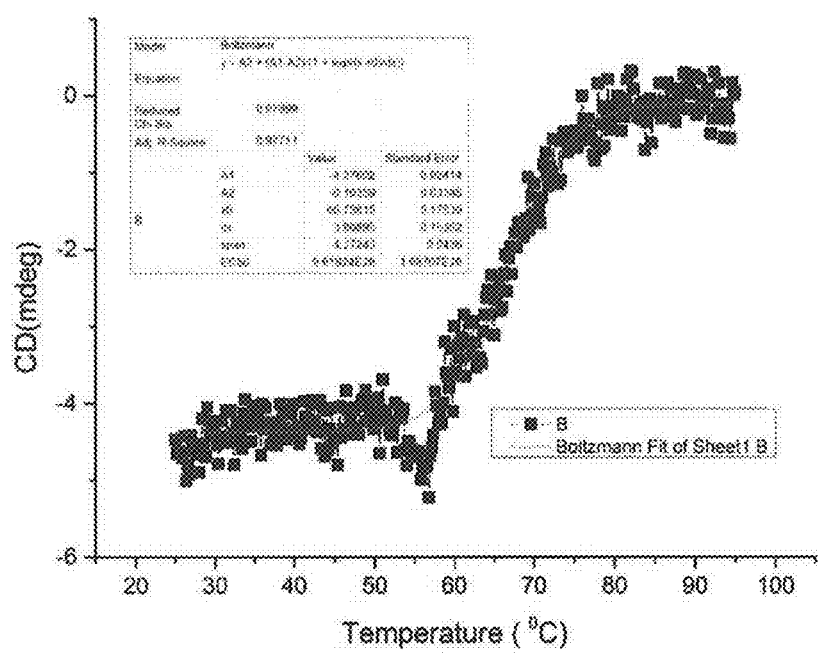

CD Spectrum of Recombinant BRLA_Chi 90 Showing Secondary Structure (FIG. 9)
CD Spectrum of Recombinant BRLA_Chi 90 Showing Thermal Unfolding (FIG. 10)

CD measurements were conducted using a JASCO-715 spectropolarimeter with a Peltier-type cell holder, which allows for temperature control. Wavelength scans in the far (190 to 260 nm) and the near (260 to 360 nm) UV regions were performed in Quartz SUPRASIL (HELLMA) precision cells of 0.1 cm path length. Each spectrum was obtained by averaging five to eight successive accumulations with a wavelength step of 0.2 nm at a rate of 20 nm, response time 1 s, and band width 1 nm. Buffer spectra were accumulated and subtracted from the sample scans. The absorption spectra were recorded selecting the UV (single) mode of the instrument. CD experiments involving thermal scanning have been carried out in the range from 20 to 90° C., at 215, 220, and 222 nm, and heating scan rates ranging from 0.3 to 2.5 K/min.

Secondary structure of the protein showed 20.47% alpha helix, 27.09% beta sheets, 11.57% turns and 40.93% coils, indicating that BRLA_Chi 90 is an alpha-beta protein (FIG. 9). The CD thermal scan studies revealed that the thermal melting temperature of the recombinant chitinase is 66.7° C., indicating that it's a thermostable enzyme (FIG. 10).

Example 10—Time Course Chitin Hydrolysis by Real Time ESI-MS Using Recombinant, Modified Chitinase BRLA_Chi 90 from *Brevibacillus laterosporus* Lak 1210

Figure 11:
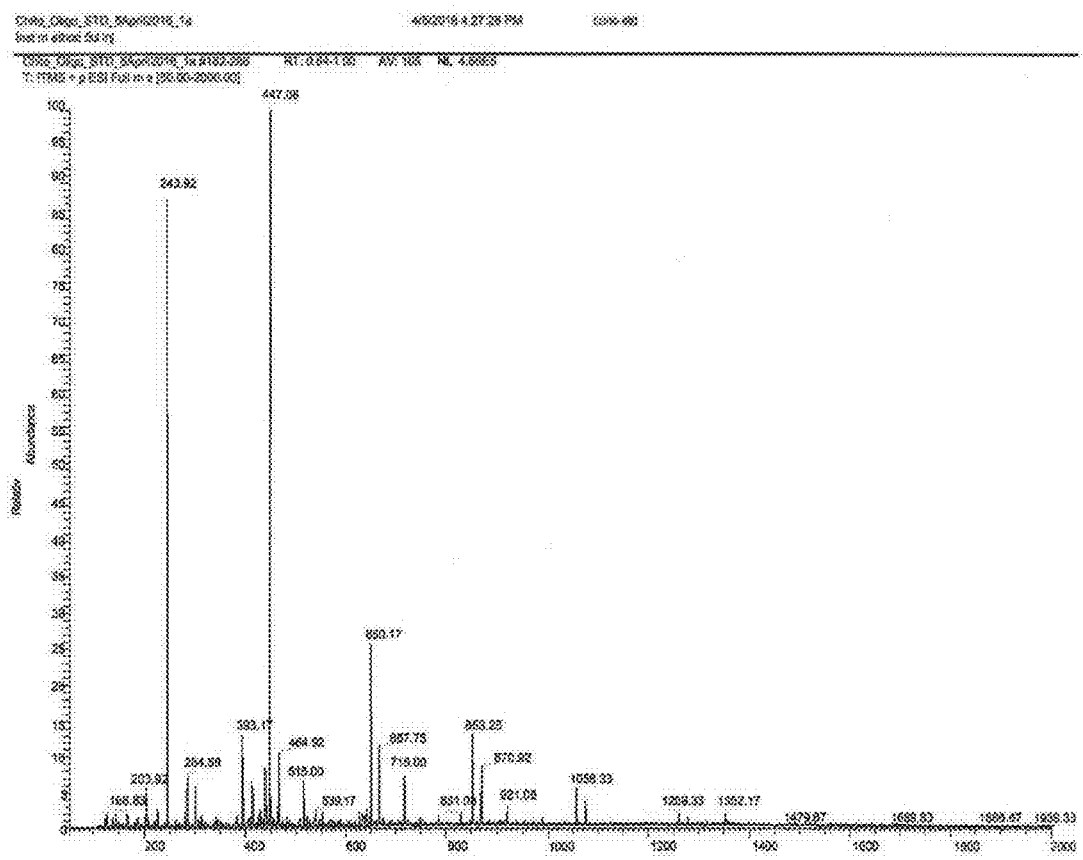
Figure 12:
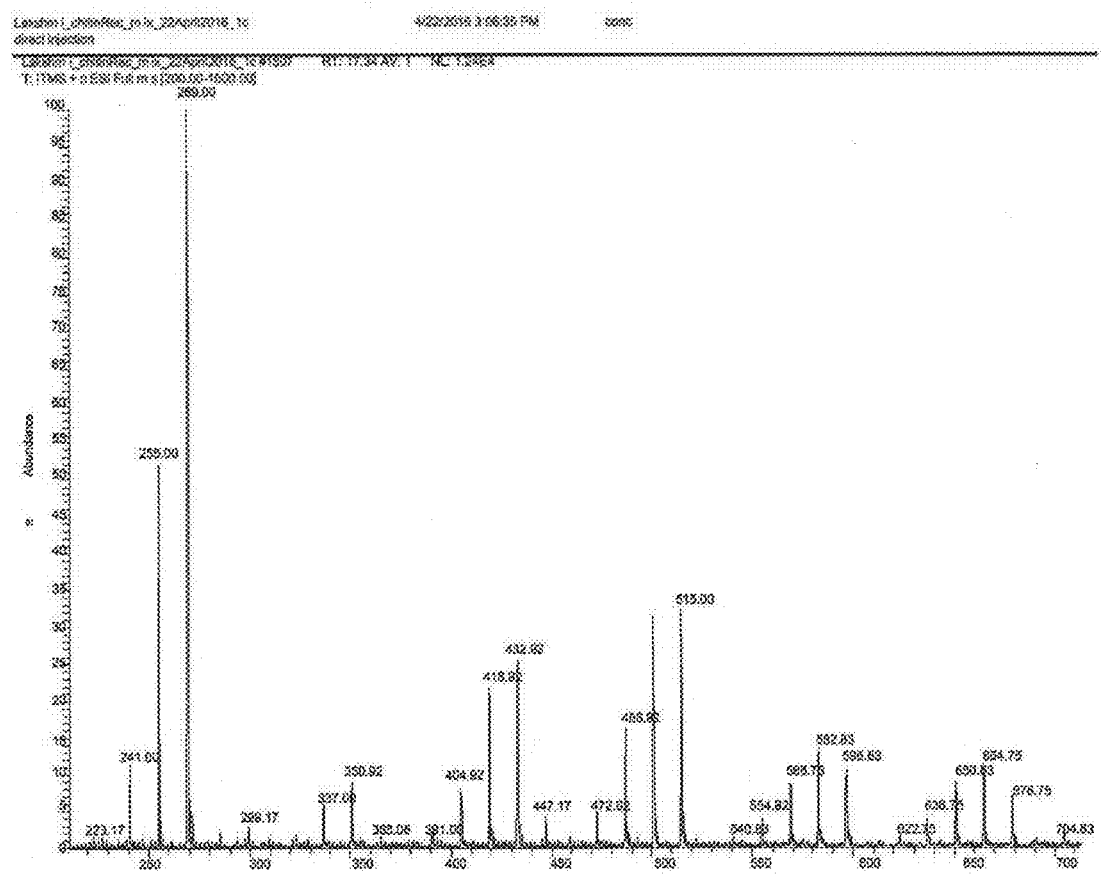
Figure 13:
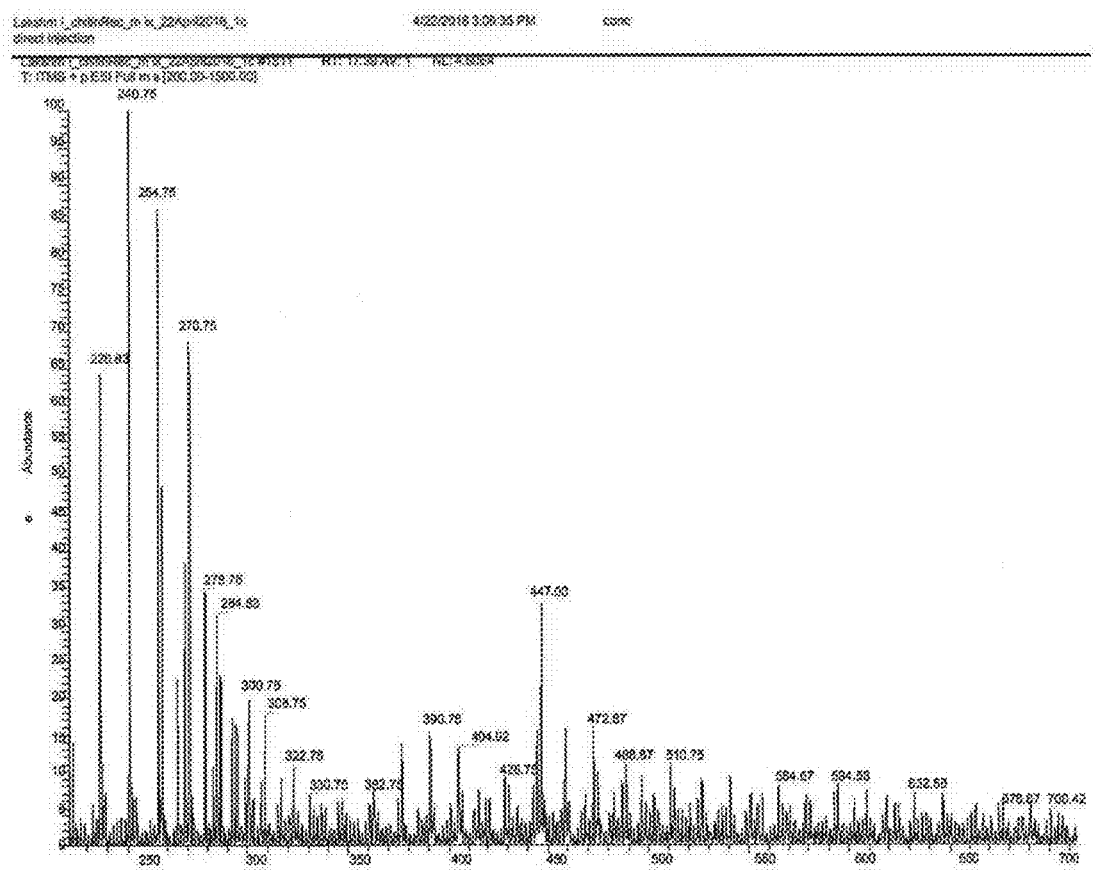
Figure 14:
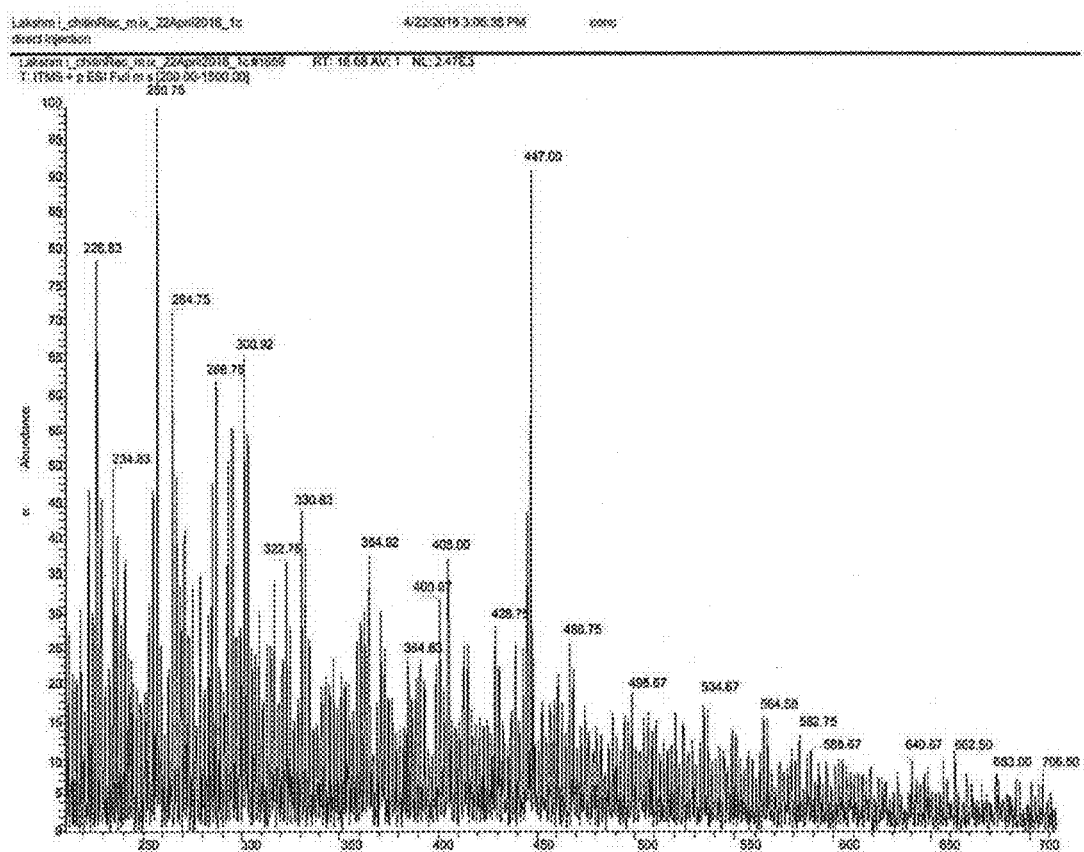
Figure 15:
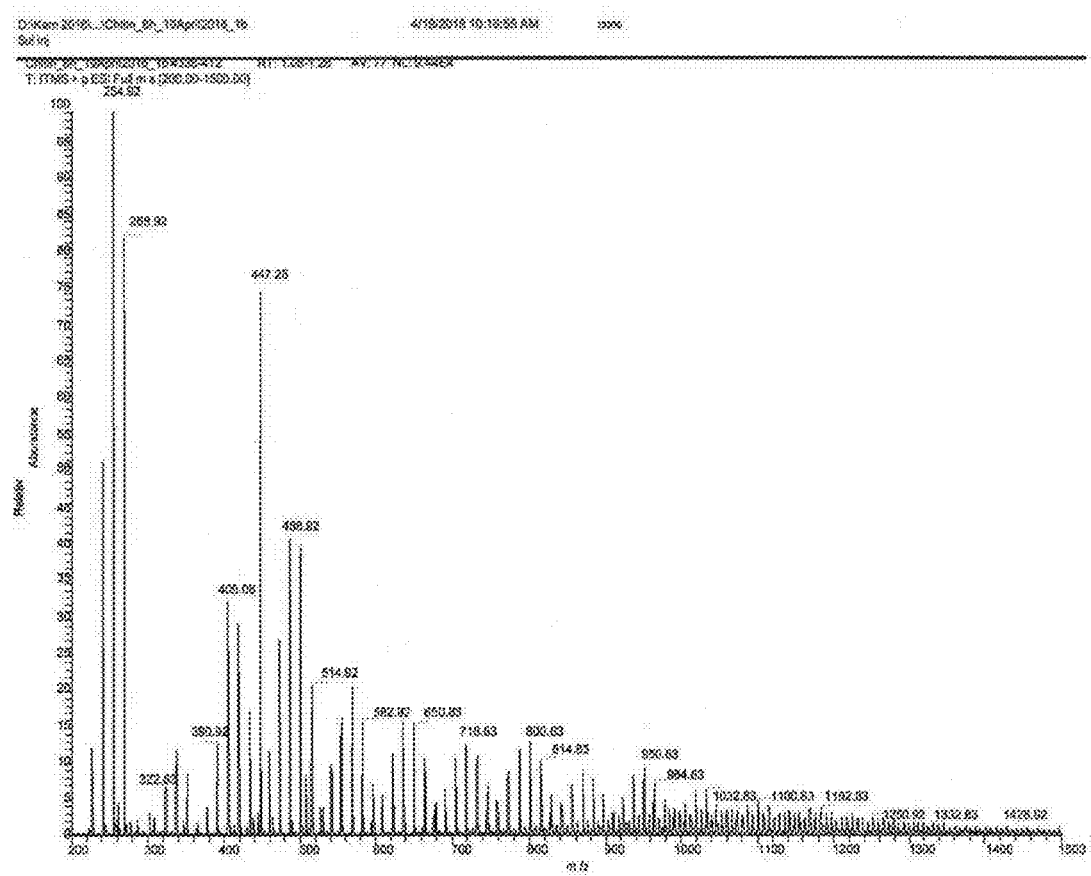
Figure 16:
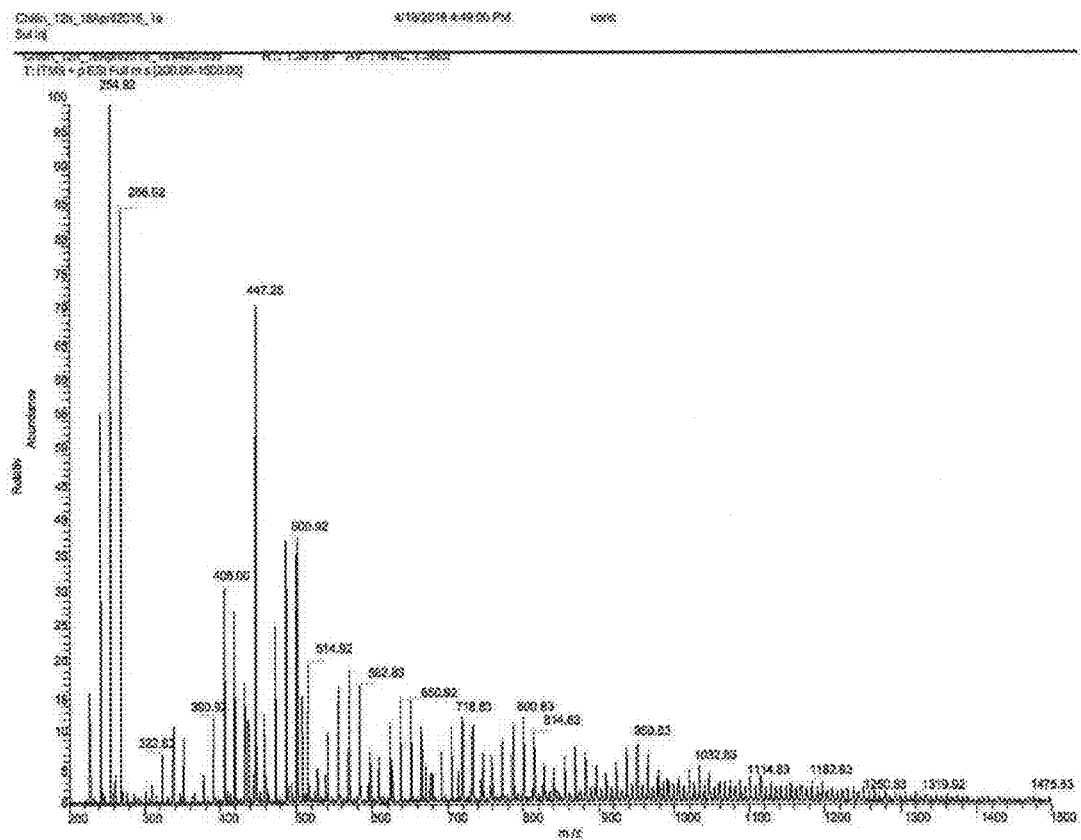
Figure 17:
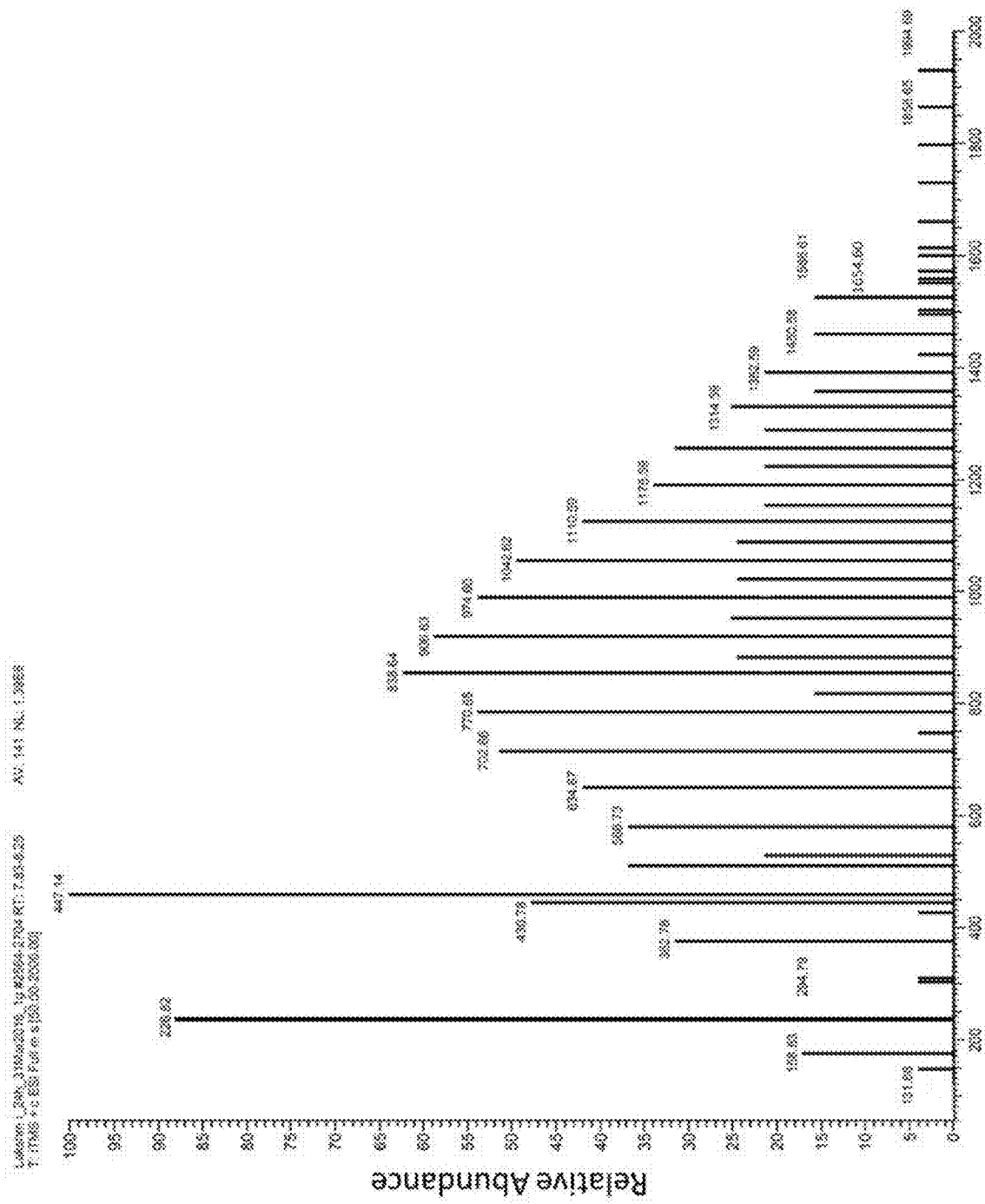
Figure 18:
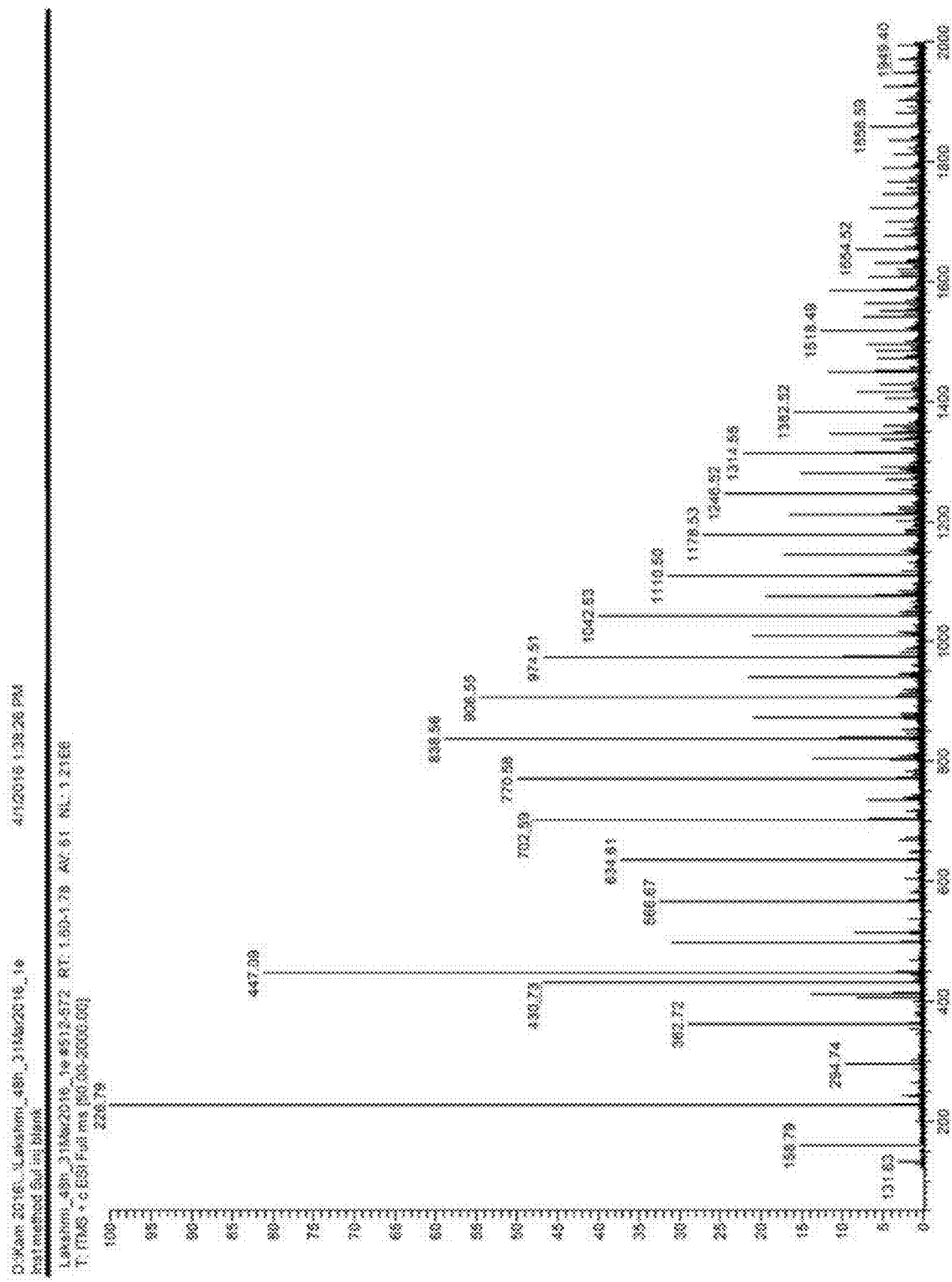

ESI-MS profile of chitooligosaccharide standards Mass spectroscopic analysis-using electrospray ionization mass spectrometry (ESI-MS) of chitoligosaccharides standards with showing their masses—GlcNAc (244.11) GlcNAc2 (447.23) GlcNAc3(650.30) GlcNAc4(853.35) GlcNAcc5 (1056.38) GlcNAc6(1259.4 (FIG. 11)
Real Time ESI-MS of Chitin Hydrolysis (20 Min) Using Recombinant, Modified BRLA_Chi 90 from *Brevibacillus laterosporus* Lak 1210 (FIG. 12)
Real Time ESI-MS of Chitin Hydrolysis (1 h) Using Recombinant, Modified BRLA_Chi 90 from *Brevibacillus laterosporus* Lak 1210 (FIG. 13)
Real Time ESI-MS of Chitin Hydrolysis (3 h) Using Recombinant, Modified BRLA_Chi 90 from *Brevibacillus laterosporus* Lak 1210 (FIG. 14)
Real Time ESI-MS of Chitin Hydrolysis (6 h) Using Recombinant, Modified BRLA_Chi 90 from *Brevibacillus laterosporus* Lak 1210 (FIG. 15)
Real Time ESI-MS of Chitin Hydrolysis (12 h) Using Recombinant, Modified BRLA_Chi 90 from *Brevibacillus laterosporus* Lak 1210 (FIG. 16)
Real Time ESI-MS of Chitin Hydrolysis Using (24 h) Recombinant, Modified BRLA_Chi 90 from *Brevibacillus laterosporus* Lak 1210 (FIG. 17)
Real Time ESI-MS of Chitin Hydrolysis (48 h) Using Recombinant, Modified BRLA_Chi 90 from *Brevibacillus laterosporus* Lak 1210 (FIG. 18)

We report on the sensitive monitoring of an enzymatic reaction via time resolved ESI-MS. Enzymatic reactions are coupled online with MS in which a continuous-flow system coupled via ion-spray to a mass spectrometer was used for the detection of the end products by their molecular mass (to charge ratio). Characterization of the recombinant chitinase enzyme, BRLA_Chi 90 by real-time ESI-MS allows an easy and rapid method of determining its chitinase activity using native unlabeled substrates like chitin flakes, colloidal chitin and in particular, the powdered chitin extracted from crab shells and shrimp shells.

After mixing the substrate (1% colloidal chitin/1% glycol chitin) and 10 µl of the purified enzyme (1 mg/ml), the reaction mixture was infused with a flow rate of 5 µL/min into the mass spectrometric interface via a tubing-connected (1/16"×ID 0.13 mm, length 200 mm) syringe (Hamilton-Bonaduz, Switzerland, 100 µL) located in a syringe pump (Hugo Sachs Elektronik, Hugstetten, Germany). The syringe has to be refilled every 20 min. Several measurements were carried out at 20±2° C. Experiments were performed using a mass spectrometer from Agilent (Santa Clara, Calif., USA), an LC/MSD TOF model equipped with an ESI source. The measurements were carried out in positive ionization mode with 300° C. drying gas temperature, 480 L/min drying gas flow and 15 psig nebulizer gas pressure, 4000 V capillary voltage, 60 V skimmer voltage and 215 V fragment or voltage. The mass range was set to 200-2000 m/z and data acquisition was performed at 0.88 cycles/s. The parameters used for mass spectrometric detection were optimized with HEWL. The nitrogen drying gas was supplied by a nitrogen generator (nitrogen purity ≥99.5%). Agilent Technologies (Waldbronn, Germany) software was used for system control and data acquisition (Analyst QS, LC-MS TOF Software, Ver. A.01.00. Extracted ion chromatogram signals were summed for a time course of 10 min and the time courses were smoothed with a Gaussian filter with a width of 400% and a limit of 10. The end products of time resolved chitin hydrolysis by ESI-MS indicated diacetylchitobiose as the primary product starting from 20 min to 48 h along with a significant amount of N-acetylglucosamine formed during 24-48 h but very low amounts of oligosaccharides (trimers) suggesting that the enzyme also exhibits endochitinase activity. Since chitobiose (441.25) was detected in higher amounts as a sodium adduct, it was deduced that BRLA_Chi 90 is prevalently an exochitinase with exo-N, N'-diacetylchitobiohydrolase (chitobiosidase) activity. The detection of monomer N-acetylglucosamine (226.8) as an end product after 24 and 48 h hydrolysis confirmed that the enzyme also possesses N-acetylglucosaminidase activity as confirmed by the zymography assays and enzyme activity assays using flurogenic 4-Methyl umbelleferyl substrates. Endochitinase activity of BRLA_Chi 90 was also confirmed by in gel-activity assays, hydrolysis of fluorogenic trisaccharide analogue to triacetylchitotriose and also by the accumulation of trisaccharide by hydrolysis of native colloidal chitin suggesting that it is also an endochitinase. Alternatively, the recombianant enzyme, BRLA_Chi 90 can exhibit exo-N, N', N"-triacetylchitotriohydrolaseactivity cleaving the chitotriose to form the major end products chitobiose and N-acetylglucosamine. Till date, there are not many reports about either chitobioses or chitinases with a combined activity and enzymatic production ofchitobiose and N-acetylglucosamine as major end products, in particular from entomopathogens. There are no reports of combined activity of endochitinase, exoN, N'-diacetylchitobiohydrolase and exo β-1,4 N-acetyl-acetylglucosaminidase activity and/or exo-N, N', N"-triacetylchitotriohydrolase activity for a single chitinase enzyme from *Brevibacillus laterosporus*. To our knowledge, the present study is the first report of a chitinase with and multiple mechanism for chitinolytic activity from *Brevibacillus laterosporus*. The present invention is also the first report on selective bio production of industrially important chitin derivatives, chitobiose and N-acetyl glucosamine (NAG) from chitin at the same reaction temperature (55-60° C.), using culture supernatant containing the extracellular recombinant chitinase. Thus, the present invention also pertains to a valuable cost-effective process of N-acetylglucosamine and chitobiose from marine wastes from fishery industries like crustacean shells (crab shells and shrimp shells) using culture supernatant containing the recombinant chitinase enzyme.

Figure 19A:
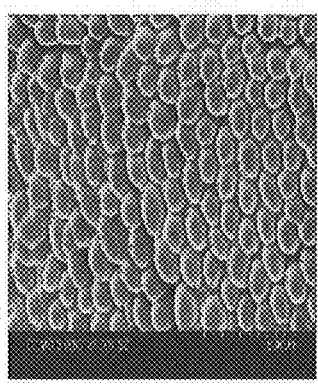
Figure 19B:
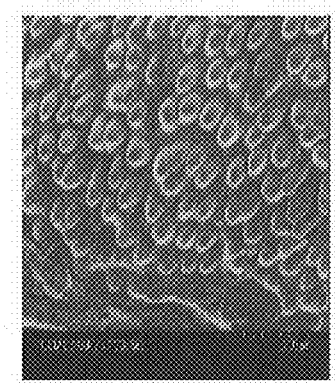
Figure 19C:
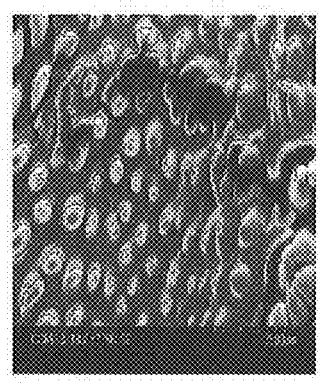

Example 11—Evaluation of the Efficacy and Effectiveness of Recombinant, Modified Chitinase BRLA_Chi 90 for Controlling *Spodoptera litura* Topical Application Bioassays—a Scanning Electron Microscopy (SEM) Study of the Insect Cuticle SEM Study of Hydrolytic Effects of Chitinase on the Cuticle of *Spodoptera litura* (Topical Bioassays) (FIGS. 19A-19C)

Topical bioassays were performed to observe structural changes on fifth instar larvae cuticular surfaces were observed by scanning electron microscopy after treatment with the recombinant chitinase. Ridge-like structures could be observed on the intact cuticular surface (treated with 20 mM potassium phosphate buffer, pH 7.0) of control larvae. Gross morphological changes were observed in when cuticular surface was treated with recombinant chitinase and degradation of the ridge-like structures was observed, which is suggestive of the hydrolytic effect of chitinase.

Figure 20B:
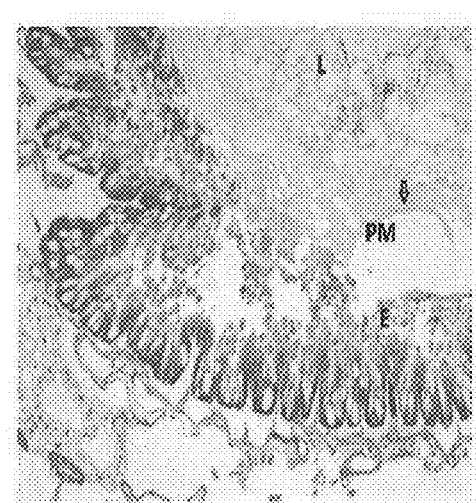

Example 12—Evaluation of the Efficacy and Effectiveness of Recombinant Chitinase BRLA_Chi 90 for Controlling *Spodoptera litura* by Droplet Feeding Insect Bioassays—a Histopathological Study of Larval Midgut Histopathology Study of Ultrastructural Changes in the Larval Midgut Following Droplet Feeding Insect Bioassays (FIGS. 20A and 20B)

Droplet feeding oral bioassays were performed on third instar larvae of *Spodoptera litura*. Thirty 3$^{rd}$ instar *S. litura* were injected with 10 µl of PBS (different concentrations of purified recombinant chitinase—10 ng, 50 ng, 0.1 ng, and 5 µg) into the hemolymph. As a negative control, thirty *S. frugiperda* larvae were also injected with PBS and the experiment was repeated three times. The inoculated larvae were placed individually in petridishes with castor leaf discs and observed twice daily until death.

Following ingestion of the chitinase by the larvae of *Spodoptera litura*, the larvae were agar embedded for cryostat sectioning as per the standard protocol. The histopathological effects of chitinase on the larval midgut demonstrated the ultrastructural changes in the midgut which include progressive loss of peritrophic membrane, sloughing of vesicular structures into the lumen and eventual lysis of midgut epithelium of the larvae leading to the death of the larvae.

Example 13—Evaluation of Antifungal Activity Against *Fusarium. Oxysporum* Using Cell Free Culture Supernatant Containing Recombinant, Modified BRLA_Chi 90

Figure 21:
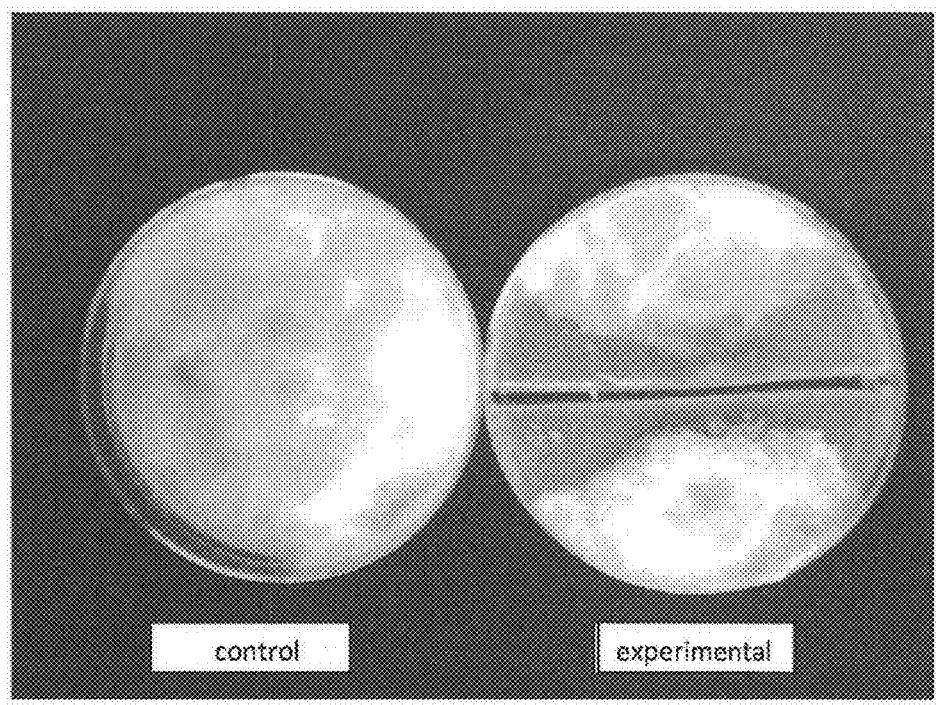

Antifungal Activity (Hyphal Extension Inhibition) Assay Showing Antagonistic Activity of Recombinant, Modified BRLA_Chi 90 Against *Fusarium oxysporum* (FIG. 21)

Antifungal plate assays were performed by a dual culture method (hyphal extension inhibition assay). The purified chitinase (2 µg/ml in 50 mM phosphate buffer, pH 6.0) was seeded in the center of a well bored Potato Dextrose agar plate and a mycelial plug of the actively growing test fungus (2 mm) was plugged on either side. The plates were incubated at 28±3° C. for 4-5 days and examined for the zones of inhibition. Antifungal activity was calculated by measuring the zone of inhibition. The percentage inhibition as calculated as Percentage Inhibition (%)=Diameter of the fungal colony on the control plate—Diameter of the fungal colony on the plate seeded with recombinant chitinase BRLA_chi90/Diameter of the fungal colony on the control×100%.

The inhibition growth zone of 36.33±1.69 mm was observed in the test plate seeded with purified chitinase. No antifungal activity was observed on the control plate.

In most cases, the antifungal activity is limited to the endochitinases. Most of the antifungal chitinases that have been reported so far are endochitinases. There are very few reports on antifungal activity of exochitinases, in particular bacterial exochitinases. Inaccessibility of exochitinases to hydrolyze fungal hyphal cell walls is not clearly evident. The strong antagonistic activity of recombinant chitinase, BRLA_Chi90 against fungal hyphae could be due to the synergistic action of exo- and endochitinase activity.

Figure 22A:
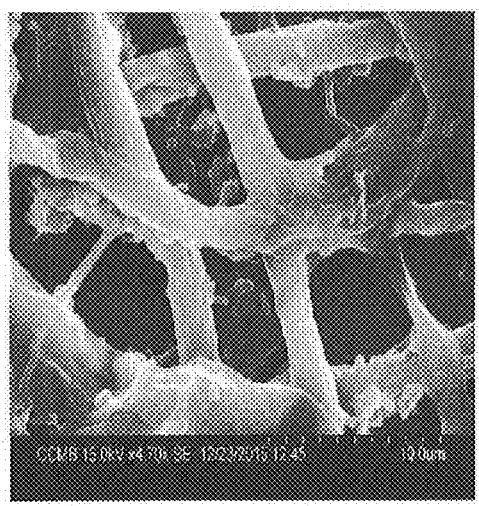
Figure 22B:
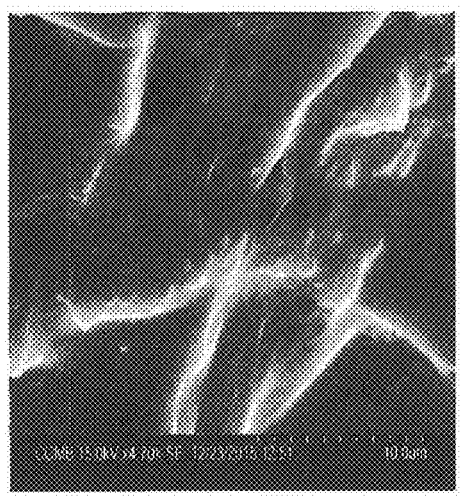
Figure 23A:
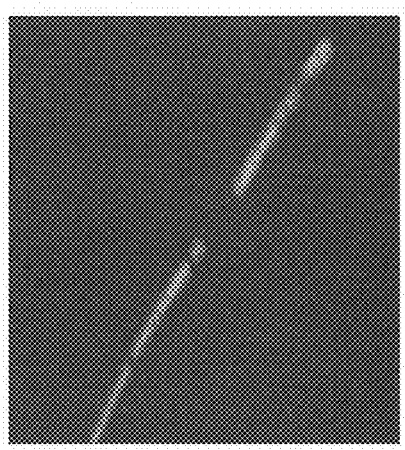
Figure 23B:
Figure 23C:
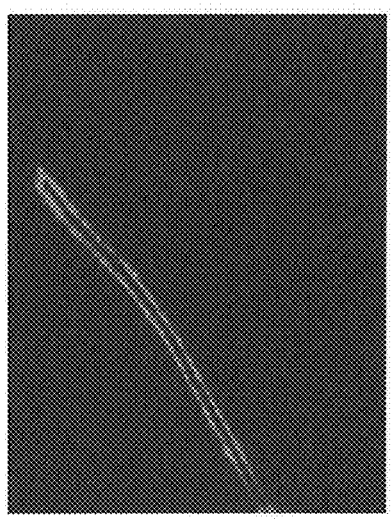
Figure 23D:
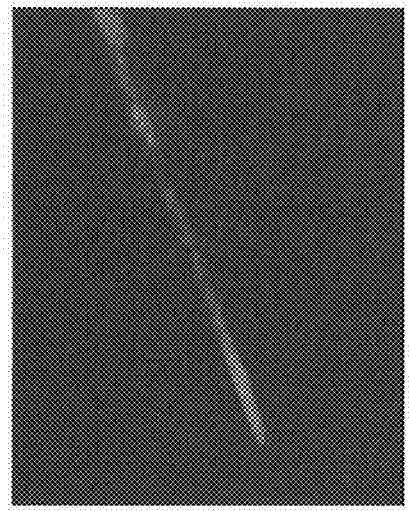

Example 14—Evaluation of Fungal Morphology of *Fusarium oxysporum* Treated with Recombinant, Modified Chitinase BRLA_Chi90 by Scanning Electron Microscopy (SEM) SEM Study of Hyphal Morphology of *Fusarium oxysporum* Treated with Recombinant Chitinase, BRLA_Chi 90 (FIGS. 22A and 22B)

Herein, *Fusarium oxysporum* was taken as a model test fungus to study the effect of recombinant chitinase, BRLA_Chi 90 on hyphal morphology by Scanning Electron Microscopy (SEM). Scanning electron microscopy (SEM) studies were carried out to reveal the morphological changes in the hyphae of phytopathogenic fungus, *Fusarium oxysporum*. The SEM studies revealed gross morphological changes in the surface structures of the treated hyphae compared to the control hyphae, indicating the degradation of the fungal cell walls.

Example 15—Evaluation of Mode Action of Chitinase and Localization of FITC-Labeled Recombinant, Modified BRLA_Chi 90 in the Hyphae of *Fusarium oxysporum* by Fluorescence Microscopy (FIGS. 23A-23D)

Figure 24A:
Figure 24B:
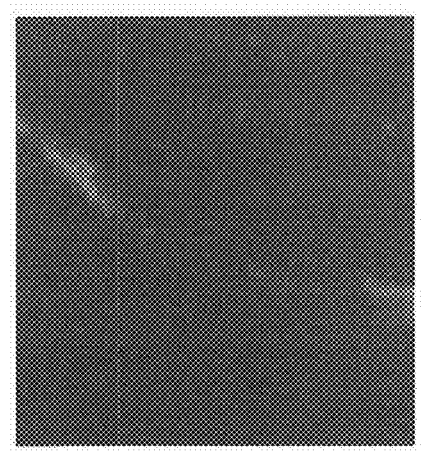

Fluorescence Microscopy Study to Evaluate Localization of FITC-BRLA_Chi 90 in the Hyphae of *Fusarium oxysporum* (FIGS. 24A and 24B)

The mode of action of recombinant chitinase was examined by fluorescent microscopy study, using FITC-labelled BRLA_Chi 90. Microscopic analysis was performed using Zeiss (Oberkochen, Germany) Axio Imager was equipped with a CCD camera and Plan Neofluar 40×(numeric aperture [NA], 1.3) and 63×(NA, 1.25) objective lenses. The excitation of fluorescently labeled proteins was carried out using an HXP metal halide lamp (LEj, Jena, Germany) in combination with a filter set for green fluorescent protein (GFP) (ET470/40BP, ET495LP, and ET525/50BP). Nascent chitin present at the apical regions of hyphae and in the inner parts of the lateral walls was more susceptible to chitinase than in the subapical parts of young hyphae but the chitinase was also found to be accumulated in the inner cortex of the mature hyphae resulting in complete destruction of the hypha, subsequently. We have observed swelling of the hyphal tips which suggested that the growth inhibition is of the consequence of a thinning of the cell wall in the hyphal tip, leading to an imbalance of turgor pressure and wall tension which causes the tip to swell and to burst.

Figure 27A:
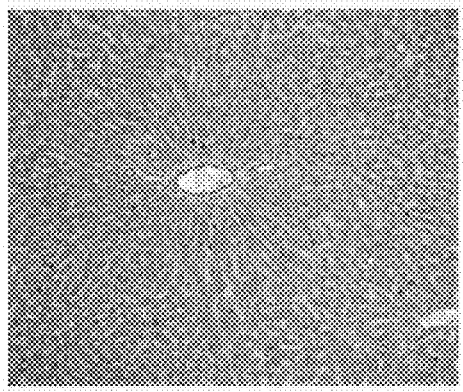
Figure 27B:
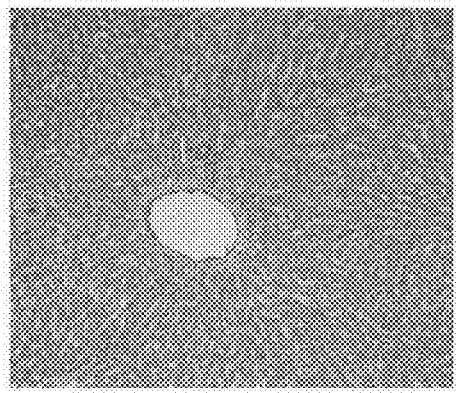
Figure 28A:
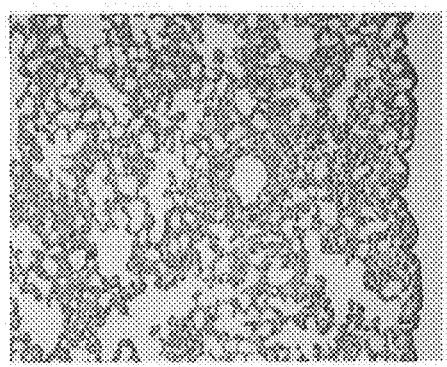
Figure 28B:
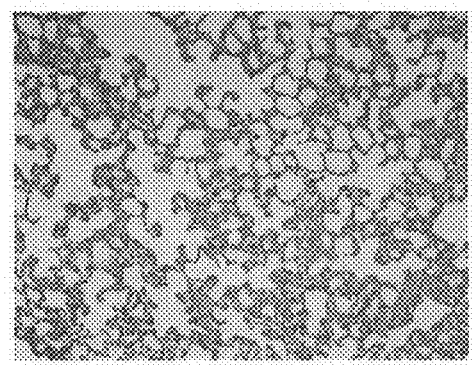
Figure 29A:
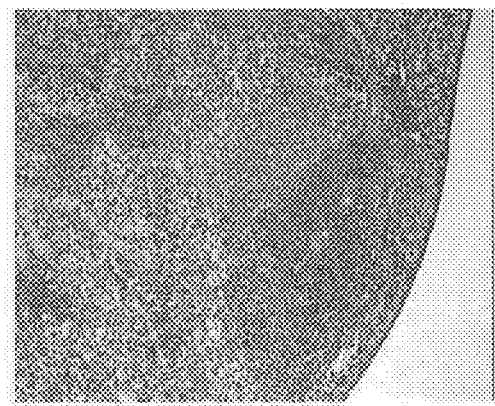
Figure 29B:
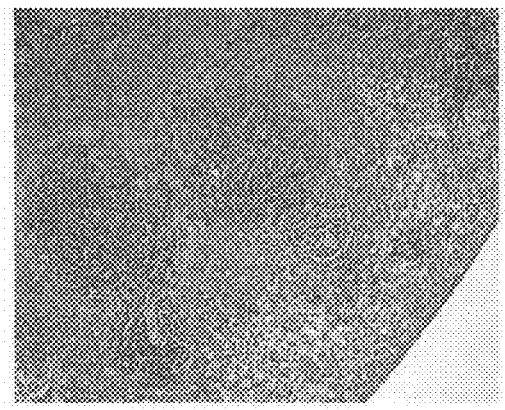

Example 16—Toxicological Studies of Recombinant, Modified Chitinase BRLA_Chi 90 from *Brevibacillus laterosporus* Lak 1210 Against Non-Target Animals Bright Field Photomicrographs of Histology of Heart in Rats (40×, H & E Stain) (FIGS. 25A and 25B)
Bright Field Photomicrographs of Histology of Kidney in Rats (40×, H & E Stain) (FIGS. 26A and 26B)
Bright Field Photomicrographs of Histology of Liver in Rats (40×, H & E Stain) (FIGS. 27A and 27B)
Bright Field Photomicrographs of Histology of Lungs in Rats (40×, H & E Stain) (FIGS. 28A and 28B)
Bright Field Photomicrographs of Histology of Spleen in Rats (40×, H & E Stain) (FIGS. 29A and 29B)

TABLE 4

Evaluation of dermal toxicity and dermal irritation in rabbits (Draize's method) - control group

| Time period (hrs/d) | Erythema score | | | Edema score | | |
|---|---|---|---|---|---|---|
| | Rabbits 1 2 3 | Average score | Combined index | Rabbits 1 2 3 | Average score | Combined index |
| 1 h  | 0 0 0 | 0 | 0 | 0 0 0 | 0 | 0 |
| 24 h | 0 0 0 | 0 | 0 | 0 0 0 | 0 | 0 |
| 48 h | 0 0 0 | 0 | 0 | 0 0 0 | 0 | 0 |
| 72 h | 0 0 0 | 0 | 0 | 0 0 0 | 0 | 0 |
| 7 d  | 0 0 0 | 0 | 0 | 0 0 0 | 0 | 0 |
| 14 d | 0 0 0 | 0 | 0 | 0 0 0 | 0 | 0 |

Primary irritation index: 0.0-1 non-irritant; 1.1-2 slightly irritant; 2.1-5 moderately irritant; 5.1-6 severe moderated irritant; 6.1-8 severe irritant.

TABLE 5

Evaluation of dermal toxicity and dermal irritation in rabbits (Draize's method) - Experimental group tested with the sample, culture supernatant containing chitinase

| Time period (hrs/d) | Erythema score | | | Edema score | | |
|---|---|---|---|---|---|---|
| | Rabbits 1 2 3 | Average score | Combined index | Rabbits 1 2 3 | Average score | Combined index |
| 1 h  | 0 0 0 | 0 | 0 | 0 0 0 | 0 | 0 |
| 24 h | 0 0 0 | 0 | 0 | 0 0 0 | 0 | 0 |
| 48 h | 0 0 0 | 0 | 0 | 0 0 0 | 0 | 0 |
| 72 h | 0 0 0 | 0 | 0 | 0 0 0 | 0 | 0 |
| 7 d  | 0 0 0 | 0 | 0 | 0 0 0 | 0 | 0 |
| 14 d | 0 0 0 | 0 | 0 | 0 0 0 | 0 | 0 |

Primary irritation index: 0.0-1 non-irritant; 1.1-2 slightly irritant; 2.1-5 moderately irritant; 5.1-6 severe moderated irritant; 6.1-8 severe irritant.

A new strain, *Brevibacillus laterosporus* LAK 1210 has been proposed for use in insect control and it has already been demonstrated that it is effective biocontrol agent. It is absolutely necessary that the biocontrol strain of *Brevibacillus laterosporus* and its chitinase enzyme formulations which is purported to be used in agricultural fields, horticulture farms, forests, forest nurseries is evaluated for interim risk assessment towards non-target animals. The toxicological studies were performed to prove the safety in application of formulations of chitinase enzyme and/or cell suspensions of *Brevibacillus laterosporus* LAK 1210 as a contact and stomach biopesticide.

Acute oral toxicity and pathogenicity of chitinase formulations of *Brevibacillus laterosporus* LAK 1210 and to generate preliminary toxicology data for the development of a next generation, potential biopesticide as a possible alternative to Bt and paves a way for its commercialization. Low or non-existing toxicity of the enzyme supernatant and cell suspensions of *Brevibacillus laterosporus* LAK 1210 through three different toxicity studies in animal models, such as acute oral toxicity in a murine model (adult Wistar rats) and a dermal irritation test in rabbits.

On the basis of these results, it was concluded that the chitinase formulations can contribute to the development of a "low risk" biopesticide.

A. Acute Oral Toxicity Test Using Murine Models (Wistar Rats)

The acute oral toxicity test was conducted according to United States Environmental Protection Agency (USEPA) guidelines. This study was conducted on twelve female albino Wistar rats, 7-8-week-old with a body weight between 150 and 200 g, obtained from the Central Animal Facility, CCMB, INDIA. They were kept in individual polypropylene cages provided with clean bedding of rice husk. They were divided into four groups (three experimental groups and one control group). They were acclimatized for five days prior to dosing under standard housing conditions (temperature: 25±2° C., relative humidity: between 30 and 70% with optimal air changes per hour and 12 h each of dark and light cycle) and provided with standard pelleted feed and U.V. treated water ad libitum.

The animals were acclimatized to the laboratory conditions 5 days prior to the test. The control group was administered sterile PBS. Each of the animal in the three experimental groups was administered two concentrations (5, 10 and 20 mg/kg) of lyophilized extracts of the culture supernatant containing chitinase enzyme. Oral administration was performed by gavage for all the animals. The body weight of each animal was registered on day one of acclimatization, before dosing beginning on the first day of the study and then twice a week for a period of 14 days. During this period, food and water consumption were also registered. At the end of the study, the average gain in weight in grams per day as well as the average of solids and liquids consumed per day was obtained in grams or milliliters. Body weight of individual animals were recorded on the day of dosing, weekly thereafter, twice a week and at termination on day 14.

The treated animals were observed for mortality (twice daily) and clinical signs were recorded to note the onset, duration and reversal (if any) of toxic effects at 1, 2, 4, 8 and 12 h after the administration of the test substance and once daily thereafter for 14 days. The routine cage side observations included changes in skin and fur, eyes respiration, occurrence of secretions and bizarre behavior (e.g. self-mutilation, walking backwards). The behavioral profile studied included alertness, visual placing, irritability, spontaneous activity, reactivity and touch response, whereas neurological observations such as straub response, tremors, convulsions, staggering gait, limb tone, grip strength, corneal reflex and pinna reflex were taken into consideration. The criteria for autonomic profile included findings on pupil size, palpebral opening, exophthalmos, salivation, piloerection. Miscellaneous signs like arching of the back, alopecia, wound, nasal discharge, lacrimation and loose stool were also recorded during the observations. The clinical signs were graded by a scoring system wherein scores for normal, abnormal, subnormal and supernormal responses were assigned as 4, 0, <4 and >4, respectively and the maximum score for any response was assigned as 8.

At the end of the study, one animal per group was selected and a macroscopic necropsy was performed, and the gross pathological changes, if any, were recorded, including examination of the outer surface of the body, all holes and cranial, thoracic and abdominal cavities. The morphological characteristics of the heart, kidney, spleen and liver were also assessed. Histopathological examination of liver, kidney, heart, spleen and lungs was considered. The organs were removed, fixed in 10% neutral buffered formalin and processed for paraffin embedding. Sections of 4-6 µm thickness were cut and stained with hematoxylin and eosin (H and E) and observed under light microscope for histopathological changes.

The treated animals survived throughout the study period and did not reveal any treatment related major abnormal clinical signs or any significant pathological changes at the tested dose levels. On necropsy, no abnormalities in the organs were observed in any of the treated animals. There were no statistical differences in body weight gain between controls and tested groups during the 14-day observation period. The behavioral, neurological and autonomic parameters recorded in terms of graded scores in the treated animals, immediately after the administration of the chitinase formulations/cell suspensions and daily once during the observation period of 14 days, were well within the normal levels. The gross necroscopy showed no significant changes in the organs like heart, liver, kidney, spleen and lungs with respect to control (FIGS. 25A, 25B, 26A, 26B, 27A, 27B, 28A, 28B, 29A and 29B).

A. Evaluation of Irritation Tests on Rabbits by Draize's Method

The Draize's skin test was used to evaluate dermal irritation in rabbits. The extracts and cell cultures were administered on the first day of the study. For each concentration, two rabbits were used applying a single solution directly on the back with the help of a sterile cotton swab. After application, a patch of surgical gauze with 4 layers and an elastic bandage were fixed thereon in order to prevent the animal from accessing the site where the test substances were applied. The total observation period lasted 72 h and special attention was given to signs of edema and erythema at 4, 24, 48 and 72 h after removing the patches (using the value scale for skin lesions as described by Draize's).

The erythema values were averaged and added to the edema values (eqn 1) to calculate the Dermal irritation index (DII).

$$\text{Primary dermal irritation index} = \bar{x} \text{ of erythema} + \bar{x} \text{ of edema} \quad \text{(Eqn 1)}$$

Based on this index for primary dermal irritation, values between 0 and 5 are considered to be within the acceptance criteria for the safe use of these extracts and cells on humans. When values range from 6 to 8, the product cannot be utilized on human skin due to it being considered as an irritant.

In the present example, 0.5 ml of the test sample (culture supernatant containing chitinase at a concentration of 1 mg/ml) (Test) and sterile 1×PBS (control) was applied to the skin of albino rabbits. After 4 hours i.e. the exposure period, the degree of irritation was read and scored at 1 h, 24 h, 48 h, 72 h, 7 and 14 days after the patch removal.

The primary skin irritation index was calculated and came as 0.00 after patch removal. Hence, it was concluded that the both the control sample (PBS) and the test sample (culture supernatant containing chitinase) was 'non-irritant' to the skin of rabbits.

Control sample (0.5 ml sterile PBS) was evenly applied to a small area (approximately 6 cm square) of the closely clipped skin of each of three rabbits. The site of application was covered with a cotton another three rabbits were similarly treated with 0.5 ml of the test sample of culture supernatant containing chitinase (1 mg/ml). At the termination of 4 h exposure period, the bandages/gauze was removed and treatment sites were cleaned with wet gauze to remove any residual test substance.

Skin reaction at the site of application was subjectively assessed and scored once daily at 1 h, 24 h, 48 h, 72 h; 7 and 14 days after patch removal (post-test observation period) according to Draize's method.

The reaction at the site of application was assessed and scored according to the following numerical system (Table 4 and 5).

Example 17—Demonstration of Insecticidal Activity of Recombinant, Modified Chitinase BRLA_Chi 90 from *Brevibacillus laterosporus* Lak 1210 Against * combined synergistic effect of the exo- and endochitinase activity of the enzyme. The mortality percentages obtained were 10.9 to 100%, depending upon the concentration (μg/ml)–contact time (h).

TABLE 7

Mortality (%) of Spodoptera litura against concentration of recombinant, modified chitinase, BRLA_Chi 90 (μg/ml) - contact time (h)

| Concentration(μg/ml) | 1 h | 12 h | 24 h | 48 h |
|---|---|---|---|---|
| 0 (control) | 0 | 2.6 ± 0.6 | 4.1 ± 0.12 | 5.3 ± 0.31 |
| 5 | 9.6 ± 0.39 | 31.1 ± 0.65 | 38.2 ± 0.88 | 50.72 ± 1.12 |
| 10 | 51.7 ± 1.21 | 62.4 ± 1.45 | 79.6 ± 1.53 | 98 ± 2.20 |
| 15 | 69.2 ± 1.42 | 84.4 ± 1.78 | 95.4 ± 2.02 | 100 ± 2.50 |
| 20 | 84.5 ± 1.78 | 100 ± 2.50 | 100 ± 2.50 | 100 ± 2.50 |
| 25 μg | 100 ± 2.50 | 100 ± 2.50 | 100 ± 2.50 | 100 ± 2.50 |

Example 18—Demonstration of Insecticidal Activity of Recombinant, Modified Chitinase BRLA_Chi 90 from Brevibacillus laterosporus Lak 1210 Against Third Instar Larvae of Spodoptera litura by Diet Inorporation Bioassays Insecticidal activity of recombinant, modified chitinase, BRLA_Chi 90 toward the insect pest, *Spodoptera litura* was demonstrated by diet incorporation (ingestion) bioassays. The baseline bioassay was performed using thirty, $3^{rd}$ instar larvae of *Spodoptera litura* reared in the laboratory. The larvae were fed on chitinase-integrated chickpea based semi-synthetic diet infested with culture supernatant containing recombinant, modified chitinase added to the diet, at concentration (1.5, 6.0, 24, 48 and 96 μg/g diet) with 50 mM phosphate buffer (pH 6.0) as a control. The larvae were placed in 24 well, tissue culture plate, each larva in a separate well and the plates were incubated at 25° C. with 80% relative humidity. The mortality and the larval weight were recorded and the dead larvae were scored at 1, 24, 48, after treatment. Probit analysis was done to determine the $LC_{50}$ values, taking into account, the natural mortality and the statistical analyses of the data was done using R package, a web based tool. The results indicate that the recombinant, modified chitinase, BRLA_Chi 90 had an effective, insecticidal action upon ingestion. The recombinant, modified chitinase, BRLA_Chi 90 enters the gut of the larvae and causes damage to the peritrophic membrane that lines the midgut, thus preventing the larvae from feeding, consequently resulting in its death. The alkaline activity of the recombinant, modified enzyme, BRLA_Chi 90 with a pH optimum of 9.0, promotes faster lysis of midgut epithelium following the formation of pores and destruction of the peritrophic membrane. The alkaline activity of the recombinant, modified chitinase also helps in efficient synergistic action to potentiate the effect of cry toxins, when it is used along with the Bt-biopesticides.

TABLE 8

$LC_{50}$ and $LC_{90}$ values in μg/g diet (95 ± CL) for different time periods for third instar larvae of *Spodoptera litura* when fed with culture supernatant comprising recombinant, modified chitinase, BRLA_Chi 90

| Treatment | Time (h) | $LC_{50}$ (95% limits) | Time (h) | $LC_{90}$ (95% limits) |
|---|---|---|---|---|
| Culture supernatant containing recombinant, modified chitinase, BRLA_Chi 90 | 24 | 36.6 (25.7-43.2) | 24 | — |
| | 48 | 18.9(12.9-22.5) | 48 | 61.8(48.1-72.8) |

Lethal concentrations were not estimated as it would have required notable extrapolation of the recorded data.

The invention claimed is:

1. A recombinant modified nucleic acid comprising the nucleotide sequence of SEQ ID NO: 3, wherein the native chitinase-encoding nucleic sequence of SEQ ID NO: 1 has been modified at positions 661 and 2158 to obtain the recombinant modified nucleic acid.

2. A recombinant modified nucleic acid encoding the recombinant modified chitinase comprising the amino acid sequence of SEQ ID NO:4.

3. A DNA construct comprising the recombinant modified nucleic acid as claimed in claim 1, wherein the nucleic acid is operably linked to a T7 promoter.

4. A vector comprising the DNA construct as claimed in claim 3.

5. The vector as claimed in claim 4, wherein the vector is pET/BRLA_Chi90 vector.

6. A recombinant host cell comprising the vector as claimed in claim 4.

7. The recombinant host cell as claimed in claim 6, wherein the host cell is selected from *Escherichia coli*, *Bacillus subtilis*, *Pseudomonas putida*, *Corynebacterium glutamicum*, *Saccharomyces cerevisiae*, *Pichia pastoris* and *Hansenula* polymorphs.

8. The recombinant host cell as claimed in claim 6, wherein the recombinant host cell is *Escherichia coli* (BL21DE3).

9. A process for preparation of a recombinant modified chitinase, said process comprising the steps of:
   a. culturing the recombinant host cell as claimed in claim 6;
   b. harvesting a cell lysate or a culture supernatant; and
   c. purifying the recombinant modified chitinase from the cell lysate or the culture supernatant by chitin affinity chromatography or chitin adsorption affinity chromatography.

10. The process as claimed in claim 9, wherein chitin affinity chromatography comprises the steps of:
   a. loading the cell lysate in chromatographic columns packed with chitin beads;
   b. eluting bound proteins with 20 mM Tris HCl (8.0); and
   c. eluting the recombinant modified chitinase stepwise with 0.5 M, 0.1 M and 20 mM acetic acid.

11. The process as claimed in claim 9, wherein chitin adsorption affinity chromatography comprises the steps of:
   a. loading the culture supernatant comprising the recombinant modified chitinase in chromatographic columns packed with powdered crustacean shells, wherein the crustacean shells are crab shells and shrimp shells;
   b. eluting bound proteins with 20 mM Tris HCl (8.0); and
   c. eluting the recombinant modified chitinase stepwise with 0.5 M, 0.1 M and 20 mM acetic acid.

* * * * *

SEQUENCE LISTING

```
<160> NUMBER OF SEQ ID NOS: 40

<210> SEQ ID NO 1
<211> LENGTH: 2583
<212> TYPE: DNA
<213> ORGANISM: Brevibacillus laterosporus LAK1210 (MTCC5487)

<400> SEQUENCE: 1
atgagaaaga tgtatcaaca cattcctact gctcattcag tcagaaaatt caatttcttg      60
ttgttagcct tcgttctttt tgcaagtatt ttcccggcta ttctaccagc tagcgtttct     120
gcttcgccga tctgctcagc tgtctgggat agtaaaacaa tttacaccag tggacaacaa     180
gcttcctaca agggtcatga atggacagca aaatggtgga cacagggtga agagccaggt     240
accagtgatg tgtggcagga tcttggcgtt tgctctacta atcccactaa tccacctgat     300
ccttctaata ctcctcctac ggtacctacc aatctagctg taacagcaaa aacctccaca     360
agtgtttctc tcacatgggc tgcttctacc gatgataagc aagtgatagg ctatacggtt     420
tattataacg ataatttgca agcggttaca caaaccaatg ctacgatcac caatctaatt     480
cccaatacca cttacacatt tacagtaaaa gcaaaagaca atcaaggctt ggagtctgag     540
gctagtcaac cgttaaaagt cactacagat acagacactt taccacctga gccagccact     600
ccttgccgtc cagccggtct atatgattct ggcgtaaaaa acattcctta ttgccaagca     660
```

-continued

```
tatgatcagg atggacgtga aaagctagcc aatgattcta aacgacgaat aattggctac      720
tttacaagct ggagaacggg gaaaaatgga caatccaaat atttagtcac cgatattccg      780
tggaaaaacc taacacatat caactacgct tttgcacatg ttgacagtaa taaccgcgta      840
tctgttggtt cccccactga tccaaccaat ccagcgctag gcttaacttg gccagagtat      900
cccgatgccc taatggaccc atccctgcca tataaaggac acttcaatct gctaacacag      960
tggaagaaaa aaaatcctgg tgtaaaaacc cttgtttccg ttggaggatg ggctgaatca     1020
ggaggatata ttgatgagaa tggaaagcga attgcttctg gaggcttttta cacgatgacg     1080 actaatgcag atggctccgt caatcaagcg gcaattgaca cattcgctac ctctgctgtt     1140 gatttttac gcaaatataa ttttgaagga atcgacatcg actacgaata cccaactaca     1200
atgaaccaag ccggtaatcc attagattgg caattttcca ctcctcgctt aaaaggacta     1260
atggaaggct ataacgcctt gttaaaaacc ttgcgagtca agctggatca agcatctgct     1320
gaggacgaaa atattacat gctaaccata gcctcaccct tctctgccta tttgttgcgt     1380
ggaatggagt cttttccaagc tttgaagtat ctcgactatg tgaatgtgat gtcctatgat     1440
cttcacgggg cttggaatga attcgttggt cctaatgctg cattatttga tgatggcaag     1500
gatggagagt taattaaata taacatttat aacacgcctc aatatggcgg cattggctac     1560
ctcaatacag attgggctta ccattacatg cgtgggatga tgcaggcagg acgaatcaac     1620
atcggagttc cctattatac tcgtggcttt caaaatgttg tgggaggaac agatgggcta     1680
tggggaaaag ctgtaggtaa aaattgccca actggactaa ccgcttgcgg ggatggcgcc     1740
acaggtattg ataacatctg gcatgataaa gatgagaatg gcaaagagga aggggcaggc     1800
tcaaatccaa tgtggcatgc caaaaatctc gaaaagggca ttgctggctc ctatttgaag     1860
gatcatggga ttgtaaatcc agtgttgact ggtacctata agcgtaacta tgattctact     1920
cttgttgccc catggctttg gaatgctgag aagagggttt ttctatctac tgaggatgaa     1980
caatctatcg gcgccaaagc agattatgtt ataaaaaatg ggattggcgg cattatgatt     2040
tgggaattgg caggtgacta cgactggtac aaggatcgca atgacggtaa aggagaatac     2100
tacatgggtt ctactttaac caaattgatg cataggaaat tttcaacagc aaccccatat     2160
gatgcttcaa atagtaaaac cccgctacca gccgataaac tagccctaaa aatagaagtc     2220
actggctttc aactaggaga tcaaaactat ccaatcaatc ctacgctaaa aataaccaat     2280
aacagtaatc taactatcac aggcggctcc gtcattgagt tcgatgttcc tacttctacc     2340
tcagcccaat ttagtagcta tggcggggat agtgttaaaa taatctctgc tggtcatacg     2400
gggccaaacg tcggtggatt aaagggtgat tttcaccgtg tggcagtcac cattcctact     2460
tggaaatcag tagcgcctgg acaaagcata gatatgagca tcgtttatta cgtgcctatt     2520
agcggtccta caaattatac cattacaatt gacggcaaaa aatatgcggt tactgataag     2580
taa                                                                   2583
```

<210> SEQ ID NO 2
<211> LENGTH: 860
<212> TYPE: PRT
<213> ORGANISM: Brevibacillus laterosporus LAK1210 (MTCC5487)

<400> SEQUENCE: 2

```
Met Arg Lys Met Tyr Gln His Ile Pro Thr Ala His Ser Val Arg Lys
1               5                   10                  15

Phe Asn Phe Leu Leu Leu Ala Phe Val Leu Phe Ala Ser Ile Phe Pro
```

```
            20                  25                  30
Ala Ile Leu Pro Ala Ser Val Ser Ala Ser Pro Ile Cys Ser Ala Val
            35                  40                  45

Trp Asp Ser Lys Thr Ile Tyr Thr Ser Gly Gln Gln Ala Ser Tyr Lys
 50                  55                  60

Gly His Glu Trp Thr Ala Lys Trp Trp Thr Gln Gly Glu Glu Pro Gly
 65                  70                  75                  80

Thr Ser Asp Val Trp Gln Asp Leu Gly Val Cys Ser Thr Asn Pro Thr
                 85                  90                  95

Asn Pro Pro Asp Pro Ser Asn Thr Pro Pro Thr Val Pro Thr Asn Leu
            100                 105                 110

Ala Val Thr Ala Lys Thr Ser Thr Ser Val Ser Leu Thr Trp Ala Ala
            115                 120                 125

Ser Thr Asp Asp Lys Gln Val Ile Gly Tyr Thr Val Tyr Tyr Asn Asp
            130                 135                 140

Asn Leu Gln Ala Val Thr Gln Thr Asn Ala Thr Ile Thr Asn Leu Ile
145                 150                 155                 160

Pro Asn Thr Thr Tyr Thr Phe Thr Val Lys Ala Lys Asp Asn Gln Gly
                165                 170                 175

Leu Glu Ser Glu Ala Ser Gln Pro Leu Lys Val Thr Thr Asp Thr Asp
            180                 185                 190

Thr Leu Pro Pro Glu Pro Ala Thr Pro Cys Arg Pro Ala Gly Leu Tyr
            195                 200                 205

Asp Ser Gly Val Lys Asn Ile Pro Tyr Cys Gln Ala Tyr Asp Gln Asp
            210                 215                 220

Gly Arg Glu Lys Leu Ala Asn Asp Ser Lys Arg Ile Ile Gly Tyr
225                 230                 235                 240

Phe Thr Ser Trp Arg Thr Gly Lys Asn Gly Gln Ser Lys Tyr Leu Val
                245                 250                 255

Thr Asp Ile Pro Trp Lys Asn Leu Thr His Ile Asn Tyr Ala Phe Ala
            260                 265                 270

His Val Asp Ser Asn Asn Arg Val Ser Val Gly Ser Pro Thr Asp Pro
            275                 280                 285

Thr Asn Pro Ala Leu Gly Leu Thr Trp Pro Glu Tyr Pro Asp Ala Leu
            290                 295                 300

Met Asp Pro Ser Leu Pro Tyr Lys Gly His Phe Asn Leu Leu Thr Gln
305                 310                 315                 320

Trp Lys Lys Lys Asn Pro Gly Val Lys Thr Leu Val Ser Val Gly Gly
                325                 330                 335

Trp Ala Glu Ser Gly Gly Tyr Ile Asp Glu Asn Gly Lys Arg Ile Ala
            340                 345                 350

Ser Gly Gly Phe Tyr Thr Met Thr Thr Asn Ala Asp Gly Ser Val Asn
            355                 360                 365

Gln Ala Ala Ile Asp Thr Phe Ala Thr Ser Ala Val Asp Phe Leu Arg
            370                 375                 380

Lys Tyr Asn Phe Glu Gly Ile Asp Ile Asp Tyr Glu Tyr Pro Thr Thr
385                 390                 395                 400

Met Asn Gln Ala Gly Asn Pro Leu Asp Trp Gln Phe Ser Thr Pro Arg
                405                 410                 415

Leu Lys Gly Leu Met Glu Gly Tyr Asn Ala Leu Leu Lys Thr Leu Arg
            420                 425                 430

Val Lys Leu Asp Gln Ala Ser Ala Glu Asp Glu Lys Tyr Tyr Met Leu
            435                 440                 445
```

Thr Ile Ala Ser Pro Ser Ser Ala Tyr Leu Leu Arg Gly Met Glu Ser
    450                 455                 460

Phe Gln Ala Leu Lys Tyr Leu Asp Tyr Val Asn Val Met Ser Tyr Asp
465                 470                 475                 480

Leu His Gly Ala Trp Asn Glu Phe Val Gly Pro Asn Ala Ala Leu Phe
                485                 490                 495

Asp Asp Gly Lys Asp Gly Glu Leu Ile Lys Tyr Asn Ile Tyr Asn Thr
            500                 505                 510

Pro Gln Tyr Gly Gly Ile Gly Tyr Leu Asn Thr Asp Trp Ala Tyr His
        515                 520                 525

Tyr Met Arg Gly Met Met Gln Ala Gly Arg Ile Asn Ile Gly Val Pro
    530                 535                 540

Tyr Tyr Thr Arg Gly Phe Gln Asn Val Val Gly Gly Thr Asp Gly Leu
545                 550                 555                 560

Trp Gly Lys Ala Val Gly Lys Asn Cys Pro Thr Gly Leu Thr Ala Cys
                565                 570                 575

Gly Asp Gly Ala Thr Gly Ile Asp Asn Ile Trp His Asp Lys Asp Glu
            580                 585                 590

Asn Gly Lys Glu Glu Gly Ala Gly Ser Asn Pro Met Trp His Ala Lys
        595                 600                 605

Asn Leu Glu Lys Gly Ile Ala Gly Ser Tyr Leu Lys Asp His Gly Ile
    610                 615                 620

Val Asn Pro Val Leu Thr Gly Thr Tyr Lys Arg Asn Tyr Asp Ser Thr
625                 630                 635                 640

Leu Val Ala Pro Trp Leu Trp Asn Ala Glu Lys Arg Val Phe Leu Ser
                645                 650                 655

Thr Glu Asp Glu Gln Ser Ile Gly Ala Lys Ala Asp Tyr Val Ile Lys
            660                 665                 670

Asn Gly Ile Gly Gly Ile Met Ile Trp Glu Leu Ala Gly Asp Tyr Asp
        675                 680                 685

Trp Tyr Lys Asp Arg Asn Asp Gly Lys Gly Glu Tyr Tyr Met Gly Ser
    690                 695                 700

Thr Leu Thr Lys Leu Met His Arg Lys Phe Ser Thr Ala Thr Pro Tyr
705                 710                 715                 720

Asp Ala Ser Asn Ser Lys Thr Pro Leu Pro Ala Asp Lys Leu Ala Leu
                725                 730                 735

Lys Ile Glu Val Thr Gly Phe Gln Leu Gly Asp Gln Asn Tyr Pro Ile
            740                 745                 750

Asn Pro Thr Leu Lys Ile Thr Asn Asn Ser Asn Leu Thr Ile Thr Gly
        755                 760                 765

Gly Ser Val Ile Glu Phe Asp Val Pro Thr Ser Thr Ser Ala Gln Phe
    770                 775                 780

Ser Ser Tyr Gly Gly Asp Ser Val Lys Ile Ile Ser Ala Gly His Thr
785                 790                 795                 800

Gly Pro Asn Val Gly Gly Leu Lys Gly Asp Phe His Arg Val Ala Val
                805                 810                 815

Thr Ile Pro Thr Trp Lys Ser Val Ala Pro Gly Gln Ser Ile Asp Met
            820                 825                 830

Ser Ile Val Tyr Tyr Val Pro Ile Ser Gly Pro Thr Asn Tyr Thr Ile
        835                 840                 845

Thr Ile Asp Gly Lys Lys Tyr Ala Val Thr Asp Lys
    850                 855                 860

<210> SEQ ID NO 3
<211> LENGTH: 2583
<212> TYPE: DNA
<213> ORGANISM: Brevibacillus laterosporus LAK1210 (MTCC5487)

<400> SEQUENCE: 3

| | | | | | |
|---|---|---|---|---|---|
| atgagaaaga | tgtatcaaca | cattcctact | gctcattcag | tcagaaaatt | caatttcttg | 60 |
| ttgttagcct | tcgttctttt | tgcaagtatt | ttcccggcta | ttctaccagc | tagcgtttct | 120 |
| gcttcgccga | tctgctcagc | tgtctgggat | agtaaaacaa | tttacaccag | tggacaacaa | 180 |
| gcttcctaca | agggtcatga | atggacagca | aaatggtgga | cacagggtga | agagccaggt | 240 |
| accagtgatg | tgtggcagga | tcttggcgtt | tgctctacta | atcccactaa | tccacctgat | 300 |
| ccttctaata | ctcctcctac | ggtacctacc | aatctagctg | taacagcaaa | aacctccaca | 360 |
| agtgtttctc | tcacatgggc | tgcttctacc | gatgataagc | aagtgatagg | ctatacggtt | 420 |
| tattataacg | ataatttgca | agcggttaca | caaaccaatg | ctacgatcac | caatctaatt | 480 |
| cccaatacca | cttacacatt | tacagtaaaa | gcaaaagaca | atcaaggctt | ggagtctgag | 540 |
| gctagtcaac | cgttaaaagt | cactacagat | acagacactt | taccacctga | gccagccact | 600 |
| ccttgccgtc | cagccggtct | atatgattct | ggcgtaaaaa | acattcctta | ttgccaagca | 660 |
| catgatcagg | atggacgtga | aaagctagcc | aatgattcta | aacgacgaat | aattggctac | 720 |
| tttacaagct | ggagaacggg | gaaaaatgga | caatccaaat | atttagtcac | cgatattccg | 780 |
| tggaaaaacc | taacacatat | caactacgct | tttgcacatg | ttgacagtaa | taaccgcgta | 840 |
| tctgttggtt | cccccactga | tccaaccaat | ccagcgctag | gcttaacttg | gccagagtat | 900 |
| cccgatgccc | taatggaccc | atccctgcca | tataaaggac | acttcaatct | gctaacacag | 960 |
| tggaagaaaa | aaaatcctgg | tgtaaaaacc | cttgtttccg | ttggaggatg | ggctgaatca | 1020 |
| ggaggatata | ttgatgagaa | tggaaagcga | attgcttctg | gaggctttta | cacgatgacg | 1080 |
| actaatgcag | atggctccgt | caatcaagcg | gcaattgaca | cattcgctac | ctctgctgtt | 1140 |
| gatttttac | gcaaatataa | ttttgaagga | atcgacatcg | actacgaata | cccaactaca | 1200 |
| atgaaccaag | ccggtaatcc | attagattgg | caattttcca | ctcctcgctt | aaaaggacta | 1260 |
| atggaaggct | ataacgccct | tgttaaaaacc | ttgcgagtca | agctggatca | agcatctgct | 1320 |
| gaggacgaaa | aatattacat | gctaaccata | gcctcacctt | cttctgccta | tttgttgcgt | 1380 |
| ggaatggagt | ctttccaagc | tttgaagtat | ctcgactatg | tgaatgtgat | gtcctatgat | 1440 |
| cttcacgggg | cttggaatga | attcgttggt | cctaatgctg | cattatttga | tgatggcaag | 1500 |
| gatggagagt | taattaaata | taacatttat | aacacgcctc | aatatggcgg | cattggctac | 1560 |
| ctcaatacag | attgggctta | ccattacatg | cgtgggatga | tgcaggcagg | acgaatcaac | 1620 |
| atcggagttc | cctattatac | tcgtggcttt | caaaatgttg | tgggaggaac | agatgggcta | 1680 |
| tggggaaaag | ctgtaggtaa | aaattgccca | actggactaa | ccgcttgcgg | ggatggcgcc | 1740 |
| acaggtattg | ataacatctg | gcatgataaa | gatgagaatg | gcaaagagga | aggggcaggc | 1800 |
| tcaaatccaa | tgtggcatgc | caaaaatctc | gaaaagggca | ttgctggctc | ctatttgaag | 1860 |
| gatcatggga | ttgtaaatcc | agtgttgact | ggtacctata | gcgtaactaa | tgattctact | 1920 |
| cttgttgccc | catggctttg | gaatgctgag | aagagggttt | ttctatctac | tgaggatgaa | 1980 |
| caatctatcg | gcgccaaagc | agattatgtt | ataaaaaatg | ggattggcgg | cattatgatt | 2040 |
| tgggaattgg | caggtgacta | cgactggtac | aaggatcgca | atgacggtaa | aggagaatac | 2100 |
| tacatgggtt | ctactttaac | caaattgatg | cataggaaat | tttcaacagc | aaccccacat | 2160 |

```
gatgcttcaa atagtaaaac cccgctacca gccgataaac tagccctaaa aatagaagtc    2220
actggctttc aactaggaga tcaaaactat ccaatcaatc ctacgctaaa aataaccaat    2280
aacagtaatc taactatcac aggcggctcc gtcattgagt tcgatgttcc tacttctacc    2340
tcagcccaat ttagtagcta tggcggggat agtgttaaaa taatctctgc tggtcatacg    2400
gggccaaacg tcggtggatt aaagggtgat tttcaccgtg tggcagtcac cattcctact    2460
tggaaatcag tagcgcctgg acaaagcata gatatgagca tcgtttatta cgtgcctatt    2520
agcggtccta caaattatac cattacaatt gacggcaaaa aatatgcggt tactgataag    2580
taa                                                                 2583
```

<210> SEQ ID NO 4
<211> LENGTH: 860
<212> TYPE: PRT
<213> ORGANISM: Brevibacillus laterosporus LAK1210 (MTCC5487)

<400> SEQUENCE: 4

```
Met Arg Lys Met Tyr Gln His Ile Pro Thr Ala His Ser Val Arg Lys
1               5                   10                  15

Phe Asn Phe Leu Leu Leu Ala Phe Val Leu Phe Ala Ser Ile Phe Pro
            20                  25                  30

Ala Ile Leu Pro Ala Ser Val Ser Ala Ser Pro Ile Cys Ser Ala Val
        35                  40                  45

Trp Asp Ser Lys Thr Ile Tyr Thr Ser Gly Gln Gln Ala Ser Tyr Lys
    50                  55                  60

Gly His Glu Trp Thr Ala Lys Trp Trp Thr Gln Gly Glu Glu Pro Gly
65                  70                  75                  80

Thr Ser Asp Val Trp Gln Asp Leu Gly Val Cys Ser Thr Asn Pro Thr
                85                  90                  95

Asn Pro Pro Asp Pro Ser Asn Thr Pro Pro Thr Val Pro Thr Asn Leu
            100                 105                 110

Ala Val Thr Ala Lys Thr Ser Thr Ser Val Ser Leu Thr Trp Ala Ala
        115                 120                 125

Ser Thr Asp Asp Lys Gln Val Ile Gly Tyr Thr Val Tyr Tyr Asn Asp
    130                 135                 140

Asn Leu Gln Ala Val Thr Gln Thr Asn Ala Thr Ile Thr Asn Leu Ile
145                 150                 155                 160

Pro Asn Thr Thr Tyr Thr Phe Thr Val Lys Ala Lys Asp Asn Gln Gly
                165                 170                 175

Leu Glu Ser Glu Ala Ser Gln Pro Leu Lys Val Thr Thr Asp Thr Asp
            180                 185                 190

Thr Leu Pro Pro Glu Pro Ala Thr Pro Cys Arg Pro Ala Gly Leu Tyr
        195                 200                 205

Asp Ser Gly Val Lys Asn Ile Pro Tyr Cys Gln Ala His Asp Gln Asp
    210                 215                 220

Gly Arg Glu Lys Leu Ala Asn Asp Ser Lys Arg Ile Ile Gly Tyr
225                 230                 235                 240

Phe Thr Ser Trp Arg Thr Gly Lys Asn Gly Gln Ser Lys Tyr Leu Val
                245                 250                 255

Thr Asp Ile Pro Trp Lys Asn Leu Thr His Ile Asn Tyr Ala Phe Ala
            260                 265                 270

His Val Asp Ser Asn Asn Arg Val Ser Val Gly Ser Pro Thr Asp Pro
        275                 280                 285
```

-continued

```
Thr Asn Pro Ala Leu Gly Leu Thr Trp Pro Glu Tyr Pro Asp Ala Leu
290                 295                 300
Met Asp Pro Ser Leu Pro Tyr Lys Gly His Phe Asn Leu Leu Thr Gln
305                 310                 315                 320
Trp Lys Lys Asn Pro Gly Val Lys Thr Leu Val Ser Val Gly Gly
                325                 330                 335
Trp Ala Glu Ser Gly Gly Tyr Ile Asp Glu Asn Gly Lys Arg Ile Ala
                340                 345                 350
Ser Gly Gly Phe Tyr Thr Met Thr Thr Asn Ala Asp Gly Ser Val Asn
                355                 360                 365
Gln Ala Ala Ile Asp Thr Phe Ala Thr Ser Ala Val Asp Phe Leu Arg
370                 375                 380
Lys Tyr Asn Phe Glu Gly Ile Asp Ile Asp Tyr Glu Tyr Pro Thr Thr
385                 390                 395                 400
Met Asn Gln Ala Gly Asn Pro Leu Asp Trp Gln Phe Ser Thr Pro Arg
                405                 410                 415
Leu Lys Gly Leu Met Glu Gly Tyr Asn Ala Leu Leu Lys Thr Leu Arg
                420                 425                 430
Val Lys Leu Asp Gln Ala Ser Ala Glu Asp Glu Lys Tyr Tyr Met Leu
                435                 440                 445
Thr Ile Ala Ser Pro Ser Ser Ala Tyr Leu Leu Arg Gly Met Glu Ser
450                 455                 460
Phe Gln Ala Leu Lys Tyr Leu Asp Tyr Val Asn Val Met Ser Tyr Asp
465                 470                 475                 480
Leu His Gly Ala Trp Asn Glu Phe Val Gly Pro Asn Ala Ala Leu Phe
                485                 490                 495
Asp Asp Gly Lys Asp Gly Glu Leu Ile Lys Tyr Asn Ile Tyr Asn Thr
                500                 505                 510
Pro Gln Tyr Gly Gly Ile Gly Tyr Leu Asn Thr Asp Trp Ala Tyr His
                515                 520                 525
Tyr Met Arg Gly Met Met Gln Ala Gly Arg Ile Asn Ile Gly Val Pro
530                 535                 540
Tyr Tyr Thr Arg Gly Phe Gln Asn Val Val Gly Gly Thr Asp Gly Leu
545                 550                 555                 560
Trp Gly Lys Ala Val Gly Lys Asn Cys Pro Thr Gly Leu Thr Ala Cys
                565                 570                 575
Gly Asp Gly Ala Thr Gly Ile Asp Asn Ile Trp His Asp Lys Asp Glu
                580                 585                 590
Asn Gly Lys Glu Glu Gly Ala Gly Ser Asn Pro Met Trp His Ala Lys
                595                 600                 605
Asn Leu Glu Lys Gly Ile Ala Gly Ser Tyr Leu Lys Asp His Gly Ile
610                 615                 620
Val Asn Pro Val Leu Thr Gly Thr Tyr Lys Arg Asn Tyr Asp Ser Thr
625                 630                 635                 640
Leu Val Ala Pro Trp Leu Trp Asn Ala Glu Lys Arg Val Phe Leu Ser
                645                 650                 655
Thr Glu Asp Glu Gln Ser Ile Gly Ala Lys Ala Asp Tyr Val Ile Lys
                660                 665                 670
Asn Gly Ile Gly Gly Ile Met Ile Trp Glu Leu Ala Gly Asp Tyr Asp
                675                 680                 685
Trp Tyr Lys Asp Arg Asn Asp Gly Lys Gly Glu Tyr Tyr Met Gly Ser
690                 695                 700
Thr Leu Thr Lys Leu Met His Arg Lys Phe Ser Thr Ala Thr Pro His
```

-continued

```
            705                 710                 715                 720
Asp Ala Ser Asn Ser Lys Thr Pro Leu Pro Ala Asp Lys Leu Ala Leu
                    725                 730                 735

Lys Ile Glu Val Thr Gly Phe Gln Leu Gly Asp Gln Asn Tyr Pro Ile
                740                 745                 750

Asn Pro Thr Leu Lys Ile Thr Asn Asn Ser Asn Leu Thr Ile Thr Gly
            755                 760                 765

Gly Ser Val Ile Glu Phe Asp Val Pro Thr Ser Thr Ala Gln Phe
        770                 775                 780

Ser Ser Tyr Gly Gly Asp Ser Val Lys Ile Ile Ser Ala Gly His Thr
785                 790                 795                 800

Gly Pro Asn Val Gly Gly Leu Lys Gly Asp Phe His Arg Val Ala Val
                805                 810                 815

Thr Ile Pro Thr Trp Lys Ser Val Ala Pro Gly Gln Ser Ile Asp Met
                820                 825                 830

Ser Ile Val Tyr Tyr Val Pro Ile Ser Gly Pro Thr Asn Tyr Thr Ile
                835                 840                 845

Thr Ile Asp Gly Lys Lys Tyr Ala Val Thr Asp Lys
            850                 855                 860

<210> SEQ ID NO 5
<211> LENGTH: 819
<212> TYPE: PRT
<213> ORGANISM: Brevibacillus laterosporus LAK1210 (MTCC5487)

<400> SEQUENCE: 5

Ser Pro Ile Cys Ser Ala Val Trp Asp Ser Lys Thr Ile Tyr Thr Ser
1               5                   10                  15

Gly Gln Gln Ala Ser Tyr Lys Gly His Glu Trp Thr Ala Lys Trp Trp
                20                  25                  30

Thr Gln Gly Glu Glu Pro Gly Thr Ser Asp Val Trp Gln Asp Leu Gly
            35                  40                  45

Val Cys Ser Thr Asn Pro Thr Asn Pro Pro Asp Pro Ser Asn Thr Pro
    50                  55                  60

Pro Thr Val Pro Thr Asn Leu Ala Val Thr Ala Lys Thr Ser Thr Ser
65                  70                  75                  80

Val Ser Leu Thr Trp Ala Ala Ser Thr Asp Asp Lys Gln Val Ile Gly
                85                  90                  95

Tyr Thr Val Tyr Tyr Asn Asp Asn Leu Gln Ala Val Thr Gln Thr Asn
                100                 105                 110

Ala Thr Ile Thr Asn Leu Ile Pro Asn Thr Thr Tyr Thr Phe Thr Val
            115                 120                 125

Lys Ala Lys Asp Asn Gln Gly Leu Glu Ser Glu Ala Ser Gln Pro Leu
130                 135                 140

Lys Val Thr Thr Asp Thr Asp Thr Leu Pro Pro Glu Pro Ala Thr Pro
145                 150                 155                 160

Cys Arg Pro Ala Gly Leu Tyr Asp Ser Gly Val Lys Asn Ile Pro Tyr
                165                 170                 175

Cys Gln Ala His Asp Gln Asp Gly Arg Glu Lys Leu Ala Asn Asp Ser
            180                 185                 190

Lys Arg Arg Ile Ile Gly Tyr Phe Thr Ser Trp Arg Thr Gly Lys Asn
        195                 200                 205

Gly Gln Ser Lys Tyr Leu Val Thr Asp Ile Pro Trp Lys Asn Leu Thr
    210                 215                 220
```

-continued

```
His Ile Asn Tyr Ala Phe Ala His Val Asp Ser Asn Asn Arg Val Ser
225                 230                 235                 240

Val Gly Ser Pro Thr Asp Pro Thr Asn Pro Ala Leu Gly Leu Thr Trp
            245                 250                 255

Pro Glu Tyr Pro Asp Ala Leu Met Asp Pro Ser Leu Pro Tyr Lys Gly
        260                 265                 270

His Phe Asn Leu Leu Thr Gln Trp Lys Lys Asn Pro Gly Val Lys
    275                 280                 285

Thr Leu Val Ser Val Gly Gly Trp Ala Glu Ser Gly Gly Tyr Ile Asp
290                 295                 300

Glu Asn Gly Lys Arg Ile Ala Ser Gly Gly Phe Tyr Thr Met Thr Thr
305                 310                 315                 320

Asn Ala Asp Gly Ser Val Asn Gln Ala Ala Ile Asp Thr Phe Ala Thr
                325                 330                 335

Ser Ala Val Asp Phe Leu Arg Lys Tyr Asn Phe Glu Gly Ile Asp Ile
                340                 345                 350

Asp Tyr Glu Tyr Pro Thr Thr Met Asn Gln Ala Gly Asn Pro Leu Asp
            355                 360                 365

Trp Gln Phe Ser Thr Pro Arg Leu Lys Gly Leu Met Glu Gly Tyr Asn
370                 375                 380

Ala Leu Leu Lys Thr Leu Arg Val Lys Leu Asp Gln Ala Ser Ala Glu
385                 390                 395                 400

Asp Glu Lys Tyr Tyr Met Leu Thr Ile Ala Ser Pro Ser Ser Ala Tyr
                405                 410                 415

Leu Leu Arg Gly Met Glu Ser Phe Gln Ala Leu Lys Tyr Leu Asp Tyr
            420                 425                 430

Val Asn Val Met Ser Tyr Asp Leu His Gly Ala Trp Asn Glu Phe Val
            435                 440                 445

Gly Pro Asn Ala Ala Leu Phe Asp Asp Gly Lys Asp Gly Glu Leu Ile
        450                 455                 460

Lys Tyr Asn Ile Tyr Asn Thr Pro Gln Tyr Gly Gly Ile Gly Tyr Leu
465                 470                 475                 480

Asn Thr Asp Trp Ala Tyr His Tyr Met Arg Gly Met Met Gln Ala Gly
            485                 490                 495

Arg Ile Asn Ile Gly Val Pro Tyr Tyr Thr Arg Gly Phe Gln Asn Val
            500                 505                 510

Val Gly Gly Thr Asp Gly Leu Trp Gly Lys Ala Val Gly Lys Asn Cys
            515                 520                 525

Pro Thr Gly Leu Thr Ala Cys Gly Asp Gly Ala Thr Gly Ile Asp Asn
        530                 535                 540

Ile Trp His Asp Lys Asp Glu Asn Gly Lys Glu Glu Gly Ala Gly Ser
545                 550                 555                 560

Asn Pro Met Trp His Ala Lys Asn Leu Glu Lys Gly Ile Ala Gly Ser
            565                 570                 575

Tyr Leu Lys Asp His Gly Ile Val Asn Pro Val Leu Thr Gly Thr Tyr
            580                 585                 590

Lys Arg Asn Tyr Asp Ser Thr Leu Val Ala Pro Trp Leu Trp Asn Ala
        595                 600                 605

Glu Lys Arg Val Phe Leu Ser Thr Glu Asp Gln Ser Ile Gly Ala
        610                 615                 620

Lys Ala Asp Tyr Val Ile Lys Asn Gly Ile Gly Gly Ile Met Ile Trp
625                 630                 635                 640

Glu Leu Ala Gly Asp Tyr Asp Trp Tyr Lys Asp Arg Asn Asp Gly Lys
```

```
                    645                 650                 655
Gly Glu Tyr Tyr Met Gly Ser Thr Leu Thr Lys Leu Met His Arg Lys
                660                 665                 670

Phe Ser Thr Ala Thr Pro His Asp Ala Ser Asn Ser Lys Thr Pro Leu
            675                 680                 685

Pro Ala Asp Lys Leu Ala Leu Lys Ile Glu Val Thr Gly Phe Gln Leu
        690                 695                 700

Gly Asp Gln Asn Tyr Pro Ile Asn Pro Thr Leu Lys Ile Thr Asn Asn
705                 710                 715                 720

Ser Asn Leu Thr Ile Thr Gly Gly Ser Val Ile Glu Phe Asp Val Pro
                725                 730                 735

Thr Ser Thr Ser Ala Gln Phe Ser Ser Tyr Gly Gly Asp Ser Val Lys
            740                 745                 750

Ile Ile Ser Ala Gly His Thr Gly Pro Asn Val Gly Gly Leu Lys Gly
        755                 760                 765

Asp Phe His Arg Val Ala Val Thr Ile Pro Thr Trp Lys Ser Val Ala
    770                 775                 780

Pro Gly Gln Ser Ile Asp Met Ser Ile Val Tyr Tyr Val Pro Ile Ser
785                 790                 795                 800

Gly Pro Thr Asn Tyr Thr Ile Thr Ile Asp Gly Lys Lys Tyr Ala Val
                805                 810                 815

Thr Asp Lys

<210> SEQ ID NO 6
<211> LENGTH: 126
<212> TYPE: DNA
<213> ORGANISM: Brevibacillus laterosporus LAK1210 (MTCC5487)

<400> SEQUENCE: 6
atgcgcaaaa tgtatcagca tattccgacc gcgcatagcg tgcgcaaatt taactttctg      60
ctgctggcgt tgtgctgttt tgcgagcatt tttccggcga ttctgccggc gagcgtgagc     120
gcgagc                                                                126

<210> SEQ ID NO 7
<211> LENGTH: 20
<212> TYPE: PRT
<213> ORGANISM: Brevibacillus laterosporus LAK1210 (MTCC5487)

<400> SEQUENCE: 7

Ile Glu Val Thr Gly Phe Gln Leu Gly Asp Gln Asn Tyr Pro Ile Asn
1               5                   10                  15

Pro Thr Leu Lys
            20

<210> SEQ ID NO 8
<211> LENGTH: 16
<212> TYPE: PRT
<213> ORGANISM: Brevibacillus laterosporus LAK1210 (MTCC5487)

<400> SEQUENCE: 8

Asn Tyr Asp Ser Thr Leu Val Ala Pro Trp Leu Trp Asn Ala Glu Lys
1               5                   10                  15

<210> SEQ ID NO 9
<211> LENGTH: 17
<212> TYPE: PRT
<213> ORGANISM: Brevibacillus laterosporus LAK1210 (MTCC5487)
```

-continued

```
<400> SEQUENCE: 9

Asn Leu Thr His Ile Asn Tyr Ala Phe Ala His Val Asp Ser Asn Asn
1               5                   10                  15

Arg

<210> SEQ ID NO 10
<211> LENGTH: 14
<212> TYPE: PRT
<213> ORGANISM: Brevibacillus laterosporus LAK1210 (MTCC5487)

<400> SEQUENCE: 10

Val Phe Leu Ser Thr Glu Asp Glu Gln Ser Ile Gly Ala Lys
1               5                   10

<210> SEQ ID NO 11
<211> LENGTH: 16
<212> TYPE: PRT
<213> ORGANISM: Brevibacillus laterosporus LAK1210 (MTCC5487)

<400> SEQUENCE: 11

Ala Lys Asp Asn Gln Gly Leu Glu Ser Glu Ala Ser Gln Pro Leu Lys
1               5                   10                  15

<210> SEQ ID NO 12
<211> LENGTH: 14
<212> TYPE: PRT
<213> ORGANISM: Brevibacillus laterosporus LAK1210 (MTCC5487)

<400> SEQUENCE: 12

Asp Asn Gln Gly Leu Glu Ser Glu Ala Ser Gln Pro Leu Lys
1               5                   10

<210> SEQ ID NO 13
<211> LENGTH: 15
<212> TYPE: PRT
<213> ORGANISM: Brevibacillus laterosporus LAK1210 (MTCC5487)

<400> SEQUENCE: 13

Gly Phe Gln Asn Val Val Gly Gly Thr Asp Gly Leu Trp Gly Lys
1               5                   10                  15

<210> SEQ ID NO 14
<211> LENGTH: 18
<212> TYPE: PRT
<213> ORGANISM: Brevibacillus laterosporus LAK1210 (MTCC5487)

<400> SEQUENCE: 14

Asp Glu Asn Gly Lys Glu Glu Gly Ala Gly Ser Asn Pro Met Trp His
1               5                   10                  15

Ala Lys

<210> SEQ ID NO 15
<211> LENGTH: 15
<212> TYPE: PRT
<213> ORGANISM: Brevibacillus laterosporus LAK1210 (MTCC5487)

<400> SEQUENCE: 15

Asn Asp Gly Lys Gly Glu Tyr Tyr Met Gly Ser Thr Leu Thr Lys
1               5                   10                  15

<210> SEQ ID NO 16
<211> LENGTH: 14
<212> TYPE: PRT
```

<213> ORGANISM: Brevibacillus laterosporus LAK1210 (MTCC5487)

<400> SEQUENCE: 16

Asp His Gly Ile Val Asn Pro Val Leu Thr Gly Thr Tyr Lys
1               5                   10

<210> SEQ ID NO 17
<211> LENGTH: 10
<212> TYPE: PRT
<213> ORGANISM: Brevibacillus laterosporus LAK1210 (MTCC5487)

<400> SEQUENCE: 17

Gly His Phe Asn Leu Leu Thr Gln Trp Lys
1               5                   10

<210> SEQ ID NO 18
<211> LENGTH: 18
<212> TYPE: PRT
<213> ORGANISM: Brevibacillus laterosporus LAK1210 (MTCC5487)

<400> SEQUENCE: 18

Asp Glu Asn Gly Lys Glu Glu Gly Ala Gly Ser Asn Pro Met Trp His
1               5                   10                  15

Ala Lys

<210> SEQ ID NO 19
<211> LENGTH: 13
<212> TYPE: PRT
<213> ORGANISM: Brevibacillus laterosporus LAK1210 (MTCC5487)

<400> SEQUENCE: 19

Glu Glu Gly Ala Gly Ser Asn Pro Met Trp His Ala Lys
1               5                   10

<210> SEQ ID NO 20
<211> LENGTH: 16
<212> TYPE: PRT
<213> ORGANISM: Brevibacillus laterosporus LAK1210 (MTCC5487)

<400> SEQUENCE: 20

Tyr Tyr Met Leu Thr Ile Ala Ser Pro Ser Ser Ala Tyr Leu Leu Arg
1               5                   10                  15

<210> SEQ ID NO 21
<211> LENGTH: 10
<212> TYPE: PRT
<213> ORGANISM: Brevibacillus laterosporus LAK1210 (MTCC5487)

<400> SEQUENCE: 21

Leu Asp Gln Ala Ser Ala Glu Asp Glu Lys
1               5                   10

<210> SEQ ID NO 22
<211> LENGTH: 11
<212> TYPE: PRT
<213> ORGANISM: Brevibacillus laterosporus LAK1210 (MTCC5487)

<400> SEQUENCE: 22

Gly Glu Tyr Tyr Met Gly Ser Thr Leu Thr Lys
1               5                   10

<210> SEQ ID NO 23
<211> LENGTH: 15
<212> TYPE: PRT

<213> ORGANISM: Brevibacillus laterosporus LAK1210 (MTCC5487)

<400> SEQUENCE: 23

Asn Asp Gly Lys Gly Glu Tyr Tyr Met Gly Ser Thr Leu Thr Lys
1               5                   10                  15

<210> SEQ ID NO 24
<211> LENGTH: 15
<212> TYPE: PRT
<213> ORGANISM: Brevibacillus laterosporus LAK1210 (MTCC5487)

<400> SEQUENCE: 24

Ile Ile Ser Ala Gly His Thr Gly Pro Asn Val Gly Gly Leu Lys
1               5                   10                  15

<210> SEQ ID NO 25
<211> LENGTH: 11
<212> TYPE: PRT
<213> ORGANISM: Brevibacillus laterosporus LAK1210 (MTCC5487)

<400> SEQUENCE: 25

Gly Glu Tyr Tyr Met Gly Ser Thr Leu Thr Lys
1               5                   10

<210> SEQ ID NO 26
<211> LENGTH: 11
<212> TYPE: PRT
<213> ORGANISM: Brevibacillus laterosporus LAK1210 (MTCC5487)

<400> SEQUENCE: 26

Gly Leu Met Glu Gly Tyr Asn Ala Leu Leu Lys
1               5                   10

<210> SEQ ID NO 27
<211> LENGTH: 13
<212> TYPE: PRT
<213> ORGANISM: Brevibacillus laterosporus LAK1210 (MTCC5487)

<400> SEQUENCE: 27

Glu Glu Gly Ala Gly Ser Asn Pro Met Trp His Ala Lys
1               5                   10

<210> SEQ ID NO 28
<211> LENGTH: 9
<212> TYPE: PRT
<213> ORGANISM: Brevibacillus laterosporus LAK1210 (MTCC5487)

<400> SEQUENCE: 28

Gly Met Glu Ser Phe Gln Ala Leu Lys
1               5

<210> SEQ ID NO 29
<211> LENGTH: 12
<212> TYPE: PRT
<213> ORGANISM: Brevibacillus laterosporus LAK1210 (MTCC5487)

<400> SEQUENCE: 29

Thr Ile Tyr Thr Ser Gly Gln Gln Ala Ser Tyr Lys
1               5                   10

<210> SEQ ID NO 30
<211> LENGTH: 11
<212> TYPE: PRT
<213> ORGANISM: Brevibacillus laterosporus LAK1210 (MTCC5487)

<400> SEQUENCE: 30

Gly Leu Met Glu Gly Tyr Asn Ala Leu Leu Lys
1               5                   10

<210> SEQ ID NO 31
<211> LENGTH: 9
<212> TYPE: PRT
<213> ORGANISM: Brevibacillus laterosporus LAK1210 (MTCC5487)

<400> SEQUENCE: 31

Tyr Leu Val Thr Asp Ile Pro Trp Lys
1               5

<210> SEQ ID NO 32
<211> LENGTH: 9
<212> TYPE: PRT
<213> ORGANISM: Brevibacillus laterosporus LAK1210 (MTCC5487)

<400> SEQUENCE: 32

Ile Ile Gly Tyr Phe Thr Ser Trp Arg
1               5

<210> SEQ ID NO 33
<211> LENGTH: 9
<212> TYPE: PRT
<213> ORGANISM: Brevibacillus laterosporus LAK1210 (MTCC5487)

<400> SEQUENCE: 33

Gly Met Glu Ser Phe Gln Ala Leu Lys
1               5

<210> SEQ ID NO 34
<211> LENGTH: 10
<212> TYPE: PRT
<213> ORGANISM: Brevibacillus laterosporus LAK1210 (MTCC5487)

<400> SEQUENCE: 34

Ile Asn Ile Gly Val Pro Tyr Tyr Thr Arg
1               5                   10

<210> SEQ ID NO 35
<211> LENGTH: 27
<212> TYPE: PRT
<213> ORGANISM: Brevibacillus laterosporus LAK1210 (MTCC5487)

<400> SEQUENCE: 35

Val Thr Thr Asp Thr Asp Thr Leu Pro Pro Glu Pro Ala Thr Pro Cys
1               5                   10                  15

Arg Pro Ala Gly Leu Tyr Asp Ser Gly Val Lys
            20                  25

<210> SEQ ID NO 36
<211> LENGTH: 9
<212> TYPE: PRT
<213> ORGANISM: Brevibacillus laterosporus LAK1210 (MTCC5487)

<400> SEQUENCE: 36

Val Ala Val Thr Ile Pro Thr Trp Lys
1               5

<210> SEQ ID NO 37
<211> LENGTH: 7
<212> TYPE: PRT
<213> ORGANISM: Brevibacillus laterosporus LAK1210 (MTCC5487)

```
<400> SEQUENCE: 37

Gly His Glu Trp Thr Ala Lys
1               5

<210> SEQ ID NO 38
<211> LENGTH: 7
<212> TYPE: PRT
<213> ORGANISM: Brevibacillus laterosporus LAK1210 (MTCC5487)

<400> SEQUENCE: 38

Lys Tyr Ala Val Thr Asp Lys
1               5

<210> SEQ ID NO 39
<211> LENGTH: 12
<212> TYPE: PRT
<213> ORGANISM: Brevibacillus laterosporus LAK1210 (MTCC5487)

<400> SEQUENCE: 39

Val Lys Leu Asp Gln Ala Ser Ala Glu Asp Glu Lys
1               5                   10

<210> SEQ ID NO 40
<211> LENGTH: 42
<212> TYPE: PRT
<213> ORGANISM: Brevibacillus laterosporus LAK1210 (MTCC5487)

<400> SEQUENCE: 40

Met Arg Lys Met Tyr Gln His Ile Pro Thr Ala His Ser Val Arg Lys
1               5                   10                  15

Phe Asn Phe Leu Leu Leu Ala Phe Val Leu Phe Ala Ser Ile Phe Pro
                20                  25                  30

Ala Ile Leu Pro Ala Ser Val Ser Ala Ser
            35                  40
```